US012661318B2

(12) United States Patent
Husseini et al.

(10) Patent No.: US 12,661,318 B2
(45) Date of Patent: *Jun. 23, 2026

(54) SYSTEMS AND METHODS FOR TARGETED BREAST CANCER THERAPIES

(71) Applicant: American University of Sharjah, Sharjah (AE)

(72) Inventors: Ghaleb Husseini, Sharjah (AE); Mohammad Al-Sayah, Sharjah (AE); Amal Elsadig, Sharjah (AE)

(73) Assignee: American University of Sharjah, Sharjah (AE)

( * ) Notice: Subject to any disclaimer, the term of this patent is extended or adjusted under 35 U.S.C. 154(b) by 240 days.

This patent is subject to a terminal disclaimer.

(21) Appl. No.: 18/407,246

(22) Filed: Jan. 8, 2024

(65) Prior Publication Data

US 2024/0261222 A1 Aug. 8, 2024

Related U.S. Application Data

(63) Continuation of application No. 17/119,001, filed on Dec. 11, 2020, now Pat. No. 11,865,212, which is a
(Continued)

(51) Int. Cl.
A61K 9/1271 (2025.01)
A61K 31/704 (2006.01)
(Continued)

(52) U.S. Cl.
CPC .......... A61K 9/1271 (2013.01); A61K 31/704 (2013.01); A61K 41/0028 (2013.01);
(Continued)

(58) Field of Classification Search
CPC ................................................... A61K 9/1271
See application file for complete search history.

(56) References Cited

U.S. PATENT DOCUMENTS 5,192,549 A 3/1993 Barenolz et al.
5,460,595 A 10/1995 Hall et al.
(Continued)

FOREIGN PATENT DOCUMENTS

KR 2016/0011771 A 2/2016

OTHER PUBLICATIONS

"A Basic guide to particle characterization: https://www.cif.iastate.edu/sites/default/files/uploads/Other_Inst/Particle%20Size/Particle%20Characterization%20Guide.pdf retreived on Jan. 13, 2020".
(Continued)

*Primary Examiner* — Carlos A Azpuru
(74) *Attorney, Agent, or Firm* — Knobbe, Martens, Olson & Bear, LLP

(57) ABSTRACT

Systems and methods for producing liposomes, including control liposomes and immunoliposomes targeting breast cancer are provided. Systems and methods for treating breast cancer, using targeted immunoliposomes produced according to various methods are also disclosed herein. For example, trastuzumab-conjugated immunoliposomes may be used to deliver chemotherapeutic agents to breast cancer tissues for the treatment of breast cancer. Systems and methods for actuating liposomes using ultrasound are also disclosed, such as systems and methods for actuating trastuzumab-conjugated liposomes accumulated in breast cancer tissues for the treatment of breast cancer.

20 Claims, 29 Drawing Sheets

Related U.S. Application Data continuation of application No. 16/159,550, filed on Oct. 12, 2018, now Pat. No. 10,864,161.

(60) Provisional application No. 62/572,358, filed on Oct. 13, 2017.

(51) Int. Cl.
| | |
|---|---|
| *A61K 41/00* | (2020.01) |
| *A61K 47/68* | (2017.01) |
| *A61K 47/69* | (2017.01) |
| *A61M 37/00* | (2006.01) |
| *A61P 35/00* | (2006.01) |

(52) U.S. Cl.
CPC ...... *A61K 47/6849* (2017.08); *A61K 47/6855* (2017.08); *A61K 47/6913* (2017.08); *A61M 37/0092* (2013.01); *A61P 35/00* (2018.01)

(56) References Cited

U.S. PATENT DOCUMENTS

| | | | |
|---|---|---|---|
| 5,549,638 | A | 8/1996 | Burdette |
| 9,005,942 | B2 | 4/2015 | Chen et al. |
| 10,864,161 | B2 * | 12/2020 | Husseini ............ A61K 47/6855 |
| 11,865,212 | B2 * | 1/2024 | Husseini ........... A61M 37/0092 |
| 2005/0043726 | A1 | 2/2005 | McHale |
| 2008/0286350 | A1 | 11/2008 | Bally |
| 2010/0209494 | A1 | 8/2010 | Kamps et al. |
| 2014/0302205 | A1 | 10/2014 | Melnik |
| 2014/0356414 | A1 | 12/2014 | Wang et al. |
| 2015/0056270 | A1 * | 2/2015 | Hamada ................. A61K 9/127 |
| | | | 424/174.1 |
| 2017/0028390 | A1 | 2/2017 | Reynolds |
| 2018/0051209 | A1 | 2/2018 | Akhavan-Tafti |
| 2019/0070115 | A1 | 3/2019 | Rwei et al. |
| 2021/0113465 | A1 | 4/2021 | Husseini et al. |

OTHER PUBLICATIONS

Avi Schroeder, Joseph Kost, Yechezkel Barenholz. "Ultrasound, liposomes, and drug delivery: principles for using ultrasound to control the release of drugs from liposomes". Chemistry and Physics of Lipids 162, (2009) pp. 1-6, (Year: 2009).

"Bicinchoninic Acid Protein Assay Kit," Sigma-Aldrich, Missouri, USA, Rep., 2012.

"Cancer Fact Sheet N°297," World Health Organization, [Online]. Available: http://www.who.int/mediacentre/factsheets/fs297/en/, 2014 [Accessed Apr. 4, 2017].

"Cancer multidrug resistance," Nat. Biotechnol., vol. 18, pp. 18-20, 2000.

"Cancer Statistics for 2014," American Cancer Soc., Atlanta, Georgia, Rep., 2014.

"Estrogens." [Online]. Available: http://www.webmd.com/women/estrogens, [Accessed: Apr. 4, 2017].

"How DLS works." [Online]. Available: http://wyatt.eu/index.php?id=how-dls-works, [Accessed: Apr. 4, 2017].

"Timeline: Major Milestones Against Cancer | CancerProgress. Net," American Society of Clinical Oncology (ASCO), Alexandria, Virgina, Rep. (2013).

"What Is Cancer? What Causes Cancer?" [Online]. Available: http://www.medicalnewstoday.com/info/canceroncology/, 2014 [Accessed: Apr. 4, 2017].

"What Is Cancer?," National Cancer Institute, [Online]. Available: http://www.cancer.gov/cancertopics/cancerlibrary/what-is-cancer, 2014 [Accessed Apr. 4, 2017].

"Chemotherapy," Belvoir Media Group, LLC, Norwalk, Nov. 2010. Available: http://ezproxy.aus.edu/login?url=http://search.proquest. com/docview/1370739922?accountid=16946.

A. A. Gabizon, "Pegylated Liposomal Doxorubicin: Metamorphosis of an Old Drug into a New Form of Chemotherapy," Cancer Invest., vol. 19, No. 4, pp. 424-436, 2001.

A. Akbarzadeh, R. Rezaei-Sadabady, S. Davaran, S. W. Joo, N. Zargharni, Y. Hanifehpour, M. Samiei,M. Kouhi, and K. Nejati-Koshki, "Liposome: classification, preparation, and applications," Nanoscale Res. Lett., vol. 8, No. 1, p. 102-110, Jan. 2013.

A. Azagury, L. Khoury, G. Enden, and J. Kost, "Ultrasound mediated transdermal drug delivery.," Adv. DrugDeliv. Rev., vol. 72, pp. 127-143, Jun. 2014.

A. Blume, "A comparative study of the phase transitions of phospholipid bilayers and monolayers," Biochim. Biophys. Acta, vol. 557, No. 1, pp. 32-44, Oct. 1979.

A. Dickason and B. Waldera (Mar. 9, 2011). Polymeric Drug Delivery Systems—Biomaterials UNDEngineering [Video file]. Available: http://www.youtube.com/watch?v=b5PhiTOC6hO, [Accessed: Apr. 4, 2017]. (Youtube—figure out how to cite?).

A. E. Catania, A. Ferrari, M. Manno, and E. Spessa, "A Comprehensive Thermodynamic Approach to Acoustic Cavitation Simulation in High-Pressure Injection Systems by a Conservative Homogeneous Two-Phase Barotropic Flow Model," J. Eng. Gas Turbines Power, vol. 128, No. 2, pp. 434-445, 2006.

A. Gabizon, D. C. Price, J. Huberty, R. S. Bresalier, and D. Papahadjopoulos, "Effect of Liposome Composition and Other Factors on the Targeting of Liposomes to Experimental Tumors: Biodistributjon and Imaging Studies1," Cancer Res., vol. 50, pp. 6371-6379, 1990.

A. K. Iyer, G. Khaled, J. Fang, and H. Maeda, "Exploiting the enhanced permeability and retention effect for tumor targeting," Drug Discov. Today, vol. 11,No. 17-18,pp. 812-880, Sep. 2006.

A. Khaibullina, B.-S. Jang, H. Sun, N. Le, S. Yu, V. Frenkel, J. A. Carrasquillo, I. Pastan, K. C. P. Li, and C.H. Paik, "Pulsed high-intensity focused ultrasound enhances uptake of radiolabeled monoclonal antibody to human epidermoid tumor in nude mice," J Nucl. Med., vol. 49, No. 2, pp. 295-302, Mar. 2008.

A. Kolate, D. Baradia, S. Patil, I. Vhora, G. Kore, and A. Misra, "PEG—A versatile conjugating ligand for drugs and drug delivery systems.," J. Control. Release, vol. 192C, pp. 67-81, Oct. 2014.

A. L.B. Seynhaeve, B. M. Dicheva, S. Hoving, G. A. Koning, and T. L. M. ten Hagen, "Intact Doxil is taken up intracellularly and released doxorubicin sequesters in the lysosome: evaluated by in vitro/in vivo live cell imaging," J Control. Release, vol. 172, No. 1, pp. 330-340, Nov. 2013.

A. Marin, H. Sun, G. A. Husseini, W. G. Pitt, D. A. Christensen, and N. Y. Rapoport, "Drug delivery in pluronic micelles: effect of high-frequency ultrasound on drug release from micelles and intracellular uptake," J. Control. Release, vol. 84, No. 1-2, pp. 39-47, Nov. 2002.

A. Porfire, I. Tomuta, L. Tefas, S. E. Leucuta, and M. Achim, "Simultaneous quantification of I-a.-phosphatidylcholine and cholesterol in liposomes using near infrared spectrometry and chemometry;" J. Pharm. Biomed. Anal., vol. 63, pp. 87-94, Apr. 2012.

A. Ranjan, G. C. Jacobs, D. L. Woods, A. H. Negussie, A. Partanen, P. S. Yarmolenko, C. E. Gacchina, K. V Sharma, V. Frenkel, B. J. Wood, and M. R. Dreher, "Image-guided drug delivery with magnetic resonance guided high intensity focused ultrasound and temperature sensitive liposomes in a rabbit Vx2 tumor model," J Control. Release, vol. 158, No. 3, pp. 487-494, Mar. 2012.

A. Schroeder, J. Kost, and Y. Barenholz, "Ultrasound, liposomes, and drug delivery: principles for using ultrasound to control the release of drugs from liposomes," Chem. Phys. Lipids, vol. 162, No. 1-2, pp. 1-16, Nov. 2009.

A. Schroeder, Y. Avnir, S. Weisman, Y. Najajreh, A. Gabizon, Y. Talmon, J. Kost, and Y. Barenholz, "Controlling Liposomal Drug Release with Low Frequency Ultrasound: Mechanism and Feasibility," No. 19, pp. 4019-4025, 2007.

Afadzi, Mercy, et al. "Mechanisms of the ultrasound-mediated intracellular delivery of liposomes and dextrans." IEEE transactions on ultrasonics, ferroelectrics, and frequency control 60.1 (2013): 21-33.

Anand, Preetha, et al. "Cancer is a preventable disease that requires major lifestyle changes." Pharmaceutical research 25.9 (2008): 2097-2116.

(56)         References Cited

OTHER PUBLICATIONS

B. Colagiuri, H. Dhillon, P. N. Butow, J. Jansen, K. Cox, and J. Jacquet, "Does assessing patients' expectancies about chemotherapy side effects influence their occurrence?," J. Pain Symptom Manage., vol. 46, No. 2, pp. 275-281, Aug. 2013.

B. J. Staples, W. G. Pitt, B. L. Roeder, G. A. Husseini, D. Rajeev, and G. B. Schaalje, "Distribution of doxorubicin in rats undergoing ultrasonic drug delivery," J. Pharm. Sci., vol. 99, No. 7, pp. 3122-3131, Jul. 2010.

B. M. Gabizon A. A., Barenholz Y, "Prolongation of the circulation time of doxorubicin encapsulated in liposomes containing a polyethylene glycol-derivatized phospholipid: pharmacokinetic studies in rodents and dogs.," Pharm. Res., vol. 10, No. 5, pp. 703-708, 1993.

B. Maherani, E. Arab-Tehrany, A. Kheirolomoom, D. Geny, and M. Linder, "Calcein release behavior from liposomal bilayer; influence of physicochemical/mechanical/structural properties of lipids," Biochimie, vol. 95, No. II, pp. 2018-2033, Nov. 2013.

B. Moghaddam, S. E. McNeil, Q. Zheng, A. R. Mohammed, and Y. Perrie, "Exploring the correlationbetween lipid packaging in lipoplexes and their transfection efficacy," Pharmaceutics, vol. 3, No. 4, pp. 848-864, 2011.

B. Theek, F. Gremse, S. Kunjachan, S. Fokong, R. Pola, M. Pechar, R. Deckers, G. Storm, J. Ehling, F. Kiessling, and T. Lammers, "Characterizing EPR-mediated passive drug targeting using contrast-enhanced functional ultrasound imaging.," J. Control. Release, vol. 182, pp. 83-89, May 2014.

Biltonen, Rodney L., and Dov Lichtenberg. "The use of differential scanning calorimetry as a tool to characterize liposome preparations." Chemistry and physics of lipids 64.1-3 (1993): 129-142.

C. Kirby and G. Gregoriadis, "The effect of the cholesterol content of small unilamellar liposomes on the fate of their lipid components," Life Sci., vol. 27, No. 23, pp. 2223-2230, Dec. 1980.

C. Levi, "Ultrasound for targeted delivery of cytotoxic drugs from liposomes," M.s. Thesis, Faculty of Engineering Science, Ben Gurion, Israel, 2000. [have abstract].

C. Lovelyn and A. Attama, "Current State of Nanoemulsions in Drug Delivery," J. Biomater. Nanobiotechnol., vol. 2, No. 5, pp. 626-639, 2011.

C. Obasaju and G. Hudes, "Paclitaxel and docetaxel in prostate cancer.," Hematol Oneal Clin North Am, vol. 15, No. 3, pp. 525-545, 2001.

C. Vuarchey, S. Kumar, and R. Schwendener, "Albumin coated liposomes: a novel platform for macrophage specific drug delivery," Nanotechnol. Dev., vol. 1, No. 1, Jul. 2011.

Chandrapala, Jayani, et al. "The effect of ultrasound on casein micelle integrity." Journal of dairy science 95.12 (2012): 6882-6890.

Conde, João, M. Jesus, and Pedro V. Baptista. "Nanomaterials for reversion of multidrug resistance in cancer: a new hope for an old idea ?." Front. Pharmacol., vol. 4, No. October, p. 134, Jan. 2013.

D. Ensminger. Ultrasonics: Fundamentals, Technology, Applications, Second Edition, Revised and Expanded. Chapters 1, 11, and 14, CRC Press, 1988.

D. K. Chang, De-Ku , et al. "Peptide-mediated liposomal Doxorubl •n enhances drug delivery efficiency an erapeutic efficacy in animal models." PLoS One 12 (2013): e83239.

D. Kim, A. D. Fried an, and R. Liu, "Tetraspecific ligand for tumor-targeted livery of nanomaterials,"Biomaterials, vol. 35, No. 23, pp. 6026-6036, Jul. 2014.

D. L. Berkson. Safe Hormones Smart Women. Indiana: iUniverse, 2010, p. 31.

D. L. Hoyert and J. Xu, "Deaths: Preliminary Data for 2011," National Vital St , Rep., 2012.

D. Lasi , "Liposomes synthetic lipid microspheres serve as multipurpose vehicles for dgs, genetic material and cosmetics," American Scientist, vol. 80, No. 1, pp. 20-31, 1992.

D. Martin, I. Wells, and C. Goodwin, "Physics of ultrasound," Anaesth. Intensive Care Med.: vol. 16, No. 3,pp. 132-135, Feb. 2015.

D. Needham, G. Anyarambhatla, G. Kong, and M. W. Dewhirst, "A New Temperature-sensit1 Liposome for Use with Mild Hyperthermia: Characterization and Testing in a Human Tumor XenaModel 1," Cancer Research, pp. 1197-1201, 2000.

D. O. Draper, J.C. Castel, and D. Castel, "Rate of temperature increase in human mustcle during 1 MHz and 3 MH continuous ultrasound.," J. Orthop. Sports Phys. Ther., vol. 22, No. 4 p. 142-50, Oct. 1995.

D.T. Sugerman, "Chemotherapy," JAMA, vol. 310, No. 2, pp. 218, 2013.

D. Wujcik, "Science and mechanism of action of targeted therapies in cancer treatment.," Semin. oneal. Nurs., vol. 30, No. 3, pp. 139-146, Aug. 2014.

Ding et al.: Recent Advances in Stimuli-Responsive Release Function Drug Delivery Ststems for Tumor Treatment, https://www.ncbi.nlm.nih.gov/pmc/articles/PMC6273707/pdf/molecules-21-01715.pdf.retreived on Jan. 10, 2020.

E. Cukierman and D. R. Kha n, "The benefits and challenges assoctiaed with the use of drug delivery systems in cancer ther y.," Biochem. Pharmacol., vol. 80, po. 5, pp. 762-770, Sep. 2010.

E. Forssen and M. Willis, "Ligand-targeted liposomes," Adv. Drug Deliv. Rev., vol. 29, No. 3, pp. 249-271, Feb. 1998.

E. L. Yuh, S. G. Shulman, S. A. Me a, J. Xie, L. Chen, V renkel, M. D. Bednarski, and K. C. P. Li, "Delivery of Systemic Chemotherape .c Agent to Tum s by Using Focused Ultrasound: Study in aMurine Model I," Radiology , v .234, .431-437, 2005.

E. S. Richardson, W. G. Pitt, and D. J. Woodbury , "The role of cavitation in liposome formation," Biophys. J, vol. 93, No. 12, pp. 4100-4107, Dec. 2007.

E. Troxell, M. Troxell, and J. Bell, "The Effect of Estrone on the Interaction between Phospholipase A and the Phospholipid Bilayer," J. undergrad. Res. Brigham Young Univ., 2013.

Eliaz, Rom E., and Francis C. Szoka. "Lipftome-encosulated doxorubicin targeted to CD44." Cancer research 61.6 (2001) 2592-2601.

F. Alexis, E. M. Pridgen, R. Langer, ans O. C. Farokhzad, Dr ug Delivery, vol. 197, M. Schafer-Korting, Ed. Springer Berlin Heidelberg, 2 0, pp. 55-86.

F. Szoka and D. Papahadjopoules', "Procedure for preparation of liposomes with large internal aqueous space and high capture by reverse-phase evaporation,".

Frenkel, Victor, et a . "Delivery of liposomal doxorubicin (Doxil) in breast cancer tumor model: investigation of patential enhancement by pulsed-high intensity focused ultrasound exposure."Academic radioloav 13.4 (2006): 469-479.

G. A. Husseini and W.G. Pitt, "Micelles and nanoparticles for ultrasonic drug and gene delivery," AdvaDrug Deliv. Rev.. vol. 60. No. 10. pp. 1137-52. Jun. 2008.

G. A. Husseini and W. G. Pitt, "The Use of Ultrasound and Micelles in Cancer treatment," J. Nanosci. Nanotechnol., vol. 8, No. 5, pp. 2205-2215, May 2008.

G. A. Husseini and W. G. Pitt, "Ultrasonic-Activated Micellar Drug Delivery for Cancer Treatment," J.Pharm. Sci., vol. 9999, No. 9999, pp. 795-811, 2008.

G. A. Husseini, D. Velluto, L. Kherbeck, W. G. Pitt, J. A. Hubbell, and D. A. Christensen, "investigatingt he acoustic release of doxorubicin from targeted micelles Ghaleb," Colloids and SurfacesB-:Biointerfaces, vol. 101, pp. 153-155, 2013.

G. A. Husseini, G.D. Myrup, W. G. Pitt, D. a Christensen, and N. Y. Rapoport, "Factors affecting acoustically triggered release of drugs from polymeric micelles.," J. Control. Release, vol. 69, No. 1 pp. 43-52, 2000.

G. A. Husseini, L. Kherbeck, W. G. Pitt, J. A. Hubbell, D. A. Christensen, and D. Velluto, "Kinetics of Ultrasonic Drug Delivery from Targeted Micelles," J. Nanosci. Nanotechnol., vol. 1 No. 3, pp. 2099-2104. 2015.

G. A. Husseini, M. A. Diaz de la Rosa, E. S. Richardson, D. A. Christensen, W.G. Pitt, "the role of cavitation in acoustically activated drug delivery," J. Control. Release, vol. 107, No. 2, pp. 253-261, 2005.

G. A. Husseini, W. G. Pitt, and A. M. Martins, "Ultrasonically triggered drug delivery: breaking the barrier," Colloids Surf B. Biointerfaces, vol. 123, pp. 364-386, Nov. 2014.

(56) References Cited

OTHER PUBLICATIONS

G. Blotny, "Recent applications of 2,4,6-trichloro-1,3,5-triazine and its derivatives in organic synthesis," Tetrahedron, vol. 62, No. 41, pp. 9507-9522, Oct. 2006.

G. Cevc and D. Marsh, "Phospholipid birayers physical principles and models.," Cell Biochem. Funct., vol. 6, No. 2 , pp. 147-148, Apr. 1988.

G. Gregoriadis, Ed. Liposome Technology: Entrapment of drugs and other materials into liposomes. Boca Raton: Taylor & Francis Group, 2007, p. 1-11.

G. P. Mishra, M. Bagui, V. Tamboli, and A. Mitra "Recent applications of liposomes in ophthalmic drugdelivery," Journal of Delivery, vol. 2011, pp. 1-14, 2011.

Graham, Susan M., et al. "Inertial cavitation to non-invasively trigger and monitor intratumoral release of drug from intravenously delivered liposomes." Journal of Controlled Release 178 (2014): 101-107.

H. Azhari, Basics of Biomedical Ultrasound for Engineers. New Jersey: John Wiley & Sons, 2010, p. 94-97.

H Baghirov, A Aslund, S Snipstad, S Berg, R Hansen, F Thorsen, Y Morch, C de Lange Davies. https://cancerres.aacrjournals.org/content/76/14_Supplement/2073 accessed Nov. 25, 2019, originally published Jul. 2016, pp. 1-5. (Year: 2016).

H. G. Flynn, "Physics of Acoustic Caviatiion," J Acoust. Soc. Am., vol. 31, No. 11, p. 1582, Nov. 1964.

H. G. Moussa, A. M. Martins, and G.A. Husseini, "Review of Triggered Liposomal Drug Delivery with a Focus on Ultrasound," Curr. Cancer Drug Targets, vol. 2, 2015.

H. Grull and S. Langereis, "Hyperthermia-triggered drug delivery from temperature-sensitive liposomes using. MRI-guided high intensity focused ultrasound.," J. Control. Release, vol. 161, No. 2, pp. 317-327, Jul. 2012.

H. Hatakeyama, H. Akita, K. Kogure, M. Oishi, Y. Nagasaki, Y. Kihira, M. Ueno, H. Kobayashi, H. Kikuchi, and H. Harashima, "Development of a novel systemic gene delivery system for cancer therapy with a tumor-s ecific cleavable PEG-lipid," Gene Ther., vol. 14, No. 1, p. 68-77, Jan. 2007.

H. Maeda, "The enhanced permeability and retention (EPR) effect in tumor vasculature: the key role of tumor-selective macromolecular drug targeting," Adv. Enzyme Regul., vol. 41, n . I, pp. 189-207, May 2001.

H. Maussa, "Liposomal Drug Release Using Ultrasound and Modeling Release Dynamics for Model Predictive Controller Design," M.S. Thesis, Electrical Eng. Dept., American University of Sharjah, UAE, 2015.

Hare, Jennifer I., Elaine H. Moase, and Theresa M. Allen. "Targeting combinations of liposomal drugs to tumor vasculature cells and tumor cells for the treatment of HER2-positive breast cancer." Journal of drug targeting 21.1 (2013): 87-96.

Husseini, Ghaleb A., et al. "Kinetics of ultrasonic release of doxorubicin from pluronic P105 micelles." Colloids and Surfaces B: Biointerfaces 24.3 (2002): 253-264.

I. Patel. (2011). Ceramic Based Intelligent Piezoelectric Energy Harvesting Device ' In Advances in Ceramics-Electric and Magnetic Ceramics, Biocersmics and Environment. [Online].

Ibrahim, Mihad, "Anti-Cancer Drug Delivery Using Metal Organic Frameworks (MOFs) and Ultrasound," retrived from internet https://dspace.aus.edu/xmlui/bitstream/handle/11073/8325/35.232-2016.17%20Mihad%20Ibrahim.pdf?sequence+1&isAllowed=y. on Jul. 19, 2021.

J. Connor, M. B. Yatvin, and L. Huang, "pH-sensitive liposomes: acid-induce liposome Fusion," proc. Natl. Acad. Sci., vol. 81, No. 6, pp. 1715-1718, Mar. 1 984.

J. Dua, A. Rana, and A.Bhandari, "Liposome: Methods of Preparation and Applications," Int. J. Pharrn. Stud. Res., vol. 3, No. 2, pp. 14-20, 2012.

J. Escoffre and A. Bouakaz. Therapeutic Ultrasound. Switzerland: Springer International, 2015, p. 278.

J. Kost, K. Leong, and R. Langer, "Ultrasonically controlled polymetric drug delivery," Die Makromol. Chemie, Macromol. Symp., vol. 285, pp. 275-285, 1988.

J. Lasch, Torchilin, Vladimir, and Volkmar Weissig, eds. Chapter 1: Preparation of Liposomes, Liposomes: a practical approach. No. 264. pp. 3-16 OxfordUniversity Press, 2003.

J. Lattin, W. G. Pitt, D. Bein and G. A. Husseini, "Ultraso/rid-induced Calcein Release Fromeliposomes," Ultrasound Med. Biol., vol. 38, No. 1 2, pp. 2163-2173, 2012.

J. R. Lattin, D. M. Belnap, and W.G. Pitt, "Formation of eLiposomes as a drug delivery vehicle,"Colloids Surf B. Biointerfaces, vol. 89, pp. 93-100, Jan. 2012.

J. T. Busher, "Serum Albumin and Globulin" in Clinic Methods: The History, Physical, and Laboratory Examinations, 3rd ed., H.J. Walker HK, Hall WD, Ed. Boston, 1990, pp. 497-499.

J. W. Nichols and Y. H. Bae, "EPR: Evidence and fallacy," J. Control. Release, vol. 190, pp. 451-464, Sep. 2014.

J. Wu and W. L. Nyborg, "Itrasound, cavitation bubbles and their interaction with cells.," Adv. Drug Deliv. Rev., vol. 60, No. 10, pp. 1103-1116, Jun. 2008.

J. Yokoe, S. Sakuragi, K. Yamamoto, Teragaki, K. Ogawara, K. Higaki, N. Katayama, T. Kai, M. Sato, and T. Kimura, "Albumin-conjugated PEG liposome enhances tumor distribution of liposomal doxorubicin in rats.," int. J Pharm., vol. 353, No. 1-2, pp. 28-34, Apr. 2008.

J.E. Ghadiali and M. M. Steve , "Enzyme-Responsive Nanoparticle Systems," Adv. Mater., vol. 20, No. 22, pp. 4359-4363, Nov. 20.

Jain, Ankitkumar S., et al. "Tamoxifen guided liposomes for targeting encapsulated anticancer agent to estrogen receptor positive breast cancer cells: in vitro and in vivo evaluation."Biomedicine & Pharmacotherapy 68.4 (2014): 429-438.

Jiang, Juan, et al "Sequential treatment of drug-resistant tumors with RGB-modified liposomes containing siRNA or doxorubicin." European Journal of Pharmaceutics and Biopharmaceutics 76.2 (2010): 170-178.

K. Furu moto, J.-I. Yokoe, K. Ogawara, S. Amano, M. Takaguchi, K. Higaki, T. Kai, and T. Kimura, "Effect of coupling of albumin onto surface of PEG liposome on its in vivo disposition" Int. J. Pharm., vol. 329, No. 1-2, pp. 110-116, Feb. 2007.

K. Jorgensen and O.G. Mouritsen, "Phase separation dynamics and lateral organization of two-component lipid membranes.," Biophys. J., vol. 69, No. 3, pp. 942-954, Sep. 19.

K. Lee, K. Hong, and D. Papahadjopoulos, "Recognition of liposomes by cells: In vitro binding and fendocytosis mediated by specific lipid headgroups and surface charge density," Biochim. Biophys.Acta—Biomembr., vol. 1103, No. 2, pp. 185-197, Jan. 1992.

K. Madaan, S. Kumar, N. Paonia, V. Lather, and D. Pandita, "Dendrirners in drug delivery and .targeting: Drug-dendrirner interactions and toxicity issues.," J. Pharm. Bioallied Sci., vol. 6, No. 3, pp. 139-150, Jul. 2014.

K. Maruyama "Targetability of novel immunoliposomes modified with amphipathic poly(ethylene glycol)s conjugated at their distal terminals to monoclonal antibodies," Biochim. Biophys. Acta—Biomembr. vol. 1234, No. 1, pp. 74-80, Mar. 1995.

K. P. Kumar, D. Bhowmik, and L. Deb, "Recent Trends in Liposomes Used As Novel Drug Delivery System" The Pharma Innovation International Journal, vol. 1, pp. 26-34, 2012.

K. S. Suslick, "Sonoluminescence and sonochemistry," in Ultrasonics Symposium, 1997. Proceedings., 1997 IEEE, vol. 1, pp. 523-532, Oct. 5-8, 1997.

K. W. Ferrara, "Driving delivery vehicles with ultrasound.," Adv. Drug Delv. Rev., vol. 60, No. 10, pp. 1097-1102, Jun. 2008.

Kastantin, Mark, et al. "Effect of the lipid chain melting transition on the stability of DSPE-PEG (2000) micelles." Langmuir 25.13 (2009): 7279-7286.

Kramer, John F. "Ultrasound: evaluation of its mechanical and thermal effects." Archives of physical medicineand rehabilitation 65.5 (1984): 223-227.

L. Bjornstrom and M. Sjoberg, "Mechanisms of Estrogen Receptor Signaling: Convergence of Genomic and Nongenomic Actions on Target Genes," Enocrine Soc., pp. 833-842, 2005.

L. Wang, J. H. Tay, S. Lee, and Y. T. Hung, Eds. Environmental Bioengineering. New York: Humana Press, 2010, p. 59.

(56) References Cited

OTHER PUBLICATIONS

Lee, "Felate-mediated tumor cell targeting of liposome entrapped doxorubicin in vitro," Biochim. Biophys. Acta, vol. 1233, pp. 134-144, 1995.

Lentacker, Ine, et al. "Understanding ultrasound in induced sonoporation: definitions and underlying mechanisms." Advanced drug delivery reviews 72 (2014): 49-64.

Li, Hua-Fei, et al. "Targeted and controlled Drug delivery using a temperature and ultra-violet responsive liposome with excellent breast cancer suppressing ability." RSC Advances 5.35 (2015): 630-27639.

Li, Jing-Liang, et al. "In vitro cancer cell imaging and therapy using transferrin-conjugated gold nanoparticles." cancer letters 274.2 (2009): 319-326.

M. Atadzi, C. D. Davies, Y. H. Hansen, T. Johansen, O.K Standel, R. Hansen, S.E. Masey, E. A Nilssen, and B. Angelsen, "Effects of ultrasound parameters on the release ofliposmal calcein," Ultrasound Med. Biol,, vol. 38, No. 3, pp. 476-486, Mar. 2012.

M. Basel, "Targeting Cancer Therapy: Using Protease Cleavage sequences to Develop More Selective and Effective Cancer Treatments." PHD Thesis, Kansas State University, USA, 2010.

M. C. Jain. Textbook of Engineering Physics, Part 2. New Delhi: PHI Learning Pvt. Ltd., 201O, pp. 238-241.

M. Derrick, D. Stulik, and J. Landry. Infrared spectroscopy in conservation science, vol. 53. Los Angeles: J. Paul Getty Trust, 1999, p. 28.

M. Fox, F. Szoka, an J. Frechet, "Soluble Polymer Carriers for treatment of cancer: The Importance of Molecular Architecture," Polymer Pharmacokinetics and Molecular Architecture, vol. 42, No. 8, pp. 1141-1151, 2009.

M. Grandolfo, and P. Vecchia. Ultrasound: Medical Applications, Biological Effects, and Hazard Potential. New York: Plenum Press, 1987, p. 13-19.

M. Hsu and J. RL. "Interactions of liposomes with the reticuloendothelial system. II; Nonspecific and receptor-mediated uptake of liposomes by mouse peritoneal macrophages.," Biochim. Biophys. Acta, vol. 720, No. 4, pp. 411-419, Sep. 1982.

M. J. Hawkins, P. Soon-Shiong, and N. Desai, "Protein nanoparticles as a drug carriers in clinical medicine.," Adv. Drug Deliv. Rev., vol. 60, No. 8, pp. 876-885, 2008.

M Keswani, S. Raghavan, and P. Deymier, "Characterization of transient cavitation in gas sparged solutions exposed to megasonic field using cyclic voltammetry," Microelectron. Eng., vol. 102, pp. 91- 97, Feb. 2013.

M. L. Immordino, F. Dosio, and L. Cattel, "Stealth liposomes: review of the basic science, rationale, and clinical applications, existing and potential," Int. J. Nanomedicine, vol. 1, No. 3, pp. 297-315, Jan. 2006.

M. Luconi, G. Forti, and E. Baldi, "Genomic and nongenomic effects of estrogens: molecular mechanisms of action and clinical implications for male reproduction," J Steroid Biochem. Mol. Biol. vol. 80, No. 4-5, pp. 369-381, Apr. 2002.

M. Margulis. Sonochemistry/Cavitation, Amsterdam: Gordon and Breach Science, 1995, pp. 310-311.

M. Margulis, Sonochemistry and Cavitation. Amsterdam: Gordon and Breach Science Publishers, 1995, p. 542-543.

M. Martins, S. Ahmed, R. F. Vitor and G.A. Husseini, "Ultrasonic Drug Delivery Using Micelles and Liposomes," in Handbook of Ultrasonics and Sonochemistry, M. Ashookkumar, Ed., Signpore, 2016, pp. 1-35.

M. Pong, S. Umchid,A. J. Guarino, P.A. Lewin, J. Litniewski, A. Nowicki, S. P. Wrenn, "In vitro ultrasound-mediatedd leakage from phospholipid vesicles," Ultrasonics, vol. 45, No. 1-4, pp. 133-145, Dec. 2006.

M. R. Mozafari, a Pardakhty, S. Azarmi, J. a Jazayeri, a Nokhodchi, and a Omri "Role of nanocarrier systems in cancer nanotherapy.," J. Liposome Res., vol. 19, No. 4, pp. 310-321, 2009.

M.A. Elkhodiry, C. C. Momah, S. R.. Suwaidi, D. Gadalla, A. M. Martins, R. F. Vitor, and G. A. Husseini, "Synergistic Nanomedicine.

Passive, Active, and Ultrasound-Triggered Drug Delivery in CancerTreatment," Journal of Nanoscience and Nanotechnology, vol. 15, pp. 1-19, 2015.

Martins, Ana M., et al. "Ultrasound-induced doxorubicin release from folate-targeted and non-targeted P105 micelles: a modeling study." European Journalof Nanomedicine 8.1 (2016): 17-29.

Monsuez, Jean-Jacques, et al. "Cardiac side-effects of cancer chemotherapy." International journal of cardiology 144.1 (2010): 3-15.

N. Monteiro, A. Martins, R. L. Reis, and N.M. Neves, "Liposomes in tissue engineering and regenerative medicine," J. R. Soc. Interface, vol. 11, No. 101, pp. 1-24, Oct. 2014.

N. Nasongkla, E. Bey, J. Ren, H. Ai, C. Khemtong, J. S. Guthi, S. Chin, A. D. Sherry, D. A. Boothman,and J. Gao, "Multifunctional Polymeric Micelles and cancer-Targeted, MRI-Ultrasensitive Drug Delivery Systems," Nano Lett., vol. 6, No. 11, pp. 2427-2430, 2006.

N. Rapoport, "Ultrasound-mediated misellar drug delivery" Int. J. Hyperth., vol. 28, No. 4, pp. 374-385, May 2012.

N. Rapoport, Z. Gao, and A. Kennedy, "Multifunctional nanoparticles for combining ultrasonic tumor imaging and targeted chemotherapy.," J Natl. Cancer Inst., vo I. 99, No. 14, pp. 1095-1106, Jul. 2007.

Nygren, Peter. "What is cancer chemotherapy?." Acta Oncologica 40.2-3 (2001): 166-174.

O. Gerasimov, J. Boomer, M.,,Qualls, and D. Thompson, Cytosolic drug delivery using pH- and light-sensitive liposomes. Adv. Drug Deliv. Rev. vol. 38. No. 3. pp. 317-338. Aug. 1999.

Oerlemans, Chris, et al. "Evidence for a new mechanism behind HIFU-triggered release from liposomes." Journal of controlled release 168.3 (2013): 327-333.

P. Allisy-Roberts and J. R. Williams. Farr's Physics for Medical Imaging. Philadelphia: Elsevier Health Sciences, 2008, p. 153-154.

P. E. Huber, J. W. Jenne, R. Rastert, I. Simiantonakis, H. Sinn, H. Strittmatter, D. Von Fournier, M. F. Wannenacher, and J.• Debus, "A New NoninvasiveApproach in Breast Cance Therapy UsingMagnetic esonance Imaging-guided Focused Ultrasound Surgery," Cancer Res., vol. 61, pp. 8441-8447, 2001.

P. Hoskins, A. Thrush, K. Martin, and T. Whittingam. Diagnostic Ultrasound: Physics and Equipment. London: Cambridge University Press, 2003, p. 196-214.

P.J. Photos, L. Bacakova, B. Discher, F. S. Bates, and D. E. Discher, "Polymer vesicles in vivo: correlations with PEG molecular weight," Journal of Controlled Release, vol. 90, No. 3, pp. 323-334, Jul. 2003.

PK Dubey, V Mishra, S Jain, S Mahor, SP Vyas. "Liposomes Modified with Cyclic RGD Peptide for Tumor Targeting." Journal of Drug Targeting, vol. 12(5), Jun. 2004, pp. 257-264. (Year: 2004).

P. Laugier and G. Haiat. Bone Quantitative Ultrasound, vol. 30. New York: Springer Science & Business Media, 2010, pp. 32-39.

P. R. Cullis, L. D. Mayer, M. B. Bally, T. D. Madden, and M. J. Hope, "Generating and loading of liposomal systems for drug-delivery applications," Adv. Drug Deliv. Rev., vol. 3, No. 3, pp. 267-282 May 1989.

Pitt, William G, and S Aaron Ross. "Ultrasound increases the rate of bacterial cell groth." Biotechnology progress vol. 19,3 (2003): 1038-44.

Q. Lin, G. Jiang, and K. Tong, "Dendrimers in Drug-Delivery Applications," Des. Monomers Polym., vol. 13, No. 4, pp. 301-324, Jun. 2010.

R. E. Apfel and C.K. Holland, "Gauging the likelihood of cavitation from short-pulse, low-duty cycle diagnostic ultra-sound," Ultrasound Med. Biol., vol. 17, No. 2, pp. 179-185, Jan. 1991.

R. K. Schlicher, H. Rad rishna, T. P. Tolentino, R. P. Apkarian, V. Zarnitsyn, and M. R. Prausnitz, "Mechanism of intracellular delivery by acoustic cavitation," Ultrasound Med. Biol., vol. 32, No. 6, pp. 915-924,Jun. 2006.

R. Lobo. Treatment of the Postmenopausal Woman: Basic and Clinical Aspects. (3rd edition). Chapter 53 Pharmacology of Estrogens, Academic Press, 2007, p. 767-777.

R. Siegel, D. Naishadham, and A. Jemal, "Cancer Statistics, 2012 ," CA. Cancer J. Clin., vol. 62, pp. 10-29, 2012.

R. Silva, H. Ferreira, C. Little, and A. Cavaco-Paulo, "Effect of ultrasound parameters for unilamellar liposome preparation.," Ultras Sonochem., v ol. 17, No. 3, pp. 628-632, Mar. 2010.

(56)          References Cited

OTHER PUBLICATIONS

R. Singh and J. W. Lillard, "Nanoparticle-based targeted drug delivery.," Exp. Mal. Pathol., vol. 86, No. 3, pp. 215-223, Jun. 2009.

Rapoport, Natalya, et al. "Focused ultrasound-mediated drug delivery to pancreatic cancer in a mouse model." Journal of therapeutic ultrasound 1.1 (2013): 11.

Reddy, Bathula S., and Rajkumar Banerrjee. "17B-Estradiol-Associated Stealth-Liposomal Delivery of Anticancer Gene to Breast Cancer Cells." Angewandte Chemle International Edition 44.41 (2005): 6723-6727.

S Ahmed. "Dynamics of Chemotherapeutic Drug Release from Liposome Using Low-Frequency Ultrasound." Masters Thesis, American University of Sharjah, Jan. 2015, pp. 1-101. (Year: 2015).

S. Ahmed, H. G. Mauss , A. M. Martins, M. Al-Sayah and G. A. Hassseini Effect of pH, ultrasound frequency and power density on the release of calcein from stealth liposomes, Eur. J. Nanomed., vol. 8, No. 1, pp. 31-43, 2016.

S. B. Stringham.M. Viskovska, E. S. Richardson, S. Ohmine, G. A. Husseini, B. K. Murray, and W.G. Pitt, "Over-Pressure Suppresses Ultrasonic-Induced Drug Uptake," Ultrasound Med. Biol., vol. 35, No. 3, pp. 409-415, Dec. 2014.

S. Barnett, "Thresholds for nonthermal bioeffects: theoretical and experimental basis for a threshold index", Ultrasound Med. Miol. 24 (1998) S41-S49.

S. Dreis, F Rothweiler, M. Michaelis, J. Cinatl, J. Kreuter, and K. Langer, "Preparation, characterisation and maintenance of drug efficacy of doxorubicin-loaded human serum albumin (HSA) nanoparticles.,"Int. J. Pharm., vol. 341, No. 1-2, pp. 207-214, Auq. 2007.

S Hernot, AL Klibanov. "Microbubbles in ultrasound-triggered drug and gene delivery." Advanced Drug Delivery Reviews, vol. 60, 2008, pp. 1153-1166. (Year: 2008).

S. Hauert and S. N. Bhatia, "Mechanisms of cooperation in cancer nanomedicine: towardss systems nanotechnology," Trends Biotechnol., vol. 32, No. 9, pp. 448-455, Jul. 2014.

S. Huang and R. C. MacDonald, "Acoustically active liposomes for drug encapsulation and ultrasound-triggered release.," Biochim. Biophys. Acta, vol. 1665, No. 1-2, pp. 134-141, Oct. 2004.

S. Jang, M. Wientjes, D. Lu, and J. Au, "Drug delivery and transport to solid tumors," Pharm. Res. vol. 20, No. 6, pp. 1337-1350, 2003.

S. L. Huang , "Liposomes in ultrasonic drug and gene delivery," Adv. Drug Deliv. Rev, vol. 60, No. 10 pp. 1167-1176. Jul. 2008.

S. N. Sen. Acoustics, Waves and Oscillations. New Delhi: New Age International, 1990, p. 204.

S. Rai, R Paliwal, B. Vaidya, P. Gupta, S. Mahar, K. Khatri, A. Goyal,. A. Rawat, and S.P. Vyas, "Estrogen(s) and Analogs as a NonImmunogenic Endogenous Ligand in Targeted Drug/DNA Deliver,"Curr. Med. Chem., vol. 14, No. 19, pp. 2095-2109, Aug. 2007.

S. Sarkar, S. Ali, L. Reh mann, G. Nakhla, and M. B. Ray, "Degredation of estrone in water and wastewater by various advanced oxidation processes," J Hazard. Mater., vol. 278, pp. 16-24, Aug. 2014.

S. Stewart, K. Harrington, and M.Harrington, "The Biodistribution and Pharmacokinetics of Stealth Lioposomes in Patients with Solid Tumors." Oncoloav. Oct. 1997.

S. Venkataraman, J. L. Hedrick, Z. Y. Org, C.Yang P. L. R. Ee, P. T. Hammond, and Y. Y. Yang, "The effects of polymeric nano structure shape on drug delivery," Advanced Drug Delivery, vol. 63, No. 14-15. pp. 1228-45 . Nov. 2011.

Shivani, et al. "Targeted delivery of doxorubioin via estrone-appended liposomes." Journal of drug targeting, (2008) 455-463.

Shroff, Kamlesh, and Efrosini Kokkoli. "PEGyatedl liposomal doxorubicin targeted to a5B1-expressing MDA-MB-231 breast cancer cells," Langmuir 28.10 (2012): 4729-4736.

Stewart, John Charles Marshall. "Colormetric determination of phospholipids with ammonium ferrothiocyanate." Analytical biochemistry 104.1 (1980): 10-14.

SR Paliwal, R Paliwal, N Mishra, A Mehta, SP Vyas. "A Novel Cancer Targeting Approach Based on Estrone Anchored Stealth Liposome for Site-Specific Breast Cancer Therapy." Current Cancer Drug Targets, vol. 10, 2010, pp. 343-353. (Year: 2010).

T. A. Greenhalgh and R P. Symonds, "Principles of chemotherapy and radiotherapy," Obstet. Gynaecol. Reprod . Med., vol. 24, No. 9, pp. 259-265, Sep. 2014.

T. Boyer, D. Zakim, and D. Vessey "Direct, Rapid Transfer of Estrone from Liposomes to Microsomes," J.Biol. Chem., vol. 255, pp. 627-631, 1980.

T. Evjen, "Sonosensitive liposomes for ultrasound-mediated drug delivery," PHD Thesis, Department of pharmacy, University of Tromso, Norway, 2011.

T. Ishida and H. Kiwada Accelerated blood clearance (ABC) phenomenon upon repeated injection of PEGylate, liposomes, Int. J. Pharm., vol. 354, No. 1-2, pp. 56-62, May 2008.

T. J. Evjen, E.A. Nilssen, S. Barnert, R. Schubert, M. Brandi, and S. L. Fessheim, "Ultrasound-mediated destabilization and drug release from liposomes comprising dioleoylphosphatidylethanolamine," Eur. J. Pharm. Sci., vol. 42, No. 4, pp. 380-386, 2011.

T. J. Evjer., E. Hagtvet, A. Moussatov, S. ROgnvaldsson, J.-L. Mestas, R. A. Fowler , C. Lafon, and E. a Nilssen, "In vivo monitoring of liposomal release in tumours following ultrasound stimulation," Eur. J. Pharm. Biopharm. vol. 84. No. 3. DD. 526-531. Aug. 2013.

T. J. Evjen, S. Hupfeld, S. Barnert, S. Fossheim, R. Schubert, and M. Brandl, "Physiochemical characterization of liposomes after ultrasound exposure—mechanisms of drug release.," Pharm. Biomed. Anal.. vol. 78-79. pp. 118-122. May 2013.

T. Lammers, F. Kiessling, W. E. Hennink, and G. Storm, "Drug targeting to tumors: principles, pitfallsand (pre-) clinical progress.," J. Control. Release, vol. 161, No. 2, pp. 175-187, Jul. 2012.

T. M. Allen, C. Hansen, F. Martin, C. Redemann, and A. Yau-Young, "Liposomes containing synthetic lipid deriviatives of poly (ethylene glycol) show prolonged circulation half-lives in vivo," Biochim. Biophys. Acta, vol. 1066, No. 1, pp. 29-36, Jul. 1991.

T. Yu, S Li, J Zhao, TJ Mason. "Ultrasound: A Chemotherapy Sensitizer." Technology in Cancer Research and Treatment, vol. 5 No. 1, Feb. 2006, pp. 51-60. (Year: 2006).

Tachibana, Katsur o, et al. "Induction of cell-membrane porosity by ultrasound," The Lancet 353.9162 (1999): 1409.

Tanbour, Rafeeq, et al. "Drug delivery systems based on polymeric micel less and ultrasound: a review." current pharmaceutical design 22.19 (2016): 2796 -2807.

V. Frenkel, "Ultrasound mediated delivery of drugs and genes to solid tumors.," Adv. Drug Deliv. Rev. vol. 60, No. 10, pp. 1193-1208, Jun. 2008.

V. Gibbs, D. Cole, and A. Sassano. Ultrasound Physics and Technology: How, Why and When. Elsevier Health Sciences, 2009, p. 21-22.

V. P. Torchilin, "p -Nitrophenyloarbonyl-PEG-PE-liposomes: fast and simple attachment of speci ¢ c ligands, including monoclonal antibodies, to distal ends of PEG chains via p-nitrophenylcarbonyl groups," Biochim Biophys. Acta, vol. 1 5111, pp. 397-411, 2001.

V. P. Torchilin, "Passive and Active Drug Targeting: Drug Delivery to Tumors as an Example" in Drug Delivery, vol. 197. M. Schafer-Korting, ED. Boston: Springer Berlin Heidelberg, Nov. 2010, pp. 3-53.

V. P. Torchilin, "Strategies and Means for Drug Targetiing: An Overview," in Biomedical Aspects of Drug Targeting, V. Muzykantov and V. Torchillin, Eds. Springer New York, 2002, pp. 3-26.

V. Singh and M. Shriwastava, "Ultrasonic Hyperthermia for Cancer Treatment," Natl. Phys. Lab., vol. 43, No. 3, pp. 235-241, 1993.

V. Torchilin. Multifunctional Pharmaceutical Nanocarriers. New York: Springer Science & Business Media, 2008, p. 7.

V. Torchilin, "Multifunctional and Stimul-Sensitive pharmaceutical Nanocarriers.," Eur J PharmBiopharm, vol. 71, No. 3, pp. 431-441, 2009.

Veneti, Eleftheria, Raymond S. Tu, and Debra T. Auguste. RGD-targeted liposome binding and uptake on breast cancer cells is dependent on elastin linker secondary structure. Bioconjugate Chem 27.8 (2016): 1813-1821.

W. B. McNamara III,. lii, Y. T. Didenko, and K. S. Suslick, "Sonoluminescence temperatures during multi-bubble cavitation," Nature, vol. 401, pp. 772-775 Oct. 1999.

(56)  References Cited

OTHER PUBLICATIONS

W. C. Dewey, "Arrhenius relationships from the molecule and cell to the clinic.," Int. J Hyperthermia, vol. 25, No. 1, pp. 3-20, Feb. 2009.

W. G. Pitt and S. A Ross, "Ultrasound increases the rate of bacterial cell growth," Biotechnol. Prag., vol. 19, No. 3, pp. 1038-1044, 2003.

W. G. Pitt, G. A Husseini, and B. J. Staples, "Ultrasonic drug delivery—a general review.," Expert Opin.Drug Deliv., vol. 1, No. 1, pp. 37-56, Nov. 2004.

W. G. Pitt, G.A. Husseini, and L. N. Kherbeck, "Ultrasound-triggered Release from Micelles," in Smart Materials for Drug Delivery, vol. 1, No. 2, C. Lorenzo and A. Concheiro, Eds. The Royal City ofChemistry , 2013, pp. 148-178.

W. G. Pitt, G. A. Husseini, B. L. Roeder, D. J. Dickinson, D.R. Warden, J.M. Hartley, and P. W. Jones, "Preliminary Results of Combining Low Frequency Low Intensity Ultrasound and Liposomal Drug delivery to Treat Tumors in Rats," J. Nanosci. Nanotechnol., vol. 11, No. 3, pp. 1866-1870, Mar. 2011.

Wu, Jun, et al. "Reversal of multidrug resistance by transferrin-conjugated liposomes co-encapsulating doxorubicin and verapamil." J Pharm Pharm Sci 10.3 (2007): 350-357.

X. Wang, T. Ishida, and H. Kiwada, "Anti-PEG IgM elicited by injection of liposomes is involved in the enhanced blood clearance of a subsequent dose of PEGylated liposomes," J. Control. Release, vol. 119, No. 2, pp. 236-244, Jun. 2007.

X. Y. Wang, T. Ishida, M. Ichihara, and H. Kiwada, "Influence of the physicomemical properties of liposomes on the accelerated blood clearance phenomenon in rats," J. Conrol. Release, vol. 104, No. 1, pp. 91-102, May 2005.

Y. P. Patil and S. Jadhav. "Novel methods for liposome preparation. ," Chem. Phys. Lipids, vol. 177, pp. 8-18, Jan. 2014.

Y. Yeo, Ed. Nanoparticulate Drug Delivery Systems: Strategies, Technologies, and Applications. New Jersey: John Wiley & Sons, 2013.

Z. Mirafzali, "Is it necessary to add cholesterol to a liposome formulation?—Quora." [Online]. Available: https://www.quora.com/ls-it-necessary-to-add-cholesterol- to-a-liposome-formulation, 2011 [Accessed:Apr. 4, 2017].

Z. Song, Zhiwang, et al. "Cyclic RGD peptide-modified liposomal drug delivery system for oral apatnib administration: enhanced cellular uptake and improved therapeutic effects." International journal of nanomedicine 12:(2017): 1941-58.

Z. Xu, H. M. Davis, and H. Zhou, "Rational development and utilization of antibody-based therapeuticproteins in pediatrics," Pharmacol_ Ther., vol. 137, No. 2,pp. 225-247, Mar. 2013.

* cited by examiner

SYSTEMS AND METHODS FOR TARGETED BREAST CANCER THERAPIES

CROSS-REFERENCE TO RELATED APPLICATIONS

This application is a continuation of U.S. patent application Ser. No. 17/119,001, filed on Dec. 11, 2020, which is a continuation of U.S. patent application Ser. No. 16/159,550, filed on Oct. 12, 2018, which claims priority to U.S. Provisional Patent Application No. 62/572,358, filed on Oct. 13, 2017, which is hereby incorporated by reference in its entirety and should be considered a part of this specification.

BACKGROUND

Field

The present application relates generally to systems and methods for producing acoustically activated or triggered nanoparticles and more specifically, relates to systems and methods for producing and using acoustically activated or triggered, ligand-targeted liposomes for the novel treatment of cancer.

Description of the Related Art

Cancer is a wide-spread disease, and the most common types (responsible for more than half of all cases) are breast, prostate, lung, and colon cancers. By far the most common cancer in women and the second leading cause of cancer death among American women is breast cancer. It is also a global concern that endangers women's lives worldwide. Breast cancer is the most frequent cancer in women and the second overall. Of the 4.4 million new breast cancer cases diagnosed within the past five years, only 1.4 million have survived.

In recent years, there have been several ways to treat cancer depending on the type of malignancy, stage, and pathologic features such as receptor status and tumor grade. A plan for each patient depends on the purpose of treatment, either to shrink the tumor, stop the tumor growth, or just enhance the patient's quality of life in late stages. Treatments include surgery, radiation, chemotherapy, biological therapy (including immunotherapy), and targeted therapy. It can also be a combination of the above treatments. In the early stages before the metastasis of cancer, surgery combined with radiation (localized treatments) may be applied. But in later stages, chemotherapy may be used, sometimes in combination with biological therapy, such as immunotherapy. Adjuvant treatment may be then followed to make sure that new tumors are eliminated.

SUMMARY

In some embodiments, a method of treating breast cancer in a mammal comprises: delivering an actively targeted liposome to the mammal, allowing the actively targeted liposome to circulate throughout a circulatory system of the mammal for a time sufficient to allow aggregation of a therapeutic quantity of actively targeted liposomes at a treatment area comprising a breast cancer; and applying ultrasound to the treatment area such that the actively targeted liposome is critically disrupted thereby releasing the chemotherapeutic drug in the treatment area. The actively targeted liposome comprises: a lipid bilayer forming a spherical shell comprising an interior liposomal cavity;

a plurality of trastuzumab molecules linked to a surface of the actively targeted liposome; and a chemotherapeutic drug comprising at least one of a hydrophilic chemotherapeutic drug contained within the interior liposomal cavity and a hydrophobic chemotherapeutic drug contained within the lipid bilayer of the actively targeted liposome.

The ultrasound applied to the treatment area may comprise a low frequency ultrasound. The low frequency ultrasound may comprise a 20 kHz with a power density of one of 7.46 W/cm2, 9.85 W/cm2, and 17.31 W/cm2. The low frequency ultrasound applied to the treatment area may be applied for less than about 6 minutes. The ultrasound applied to the treatment area may comprise high frequency ultrasound. Pulsed ultrasound may be applied to the treatment area. The ultrasound may be pulsed 2 times or 3 times. The lipid bilayer of the actively targeted liposome may comprise one or more PEGylated lipids. The plurality of trastuzumab molecules may be linked to a distal end of the PEG chain. The actively targeted liposome may comprise a protein density of 7.5-30 molecules per liposome. The actively targeted liposome may comprise a mean radius between 50-150 nm. The actively targeted liposome may comprise 6 to 12 trastuzumab molecules. The chemotherapeutic drug may comprise calcein. The chemotherapeutic drug may be selected from the group of doxorubicin, annamycin, daunorubicin, vincristine, cisplatin derivatives, paclitaxel 5-fluorouracil derivatives, camptothecin derivatives, and retinoids. The actively targeted liposome may be comprises a plurality of vesicles, the plurality of vesicles linked to about 9 trastuzumab molecules. The plurality of trastuzumab molecules may be linked to the surface of the actively targeted liposome using cyanuric chloride.

DETAILED DESCRIPTION

Cancer

Figure 1:
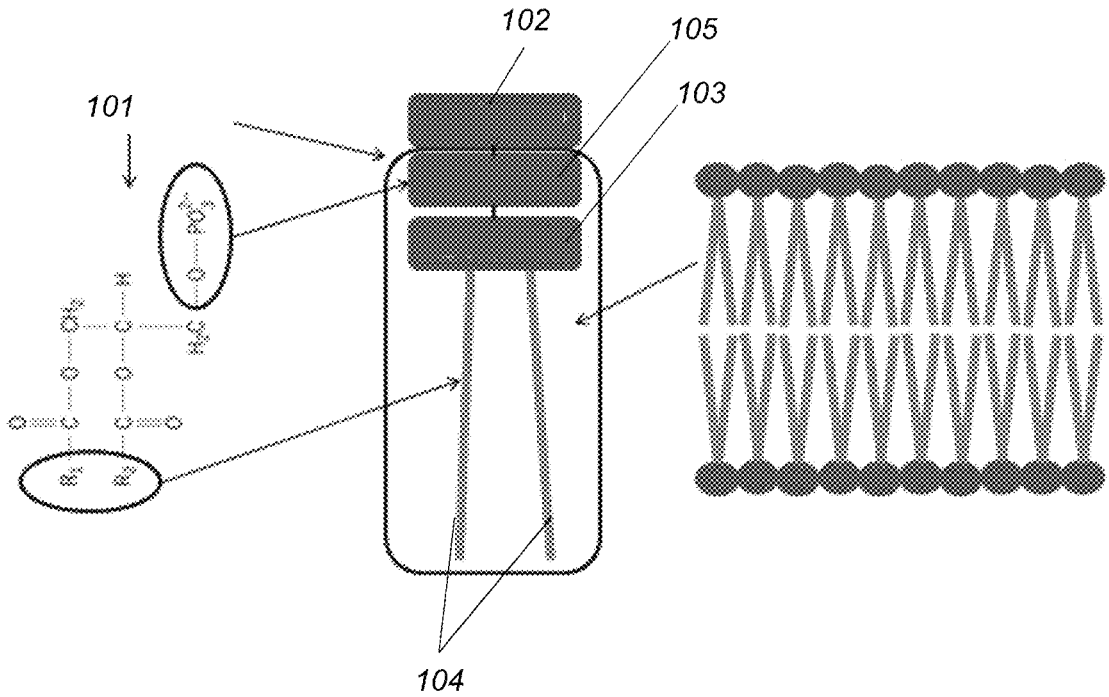
FIG. 1 illustrates a schematic view of molecule structure of phosphoglyceride.

Most normal cells replicate, but tumor cells are damaged cells that cannot stop growing, such that they can escape programmed cell death (apoptosis); due to abnormalities in cell proliferation, differentiation, and survival. These cells are either benign or malignant. Malignant cells (cancer) usually proliferate faster and spread throughout the body invading other organs. Solid tumors that stem from cells of mesenchymal origin (connective tissue) are known as sarcomas, and they spread via the blood stream. Cancer cells that arise from epithelial cells are called carcinomas, they are the most common type of human cancer, and they spread through the lymphatic channels. Leukemia and lymphomas arise from the cells of the blood and the immune system respectively.

The tumor starts from a single cell that mutates. Mutations include activation of oncogenes that promote cell proliferation and damage in tumor suppressor genes that causes cell failure to differentiate normally. It proliferates fast requiring extensive blood vessels and nutrients during proliferation. After that, these cells form a cluster, and in that stage, it is called in situ carcinoma. Then they penetrate the basement membrane (extracellular matrix of tissue) to invade the underlying connective tissue. Once this happens, cancer cells can circulate throughout the body and spread the tumor to other organs, in a process called metastasis, and cause metastatic cancers. Metastasis is the main reason why localized therapy eventually does not work in cancer treatment. Furthermore, dissolution of the basement membrane tissue makes it permeable and easy to penetrate, which is considered a characteristic of the tumor tissue.

Apoptosis contributes to the development of the tumor and also creates resistance to chemotherapeutic drugs that are based on damaging the DNA. Normal cells proliferate in the presence of growth factors, this condition is determined by the density of the tissue, but cancer cells are insensitive to such signals; which can be due to the unregulated activity of growth factors receptors and intracellular signaling systems. Therefore, in general, cancer cells have a reduced requirement for growth factors. Some cancer cells produce their own growth factors, auto-stimulating cell division (autocrine signaling). Cancer cells are less responsive to cell-cell interactions, so there is less adhesion to other cells which makes them rounder. This also plays a role in their disordered multilayered growth patterns in which they push neighboring cells to grow, and eventually put pressure on the organ. They secrete chemicals that digest extracellular matrix components allowing for more invasions. They also produce growth factors that stimulate angiogenesis which results in the formation of new capillaries around the tumor.

It can also help in metastasis since these capillaries are easy to penetrate by cancer cells. Divided cells lose the capacity to differentiate. Cancer cells fail to respond to signals promoting apoptosis, contributing to the survival of damaged mutated cells. Some cancer cells produce immunosuppressive factors in an attempt to avoid detection by the immune system. Lower pH around the tumor is caused by lactic acid formation due to the lack of oxygen which is a result of a higher oxygen consumption rate in proliferation (higher than what angiogenesis can provide). This also contributes to immune system evasion where high lactic levels disturb T cells function.

Cancer progresses through a series of abnormalities that accumulate over time, so there can be several factors that induce cancer including carcinogens. Carcinogens include environmental factors, chemicals, radiations, and viruses. Factors that contribute to the proliferation of the mutated cells are called tumor promoters, they include increased accumulation of hormones and/or collagen.

HER2 Overexpression

Breast cancer is the most frequent cancer in women and the second overall. Breast cancer most commonly spreads to the regional lymph nodes, and in advanced stages, it could also spread to the bones, lungs, and liver. Some factors that may increase the risk of breast cancer are early menarche, late menopause, as well as obesity and increased uptake of alcohol. Breast cancer is known to develop as a result of a series of changes in oncogenes and cell mutations that include mutations in BRAC1 and BRAC2 genes. These two genes are tumor suppressor genes that help repair DNA damage. Mutations of these genes are present in basal breast cancers (triple negative breast cancer i.e. those that are HER2 negative, ER-negative and PR negative), and they may account for 20-25% of heredity breast cancers and 5-10% of all breast cancers.

Local estrogen production is also known to facilitate the growth of both cancer cells and breast stromal cells. Some breast cancer cells, sometimes referred to as "hormone receptor positive" breast cancers, differentially express estrogen and progesterone receptors compared to normal breast tissue. This type of cancer occurs most commonly in older patients and progresses slowly, and is expressed in up to 60% of breast tumors and can be treated with tamoxifen (an estrogen antagonist). Vascular endothelial growth factor receptors (VEGFR) are overexpressed in most cancer cells including breast cancer. They are essential for angiogenesis which is in turn required for cancer growth, invasion, and metastasis. Insulin-like growth factor receptors are also expressed in high levels in breast cancer compared with normal breast tissue. Lastly, another important family of receptors that regulate cell proliferation and apoptosis are the human epidermal growth factors family that includes HER1 (EGFR), HER2 (ErbB2), HER3 (ErbB3), and HER4 (ErbB4) that belong to a family of transmembrane receptor tyrosine kinases (RTKs).

HER2 encodes 1225 amino acids, and it is normally expressed at low levels in the epithelial cells of various organs such as the lung, bladder, pancreas, breast, and prostate. HER2 overexpression occurs in 20% to 30% of patients with breast cancer, and it is more spread among younger woman. HER-2 positive cancer progresses rapidly; hence coincides with decreased survival rates, with 20% less survival rate for HER-2 positive women than a HER-2 negative woman in the five year period following surgery. It is noteworthy that HER2 overexpression in breast cancer cells corresponds to overexpression of VEGF, and thus inducing angiogenesis. HER2 does not have a known ligand (orphan receptor) but it heterodimers with other receptors in the family to enhance signaling. Overexpression or gene amplification of HER2 induces ligand-independent homodimerization, hence the activation of HER2 signaling pathways that include PI3K/AKT and RAS/RAF/MAPK pathways which lead to cell proliferation, growth and survival as well as invasion and angiogenesis, and therefore cancer development. The HER family of receptors bind to a variety of different ligands as shown Table 1. It was found that prolidase (peptidase D) may act as a ligand for HER2 and inhibit downstream signaling using immunoprecipitation. Additionally, mutations in the PI3KCA gene have been detected in 25% of breast cancers. Table 1 also shows that HER-2 positive tumors tend to include P53 tumor suppressor gene mutation.

TABLE 1

Ligands of the human epidermal growth factors (HER) family

| Ligand | HER1 (EGFR) | HER2 | HER3 | HER4 |
|---|---|---|---|---|
| Transforming Growth Factor alpha (TGFα) | yes | — | — | — |
| Amphiregulin (AR, AREG) | yes | — | — | — |
| Epidermal Growth Factor (EGF) | yes | — | — | — |
| Betacellulin (BTC) | yes | — | — | yes |
| Heparin-binding EGF like Growth Factor (HBEGF) | yes | — | — | yes |
| Epigen (EPG) | yes | — | — | — |
| Epiregulin (EPR) | yes | — | — | yes |
| Heregulin | — | — | 1, 2 | 1, 2, 3, 4 |

Treatments of Cancer

In recent years, there have been several ways to treat cancer depending on the type of malignancy, stage, and pathologic features such as receptor status and tumor grade. A plan for each patient may depend on the purpose of treatment, either to shrink the tumor, stop the tumor growth, or just enhance the patient's quality of life in late stages. Cancer treatments may include surgery, radiation, chemotherapy, biological therapy (includes immunotherapy), and targeted therapy. It can also be a combination of these treatments. In the early stages before the metastasis of cancer, surgery combined with radiation (localized treatments) can be applied. In later stages, chemotherapy and/or immunotherapy may be used. Adjuvant treatment may be then followed to make sure that tumors are eliminated. Sometimes chemotherapy may be used before surgery in order to shrink the tumor size.

In chemotherapy, drugs are used to inhibit cell division and/or eventually kill them. Nitrogen mustard was the first chemotherapeutic agent to be used against cancer. It targets fast proliferating cells which unfortunately include some other normal cells as well (i.e. stems cells). Folic acid antagonists are the second group developed and are used to inhibit the cancer cell ability to produce folic acid which may be necessary for growth. Nucleic acid antagonists are the third group used. They are used to inhibit nucleic acid which is also needed for cell growth and proliferation. Tyrosine kinase inhibitors work by deactivating this protein which is responsible for facilitating signaling pathways related to cell proliferation activities. And antitumor antibiotics such as doxorubicin are also used in cancer treatment.

In some instances, the challenge of using chemotherapy may reside within the non-selective action resulting in the severe side effects of these chemical agents to normal cells which limit the dosage given in therapy. These side effects may include nausea, vomiting, diarrhea, anemia, and hair loss. They can also cause damage to the heart, the kidneys, and the bone marrow and may result in the death of the patient in some cases.

Another challenge can be the ability of the tumor to develop resistance to the antineoplastic drug, rendering them ineffective in the fight against malignant tissues. In drug resistance (also known as multi-drug resistance-MDR), the cancer cells may develop a mechanism that reduces the ability of cancer cells to take up the chemical agents, or reduce expression of some proteins that guide the agent to the cell. An additional MDR mechanism may be developed when the tumor is grown and some cells slow their proliferation, and hence become non-detectable as malignant cells. The heterogeneous tumor consists of cells with different characteristics and different sensitivity to chemotherapy; therefore they become drug resistant. As most chemotherapy drugs induce cancer cells apoptosis, defective apoptosis allows the survival of these cells, and make them resistant in the process.

To overcome MDR, a combination of drugs is generally used. MDR can be treated by the administration of a combination of drugs that follow different cytotoxic mechanisms, increasing the drug dosage, using chemotherapy with a combination of other therapies (immunotherapy), hyperthermia therapy, or delivering the drug more efficiently using advanced drug delivery systems. Hyperthermia therapy works by heating the tumor region above 40° C., a temperature at which cancer cells and tissue are rendered more porous, hence increases the uptake of the drug. It also facilitates the delivery of the drug as a result of dilated blood vessels to the tumor. Hyperthermia therapy can also be used in combination with radiation therapy.

In some instances, biological therapy may be used, alone or in combination with other therapies to treat cancer. Biological therapy includes: inducing the host defense (immunotherapy), inhibiting tumor growth, and/or prompting cell differentiation (remission). Cell differentiation is coupled with cell division, in such a way that whenever a cell is matured and fully differentiated it stops replicating/ dividing. Inhibiting tumor growth may work by inhibiting angiogenesis that provides nutrients needed for proliferation. This can be accomplished by blocking growth factors receptors signals to prevent tumor development.

Generally, the immune system recognizes pathogenic infections and abnormal or malfunctioning cells and destroys them. There are several types of immunotherapy including adoptive, passive and active immunotherapy. Adoptive immunotherapy is based on transferring white blood cells into the host. First tumor-sensitive white blood cells (cytotoxic T-cells) may be taken from the tumor area and grown in the laboratory to a large number, and then activated against the tumor-associated antigen (TAA) and injected back to help the host immune system fight cancer. The transplantation of the bone marrow could also be considered as adoptive immunotherapy. Non-specific active immunotherapy aims to boost the immune system in general by stimulating macrophages, lymphocytes, and natural killer cells.

In active immunotherapy, cells of a specific tumor can be altered to be more antigenic (provoking to the immune system) to help identify the tumor and produce designed antibodies for that tumor. This has led to the development of hybrid white blood cells that are cultured in laboratories to be used as factories for producing one specific type of antibodies (monoclonal antibodies).

Passive immunotherapy takes advantage of the development of monoclonal antibodies (mAb) and uses it to produce large quantities of monoclonal antibodies and transferring them into patients. Antibodies are proteins that bind to antigens expressed on the cancer cell surface marking them for the destruction by macrophages. Some monoclonal antibodies work mainly by attaching to and blocking antigens on cancer cells. These antigens help cancer cells grow and spread. One example is the use of trastuzumab (Herceptin) in blocking human epidermal receptor two protein (HER2), a receptor extensively overexpressed in breast cancer cells. Another example is the use of bevacizumab in targeting vascular endothelial growth factor VEGF receptor (that is necessary for angiogenesis), and cetuximab that binds the epidermal growth factor receptor (EGFR or HER-1).

Some monoclonal antibodies are also used in blocking immune checkpoints created by cancer cells in an attempt to avoid detection by the immune system. This works by binding the antibody to the cytotoxic T-lymphocyte associated antigen (CTLA4) receptor on the T-cells of the immune system. The CTLA4 receptor functions are opposite to the CD28 receptor that activates the attack against cancer cells. These receptors work on antigens CD80 and CD86 expressed on the cancer cell. Other ligands normally found in cancer cells are programmed death ligand 1 (PD-L1) that binds to a PD-1 checkpoint protein on T-cells and prevent them from attacking the cancer cell.

Targeted Therapy

One way to achieve more selective cancer treatment is the development of drugs that target specific receptors expressed on the surface of cancer cells. Normally targets include receptors that play a role in cell growth and survival, and that are overexpressed only or mostly on cancer cells rather than healthy ones. Targets can also include fusion genes that result from abnormalities in chromosomes.

Receptors are proteins that help cells regulate their processes. Surface receptors are proteins that span the cell membrane and are exposed from both sides. The extracellular domain, the transmembrane protein, and the intracellular domain transfer signals through initiating chain reactions using other intracellular proteins to form intracellular pathways to the target inside the cell, usually the nucleus. Intracellular receptors are proteins located in the cytosol or nucleus. Receptors that mediate cell interactions are called cell adhesion molecules in which they include: the selectins, the integrins, the immunoglobulin (Ig) superfamily, and the cadherins. Each receptor may be activated by binding to its specific ligand. Ligands are signaling molecules that transmit information between cells. They include ions, hormones, neurotransmitters, peptides, and growth factors. Targeted therapy can work by interfering with the functions of targets, using monoclonal antibodies for surface targets (transmembrane receptors), and small molecules for intracellular targets (usually enzymes proteins or transcription factors).

In contrast to chemotherapy that works by killing cells as a result of cytotoxic effects, targeted therapy is based on cytostatic effects (blocking proliferation). Monoclonal antibodies can also be used as conjugates guiding chemotherapy agents to the cell, or with radio-isotopes to focus radiotherapy on cancer cells.

There may be some challenges in implementing targeted therapy. The challenge may lie within identifying the target and what kind of ligands does it respond to, and developing an agent that interacts solely with that target. Developing resistance in which the cell mutates and stops responding to the drug can be another challenge. Another major challenge is related to monoclonal antibodies; in which creating humanized monoclonal antibodies is still a challenge but necessary because human mouse monoclonal antibodies can sometimes induce allergic reactions.

To overcome the challenges in cancer treatment (discussed in the previous sections) including severe side effects, and limited dosage and drug resistance, developing new strategies of drug delivery such as drug delivery systems may be needed. Drug delivery systems may be enable the usage of higher doses and to target cancer cells effectively without harming the healthy surrounding ones.

Drug Delivery Systems

Drug Delivery systems control the rate at which a drug is released and the location in the body where it is released, hence subsequently controlling the therapeutic agent infusion rate and required tissue drug levels. Some systems can control both. They not only improve safety and efficacy, but also permit new therapies that once were considered too risky or toxic to deliver by conventional ways. Release patterns can affect the therapeutic response significantly. Additionally, it can be more economical to enhance drug delivery systems than it would be to treat the side effects associated with the conventional chemotherapy. Drug Delivery Systems can include: mechanical pumps (implants), polymer matrices (micro-particulates), externally applied transdermal patches, drug delivery vehicles, and/or combination thereof.

Nanoparticles such as liposomes and macromolecular drug carriers such as polymers are classified as nanomedicines/nanocarriers, a field encompassing nanoscale drug delivery devices and aiming at optimizing selectivity, prolonging the agent's activity and controlling drug release and cellular uptake. The advantages of this technology are its ability to cross physiologic barriers, overcome drug resistance, and significantly reduce side effects. The small size of nanocarriers may help them leave the vascular system and extravasate at the tumor sites. It has also raised the possibility for intracellular targeting and gene delivery.

In embodiments, nanocarriers have the ability to passively target tumor cells by utilizing the enhanced permeability and retention (EPR) effect, which are discussed further in details elsewhere in this specification. Additionally, nanocarriers can be actively targeted utilizing the ligand-receptor by attaching different moieties on their surface. As a result, they have increased selectivity for tumors in general, and can make tumor specifically targeted. After reaching the tumor site, nanocarriers can be triggered to release their contents faster.

Triggering nanocarriers internally can be achieved via several stimulators such as change in pH, temperature, pressure, or enzymes concentration. Otherwise, nanocarriers can be triggered externally by light, magnetic or electric fields, and ultrasound.

In embodiments, nanocarriers may have a size range of about: 10-800 nm, 200-600 nm, 300-500 nm, or 400 nm. In some embodiments, nanocarriers include nanocrystals (quantum dots), nanosuspensions, nanotubes, nanowires, micelles, liposomes, metal-organic frameworks (MOFs), ceramic nanoparticles, dendrimers, solid lipid nanoparticles, and hydrogel nanoparticles. Micelles and liposomes are the most widely applicable nanocarriers.

Dendrimers are highly branched mono-dispersed macromolecules with a symmetric structure that may range in size from about: 1 to 20 nm, 2-18 nm, 3-15 nm, 4-12 nm, or 8-10 nm. Dendrimers contain nanocavities that are well suited for drugs encapsulation, and terminal functional groups that determine their solubility and chemical activity. By choosing different branching units and surface groups, properties of dendrimers can be altered. The diversity of structural components that can be used, provide them with distinctive physical and chemical properties. In contrast, toxicity and rapid clearance of dendrimers may limit their applications in drug delivery if not solved.

Micelles are composed of amphiphilic molecules that assemble spontaneously in water to form a lipid layer with a hydrophobic core that can entrap poorly soluble drugs and a hydrophilic tail that is in equilibrium with the aqueous surrounding. Micelles are relatively small with a diameter range of about: 10 to 100 nm, 20 to 90 nm, 30-80 nm, 40-70 nm, or 50-60 nm. that helps in deep tumor penetration but can still escape renal excretion. They are considered biocompatible meaning they are non-toxic to the human body. Micelles can be engineered towards more efficient drug targeting and prolonged blood circulation times by conjugating different ligands to their surface. Additionally, they can enhance drug distribution and pharmacokinetics by increasing drug stability and solubility, and decreasing its cytotoxicity to healthy tissues. Polymeric micelles are highly used in drug delivery applications especially Pluronic copolymers due to their higher drug loading capacities, ability to overcome multi-drug resistance (MDR), lower CMC (enhanced stability) compared to other micelles, and the ability to release drugs in response to specific triggers.

Figure 3A:
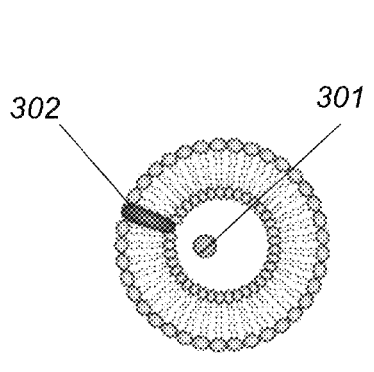
FIGS. 3A-D illustrates embodiments of structures of liposomes and immunoliposomes.

Regular micelles may only encapsulate hydrophobic drugs, even though recently-reported core-inversible micelles may also encapsulate hydrophilic drugs. Another downside includes the recognition and elimination by the immune system, which can be neutralized using PEO copolymer in the micelles structure, but this was found to interfere and prevent their interaction with cells, a process that may be necessary for a successful drug delivery carrier/system. Stability problems emerged with incorporation into the bloodstream, where micelles are diluted beyond their CMC leading to unwanted early release of the therapeutic agent. They might be stable at higher CMC values, but may not be tailored to the body. Several other successful approaches have been suggested to deal with this drawback. Liposomes as Nanocarriers Liposomes can be used to entrap various types of molecules including: drugs, vaccines, plasmid DNA, peptides, hormones, antisense oligonucleotides or ribozymes, nutraceuticals and cosmetics. Liposomes are one of the most widely used nanocarriers in drug delivery. Liposomes are spherically shaped phospholipid bilayers (lamellae), and in embodiments may have a diameter range of between about: 20 to 1000 nm, 100-900 nm, 200-800 nm, 300-700 nm, or 400-600 nm in which each of these monolayers is constitutes of amphipathic molecules; that is a hydrophilic (polar) head and hydrophobic (nonpolar) tail, and can also contain other molecules such as cholesterol, carbohydrates and proteins. By shielding their hydrophobic domain, amphipathic lipids may form enclosed membranes in aqueous environments as shown in FIG. 3A, which is described further in detail herein. The hydrophilic heads face the outside of the double layer, whereas the hydrophobic tails come together to form the hydrophobic region, in which poorly water-soluble antineoplastic drugs can be loaded. The aqueous compartment inside the core has the ability to entrap hydrophilic drugs. In embodiments, some of the chemotherapeutic drugs that can be loaded into liposomes include doxorubicin, annamycin, daunorubicin, vincristine, cisplatin derivatives, paclitaxel 5-fluorouracil derivatives, camptothecin derivatives, and retinoids. At least some liposomal membranes are considered similar to some cells membranes structures, rendering them safe to use in clinical trials (biocompatible and biodegradable). In some instances, the properties of liposomes can be tailored to perform various functions by controlling, for example, their lipid composition, particle size, surface charge, lipid membrane fluidity, and steric stabilization.

The two main types of phospholipids of liposomes are sphingomyelin and phosphoglycerides, in which they have sphingosine and glycerol as a backbone respectively. FIG. 1 illustrates a schematic drawing of the amphipathic molecule composition of phosphoglycerides and a lipid bilayer constructed from phosphoglycerides. Phosphoglycerides are the most common type of phospholipids forming liposomes found in nature; they consist of a phosphatidic acid 101 that is attached to a hydrophilic head group 102. Phosphatidic acid can include a glycerol backbone in which two fatty acid chains 104, each has 14 to 24 carbon atoms in length, are attached to carbon-1 and carbon-2 of glycerol 103. And carbon-3 of glycerol 103 is esterified to the phosphate group 105 as can be seen in FIG. 1, to form a head group. The head group is esterified to the phosphate group, and the head group may be, for example: choline, serine, inositol, or as ethanolamine molecule leading to different Glycerophospholipids: phosphatidylcholine (PC), phosphatidylserine (PS), phosphatidylinositol (PI), or phosphatidylethanolamine (PE), respectively.

Figure 2:
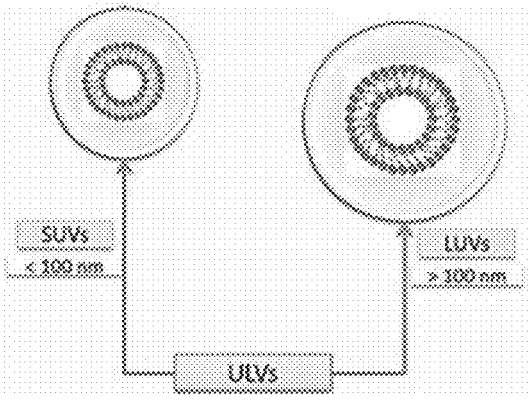
FIG. 2 illustrates a classification of liposomes.
Figure 2:
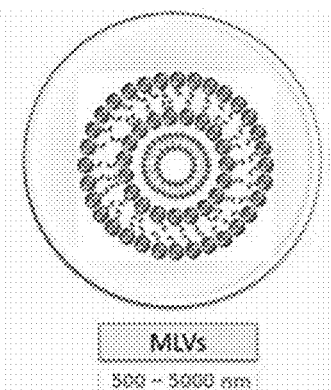

Liposomes are classified, depending on their number of bilayers into multilamellar vesicles (MLVs) and unilamellar vesicles. FIG. 2 illustrates classification of liposomes based on size. In multilamellar vesicles (MLVs) more than one fluid compartment are present and separated by lipid bilayers. As shown in FIG. 2, they range in size between 500 and 5000 nm, while Unilamellar vesicles (ULVs) contain only one internal aqueous compartment. The later can be further classified into small unilamellar vesicles (SUVs) that range in size between 50 and 100 nm and large unilamellar vesicles with a size in the range of 100 to 250 nm, respectively. Most liposomes traditionally used in drug delivery belong to the SUVs type due to their higher capacity for drugs. Even though MLVs can exhibit slower drug release and higher loading capacities for hydrophobic compounds, they may have limited industrial applications due to their heterogeneity in size, large diameter, multiple internal compartments, and inconsistent methods of preparation.

Liposomes can be also classified based on the stimuli that they are responsive towards. Echogenic liposomes are rendered sensitive to ultrasound by entrapping gas in their core, thus releasing their contents as soon as ultrasound is applied. eLiposomes may contain nanoemulsions that change phase from liquid to gas in response to ultrasound, thus leading to subsequent drug release. Temperature sensitive liposomes (TSL) may be triggered by hyperthermia. Liposomes can also be made sensitive to pH, in which they usually respond to acidic conditions, which is a characteristic of the tumor region, and late endosome within the cell after liposomes endocytosis (internalization). In addition, it is possible to create light-sensitive and microwave sensitive liposomes as well.

Nanocarriers may be administered to the body of a patient in various ways, including but not limited to: oral administration, intravenous injection, intramuscular injection, or subcutaneous injection. Nanocarriers face many unexpected hurdles upon interaction with body fluids. They are naturally attracted to the liver by the action of clearance. Liposomes can be engineered by covalently attaching moieties to their surface in order to render them more stable, less immunogenic, better target the infected cells, increase blood circulation time, and/or protect them from degradation in the plasma. Liposomes blood circulation time depends on their size, their surface charge, and degree of unsaturation of the lipid chains. Commonly used targeting moieties attached to the liposomal surface include antibodies, hormones, and proteins.

Figure 3B:
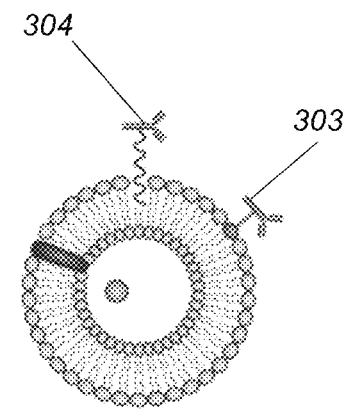
Figure 3C:
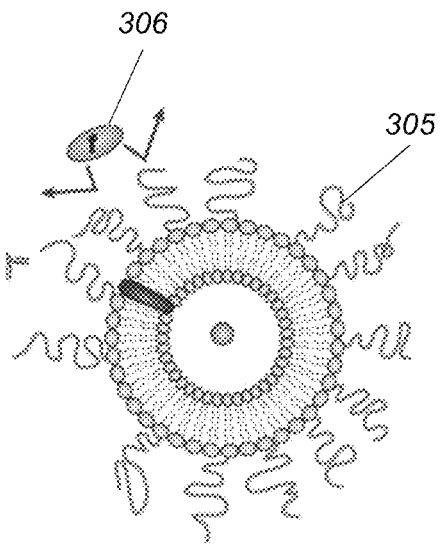
Figure 3D:
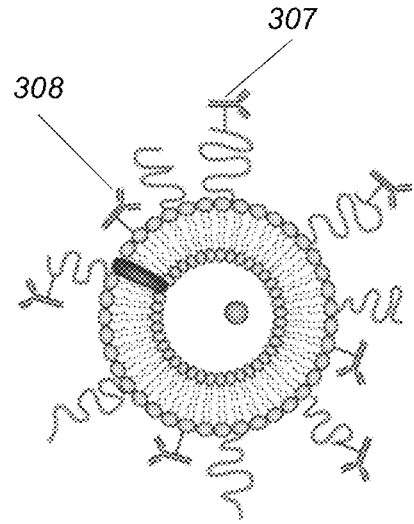

FIGS. 3A-3D illustrate structures and evolution of liposomes. FIG. 3A illustrates a hydrophobic drug 302 which may be trapped at the hydrophobic region of the liposome, and a hydrophobic drug 301 which may be loaded in the aqueous compartment of the liposome. FIG. 3B illustrates liposomes after the attachment of antibodies 303 covalently to the surface groups and/or antibodies 304 hydrophobically anchored into the membrane. FIG. 3C illustrates stealth liposomes, where a protective polymer 305 hinders opsonin proteins 306. FIG. 3D illustrates liposomes which includes both antibodies and a protective polymer, where antibodies 107 are directly attached to the surface and antibodies 108 are attached to the distal ends of the protective polymer.

In embodiments, sterically-stabilized liposomes (also referred to as stealth liposomes) may have the hydrophilic polyethyleneglycol (PEG) attached to their surface as shown in FIG. 3C. This protective polymer may help in avoiding hydrophobic interactions with plasmatic proteins (i.e. opsonin proteins 306 of FIG. 3C) and their subsequent adsorption by the liposome membrane. This can reduce the trapping of liposomes by macrophages of the mononuclear phagocyte system (MPS, also known as the reticuloendothelial system (RES)), in a process called opsonization, thus resulting in prolonged blood circulation time. Basically, increasing the hydrophilicity of the liposomes creates a steric barrier to prevent detection by the MPS and subsequently prevents liposome clearance.

In some embodiments, stealth liposomes also have the enhanced ability to cross biological barriers and are used in the treatment of solid tumors. In certain embodiments, oating liposomes with PEG was found to increase their half-lives up to 12 to 30 hours in animal models and 21 to 54 in humans. But the PEG polymer can also prevent cells interactions. Also, it was reported that some stability issues rose with PEG stealth liposomes. Due to their hydrophobic nature, the PEG polymers can act against the hydrophilic property of the head group and cause destabilization. To counteract this effect, a sufficient amount of cholesterol (a rigidifying agent) can be added into stealth liposomes. Other coating polymers have been suggested but because of PEG's ease of preparation, relatively low cost, controllability of molecular weight and linkability to lipids by a variety of methods, it was widely used. It was reported that the size and the fluidity of the liposomes could affect its uptake by the RES, the smaller their size and the more rigid they are, the better chance they have to avoid clearance. Another approach to deal with liposomes clearance is to render them less foreign and more recognized as self-proteins by the macrophages of the MPS using coats of natural glycolipids, gangliosides. But it wasn't pursued due to some difficulties.

As shown in FIG. 3B, in immunoliposomes, antibodies and their fragments may be attached to the liposomes. Antibodies can identify antigens overexpressed on the targeted cells surface. Each antibody binds to a specific antigen, making it possible to selectively target that cell, hence avoiding undesired interactions with healthy cells. Most widely used moieties for that purpose are immunoglobulins (Ig) and their fragments, which can be attached to the liposomes by covalent bonds. It should be noted that they may still end up in the liver due to insufficient time for the ligand on the liposome to interact with the targeted receptor on the cell surface. This can be solved by increasing their blood circulation time, thus leading to the development of sterically stabilized immunoliposomes. Sterically stabilized immunoliposomes can be synthesized by attaching the antibody directly to the liposomes surface parallel to the PEG polymer, or successively to the PEG polymer on the surface of the membrane, as can be seen in FIG. 3D. Using the later methods will result in having both properties of long circulation time and targeting ability.

Liposomes can also be modified with cell-penetrating peptides. Some viral proteins have the ability to penetrate cells through the protein transduction phenomena, one such example is the TAT protein found in HIV-1, in which it mediates intracellular transport of nanoparticles. Using this method there is a better chance for nanoparticles to escape the endosome and get into the cytoplasm. It has been proven using TAT as a ligand on liposomes surface facilitate its delivery into cells.

In certain embodiments, liposomes, as a drug carrier, are known to have following advantages: 1) enhanced drug pharmacokinetics, distribution, and solubility, by preventing drug interaction with bodily fluids and early degradation; 2) prolonged duration of drug exposure and control the drug release rate; 3) natural accumulation around the tumor area which increases the drug's concentration at the diseased site compared to healthy tissue; 4) ability to be actively targeted to bind to cancer cells more preferentially enhancing tumor uptake also intracellular drug delivery; 5) possible modifications to make liposomes more appealing to be used in many domains other than drug delivery, including diagnosis, regenerative medicine, and gene therapy; 6) the ability to control the release of drugs, and to increase solubility of drugs; 7) biocompatibility and bio-degradablability and weak immunogenicity; 8) ability to overcome multi-drug resistance; 9) the ability to deliver various types of drugs and increased loading capacity; 10) the ability to be remotely triggered.

However, it is also known that certain currently available liposomes have the following limitations as nanocarriers: enhanced accumulation at the tumor site but less blood circulation time (more clearance); insufficient time to interact with the cancer cells due to ending up in liver and certain side interactions.

EPR Effect

The first generation of nanocarriers used in nanomedicine were based on the EPR effect, also called passive targeting. EPR is defined as the enhanced vasculature and system permeability to molecules and nanoparticles in and around the tumor area; due to the defectiveness of the tumor vascular structure, and entrapping those particles for prolonged periods of time before their subsequent clearance by the lymphatic system; due to the impaired lymphatic system at the tumor site. EPR may be applied to biocompatible lipidic particles and macromolecules with large molecular weights, whereas low molecular substances are observed to return to the circulatory system by diffusion. Usually, long circulation times (around 6 hours) are needed for the accumulation of any drug due to EPR effects.

Enhanced tumor permeability is a physical phenomenon that depends on blood vessels morphological differences between normal and healthy tissue; due to rapid angiogenesis. Normal blood vessels are linear and stacked regularly. But blood vessels in tumors have openings in the endothelium and are weak due to the lack of an external muscle layer, leading to high blood pressure in the tumor site. Tumor blood vessels also show polymeric leakage at the capillary level. These structural deviations and vascular permeability render cancer vessels leaky, and as a consequence, macromolecules and lipid particles are allowed to extravasate from the blood vessels into the tumor interstitial space and accumulate as time passes by. Permeability is also enhanced by the increased production of permeability mediators such as bradykinin, nitric oxide, prostaglandins, and VEGF (or vascular permeability factor), in or near the most solid tumors. It is also known that the effectiveness of EPR depends on the molecular size and/or weight. It was also reported that endothelium openings range from 300-4700 nm, in which they are not found in normal tissue. Generally, liposomes that range from 90-200 nm are known to exhibit increased accumulation due to EPR effects.

Known measures suggested to enhance the EPR effect include raising the systemic blood pressure, increasing NO concentration utilizing NO-releasing agents, and increasing kinin (bradykinin) concentration using ACE inhibitors. Further, in order for the penetrated materials to accumulate, they need to escape clearance. This happens as a result of functional defectiveness of the lymphatic system that usually removes foreign particles from the interstitial space.

Active Targeting

As passive targeting provided an approach to cancer treatment, it doesn't exclusively target tumors, as inflammation also exhibits EPR effects. Additionally it does not guarantee intracellular uptake of the drug. Moreover, the issue of molecules diffusing back to the bloodstream is considered another drawback, and it has become clear that relying on EPR effects alone for targeting is not adequate. As have been mentioned elsewhere in the specification, cancer cells over-express some receptors on their surface vastly more than those of normal ones. This is generally due to cancer characteristics mentioned earlier, such as accelerated proliferation, abnormal angiogenesis and some other mutations.

Active targeting in liposomes may include utilizing ligand-receptor links to increase cellular uptake of the nanocarriers through receptor-mediated endocytosis, where after EPR effects lead them close enough to the affinity of the tumor tissue, the conjugated ligand on the surface of the liposome is recognized by its receptor overexpressed on the cancer cell surface, leading to increased efficient targeting.

Generally, most cancers over-express VEGF receptors, integrins, and vascular cell adhesion molecules which are all related to cancer angiogenesis. Folate receptors were also known to be extensively over-expressed in many tumors such as lung, brain, breast, kidney, and ovary cancers, in order to improve their growth. Other cell division receptors are human epidermal receptors (HER) family including EGF receptors (HER1) that are commonly found in multiple cancer types such as head and neck, bladder, ovarian, cervical, and oesophageal cancer. Also, the transferrin receptors are of importance in cell division, and are generally over-expressed in multiple tumors including brain capillary endothelial cells. Also, some cancers overexpress receptors specific to one type of the tumor cells, and these depend on the malignancy, location, and stage of the tumor.

Ligands for Targeted Drug Delivery

In certain embodiments, ligands used in ligand-targeted drug delivery may include glycoconjugate, oligopeptide, nucleic acids, aptamers, carbohydrates, vitamins, whole proteins, peptides, and antibodies and antibody fragments against tumor markers.

The folate receptor can internalize its ligand into the cytosol. Upon attachment of the ligand, both the ligand and the receptor are internalized and then moved to the acidic portion of the endosome (late endosome) where de-attachment normally happens. The receptor is recycled back to the membrane, and the nanocarriers can release their contents into the cytosol. Folate group can be covalently attached to the phospholipid or cholesterol of the liposomal drug carrier, and it has shown to reduce cardio-toxicity more than the free drug, induce cytotoxicity to targeted cells, and inhibits tumor development. It was reported that attachment of folic acid to micelles, such as liposomes, (in the PEG copolymer side) entrapping a drug significantly increased cellular uptake of the drug than those which are folate unconjugated micelles against KB cells over-expressing folate receptors.

It is reported that coupling PEG end of drug-loaded liposomes to transferrin significantly increased the cellular uptake by the cell line in vitro. It was also observed that OX26 monoclonal antibody (mAb) could be used to better target liposomes towards the transferrin receptor when attached to the distal end of the PEG molecules conjugated to the surface and coating the liposomes.

In certain embodiments, EGFR may gave various ligands; they include EGF, anti-bodies, antibodies fragments, aptamers, and EGFR-specific low-molecular-weight peptides. FDA-approved antibodies with affinity to EGFR include Trastuzumab and the chimeric monoclonal antibody cetuximab. Several nanoparticles including liposomes have been modified using cetuximab. Antibody fragments of cetuximab have also been used as moieties for liposomes, due to their small size. The native ligand EGF has a very high affinity for EGFR and showed strong cytotoxicity to tumors, but could also lead to triggering signaling pathways of the receptor and contribute to tumor development. Peptides used for EGFR targeting include D4 and GE1. Anti-EGFR aptamers, a class of functional oligonucleotides similar to the antibodies in their binding affinity, have been successfully used to specifically deliver gold nanoparticles to EGFR.

Increased overexpression of vasoactive intestinal peptide receptors (VIP) on breast cancer cells make them successful targets for the VIP-conjugated nanocarriers. An increased intracellular uptake and subsequent cytotoxicity have been reported upon using VIP as an active targeting moiety in stabilized micelles.

Some integrins may be over-expressed in actively proliferating endothelial cells. They have several ligands of extracellular matrix (ECM) proteins including fibrinogen, vitronectin, collagen and fibronectin. Therefore it has been suggested to target integrins of the tumor tissue using short peptides containing an arginine-glycineaspartic (RGD) site that mimics fibronectin and has high affinity towards these integrins. The RGD cell adhesion sequence is the cell attachment site of more than 20 integrins including integrin $\alpha_{IIb}\beta_3$ and $\alpha v \beta_3$-integrins. Other peptides that bind to integrins represent slight variations of the RGD sequence, and may include but not limited to: the KGD sequence that binds specifically to $\alpha_{IIb}\beta_3$ integrin, RHD sequence, Platelet Endothelial Cell Adhesion Molecule (PECAM, the endothelial cell marker) that binds to $\alpha v \beta_3$-integrins, or the NGR sequence that can bind to various RGD-directed integrins but has lower affinity than the RGD sequence.

Vascular cell adhesion molecules provide very highly specific target receptors due to that they are almost exclusively expressed on cancer cells. These also bind to ECM proteins that are considered crucial for metastasis. Ligands used may include anti-VCAM-1 (vascular cell adhesion molecule 1) monoclonal antibody.

Liposomes that have monoclonal antibodies or antibody fragments conjugated to their surface are called immunoliposomes, and the antibodies have high affinity towards specific antigens expressed on cell surfaces. Antibodies may bind to their corresponding epitope site on the antigen over-expressed on many cancer cells. Some tumors are highly immunogenic, and some are not, and the presence and the type of the antigen vary from one type of malignancy to another, which eventually affects the efficacy of the immunoliposomal therapy. As described elsewhere in the specification, potential highly investigated targets for antibodies may include VEGF, EGFR, HER2, transferrin receptors, and prostate-specific membrane antigen (PSMA).

HER2 receptors have an ability to internalize their ligands resulting in the endocytosis of the antibody mediated nanoparticles. Trastuzumab is known to be humanized monoclonal antibody for HER2. Nanoparticles coupled with trastuzumab have been investigated for HER2 positive breast cancer. Another known chimeric monoclonal antibody is cetuximab which has a high affinity towards the EGF receptor (EGFR). Cetuximab-targeted gold nanoparticles were investigated for delivery of chemotherapeutics to many cancers including pancreatic and colorectal carcinoma, and results showed significant tumor growth inhibition. Cetuximab immunomicelles were suggested as delivering vehicles for doxorubicin agent, as well as immunoliposomes conjugated with cetuximab to deliver boron in glioma cells overexpressing EGF receptors. Anti-transferrin receptor antibodies include OX26 and R17217 monoclonal antibodies. Also, antibodies for Prostate-specific membrane antigen (PSMA) include J591 monoclonal antibodies. Bevacizimab (Avastin) was successfully implemented in combination with chemotherapy in the treatment of metastatic breast cancer, in which it was targeted against VEGF overexpressed as a result of angiogenesis. Lastly, rituximab, an anti-CD20 monoclonal antibody is used as a conjugate in nanoparticles to target lymphoma tumors overexpressing CD20 receptors. Anti CD20 receptors mAb are not considered internalized mAb in contrast to anti CD19 receptors mAb.

Due to the large size of monoclonal antibodies which could pose an obstacle for intracellular drug delivery, antibody fragments were suggested because of their small size and similar affinity to their corresponding antigens as whole antibodies do. Antibody fragments used in nanomedicine include single-chain variable fragments (scFV) and antigen-binding fragments (Fab). Nanocarriers decorated with antibody fragments exhibit reduced clearance by the RES and their small size allow for better penetration. scFV that bind specifically to an isoform of fibronectin was found to enhance the targeting ability of liposomes. Also, scFV-CM6 was found to bind specifically to a protein extensively overexpressed on surfaces of tumor cells (TEM1) and was used successfully in making immunoliposomes. It was also reported that efficient internalization was shown when liposomes conjugated with single-chain anti-EGFR antibody were used. Additionally, some antigen-binding fragments (Fabs) of monoclonal antibodies were successfully used as conjugates to liposomes. These include Fabs targeting $\beta_1$ integrins that are overexpressed in lung cancer and Fab of the mAb anti-GD(2) that targets disialoganglioside which is overexpressed on the surface of neuroblastoma cells. Also, human B-cell lymphoma was targeted using immunoliposomes conjugated with mAb anti-CD19 or its Fab fragments. Finally, Fab fragments of trastuzumab were used to target HER2 overexpressing breast cancer cell lines. Results in vitro showed increased cytotoxicity, and in vivo showed enhanced tumor growth inhibition.

Monoclonal Antibodies and Immunogenicity of Tumors

An antigen is any molecule that can interact with an antibody, and its binding site called epitope. An antigen can be a peptide, a lipid, a carbohydrate, a nucleic acid, or any other molecule. Any substance that can induce an immune system response is defined as immunogenic, all immunogens are antigens, but not all antigens are immunogens (they also include allergens and tolerogens). Depending on the immunogen size, chemical, composition, conformation, and its "foreignness" they have the ability to provoke an immune response.

Some antigens that are marked "self" do not stimulate an immune response; these are normally expressed on normal healthy cells. But mutations in cancer cells result in either altering these proteins making them more foreign, or overexpressing them, in which both should lead to an immune response. Antibodies are naturally produced by B-cells as a response to the antigen representation by helper T-cells. Antibodies belong to proteins of the blood called immunoglobins. They are classified into five different classes; IgM, IgD, IgG, IgA, and IgE. Each class has a similar component in their structure, and a small variable fragment (Fv) part (N-terminal (amino-terminal) domains) found in the antigen binding fragment (Fab). That variable fragment is unique for each antigen-antibody binding. Antibodies consist of dual heavy and light chains joined by disulfide bonds with average molecular weight of 150 kDa.

Monoclonal antibodies are antibodies produced in a laboratory by culturing antibody-producing cells. Their production depends on immunizing a mouse with a pathogen or any other immunogenic substance. These complex antigens may have many antigenic sites which result in the production of various antibodies in the blood stream for that one complex antigen. Each antibody is produced by a specific antibody-producing cell in the spleen. Antibody-producing spleen cells may be fused with immortal myeloma cells to have hybrid cells that contain both immortal properties and antibody secreting ability of parent cells. These can then produce polyclonal antibodies. Each hydridoma may be then cultured individually to produce separated clones that secrete one specific type of antibodies, called monoclonal antibodies. Using monoclonal antibodies, one can ensure the precise binding to only one antigenic site of the tumor, without concern about whether or not it will affect other targets.

Monoclonal antibodies can be used as homing devices to guide nanocarriers to tumor targets (receptors) and hook with them, or in immunotherapy to interfere with cell signals and specific molecules functions that are necessary for tumor growth and angiogenesis as previously discussed in targeted therapy.

Limitations to monoclonal antibodies include expensive production, immunogenicity, and limited conjugation density on nano-carriers due to their large size. Also, mouse-derived antibodies were shown to induce some allergic-like reactions when used in humans, which raised the need for creating chimeric or humanizing murine-derived antibodies, or aiming for producing fully human monoclonal antibodies. Chimeric monoclonal antibodies are considered less compatible with humans than humanized ones; they have the variable fragment from a murine source and the constant region from a human. While humanized monoclonal antibodies have only the complementary determining regions of the variable regions (CDRs) from a murine source. Fully human monoclonal antibodies were developed using phage-display technologies. Usually, fragments of antibodies display less immunogenicity.

Modifications to mAbs may be needed for conjugation purposes. Sites for chemical binding in antibodies, and proteins, in general, include thiol groups (sulfhydryl groups) that are found in cysteine residue of the protein, amine groups that are located in the lysine residue, and carbohydrates. Usually, sulfhydryl bonds in proteins are found in their reduced version as disulfide bonds (in cystine), which first need to be activated into a free thiol group in order for the conjugation to be successful. These modifications are known to affect the antigen-antibody binding sites except for the carbohydrate modification. For disulfide modification at low pH, damage control can be achieved.

Generic names of monoclonal antibodies used in therapy are based on their targets and type of monoclonal antibody used. One of skill in the art will recognize that a "ximab", "zumab", or "mumab" suffix indicates either chimeric human-mouse antibodies, humanized mouse antibodies, or fully human antibodies respectively. A stem in the middle indicating their type of target is a "ci(r)", "t(u)", "li(m)", "tin", or "zom" to indicate a circulatory system target, a tumor target, an immune system target, a tyrosine kinase inhibitor, or a proteasome inhibitor respectively.

Trastuzumab, also called Herceptin, is a humanized IgG (1) kappa monoclonal antibody (145.5 kDa) with high affinity towards the HER2 receptor overexpressed in breast tumor cells. Trastuzumab can prevent HER2 hetero-dimerization and stop cells signaling related to tumor development. Thus it has been used as a treatment in immunotherapy as described elsewhere in the specification. Trastuzumab has been shown to reduce the risk of recurrence when used as adjuvant therapy, and also augment the effects of chemotherapy. Trastuzumab was commonly used in combination with Paclitaxel, Docetaxel, Navelbine, Gemcitabine, and Capecitabine. Pertuzumab is another monoclonal antibody specific to HER2 but binds to a different epitope than trastuzumab.

Ultrasound as a Trigger for Drug Release

Triggering mechanisms may allow for controlling the release at tumor sites, resulting in dismissing side effects on healthy cells, avoiding inducing drug resistance that is due to long accumulation time. They may also facilitate penetration into the tumor, and endosomal release. Releasing the drug too early or too fast may result in damaging healthy cells, while releasing the drug too slow or too late won't allow for the concentration to reach the cytotoxic dose, thus a controlled release may be needed. Once the drug nanocarriers reach the tumor site, spatial and temporal controlled release may be obtained by ultrasound, such a mechanism is widely used for triggered release due to its low cost, safety, and focused feature.

Ultrasound is a cyclic sinusoidal acoustic wave that has high-pressure phases (compression) at the upper peaks and low-pressure phases (refraction) at the lower peaks. It propagates through the medium, by transferring of energy through the oscillation of particles, thus it propagates faster in solids than in fluids. The ultrasound frequency ranges are above the human hearing range (20 kHz). Attenuation is the loss of intensity as the wave travels through some medium, where energy is lost either by absorption or transferred to other forms of energy.

Parameters of ultrasound that are of importance in triggered drug release include its frequency, intensity (power density), and mode of operation. Low-frequency ultrasound (LFUS) which is generally less than 1 MHz is applied to trigger release. High-frequency ultrasound (>5 MHz) has been used in diagnostic imaging in medicine for ages. Generally, as the frequency of the applied ultrasound increases, less penetration into tissue occurs. Further, at low frequencies cavitation increases, as described further elsewhere.

Ultrasound intensity is the energy carried per cross-sectional area of the applied beam. Low-intensity ultrasound usually doesn't induce hyperthermia in contrast to high-intensity ultrasound (HIUS) that is frequently used as a treatment of cancer as previously described, where high temperature has the ability to damage cells in the site where they are targeted towards. Several studies report a proportional relationship between drug release and US power intensity. The mode of continuously applying ultrasound may be used in triggered therapy as well as the discontinuous mode (pulsed mode), where ultrasound has on and off periods for specific time spans.

Ultrasound has thermal effects and non-thermal effects (mechanical effects). Thermal effects (hyperthermia) previously described are the result of energy dissipation of HIUS into thermal heat rising tissue temperature. Mechanical effects result from the acoustic wave propagation and pressure variations. One such effect is acoustic cavitation, which is the formation of gas bubbles in a liquid, due to changes in pressure. Cavitation depends on the intensity of the ultrasound, and it only occurs at a certain threshold. At low-pressure amplitude, the gas bubbles exhibit stable oscillation, in which they contract and expand slightly, this is referred to as stable cavitation. On the other hand, inertial cavitation results from high-pressure amplitude that leads to gas bubble collapse. The bubbles increase rapidly in size until they reach their resonant size, at which then they collapse resulting in: high pressure and temperature, sonic jet of fluid (near solid surfaces) is produced and damages nearby cells, shock waves that shear open the cells, and the formation of new small bubbles that reinitiate the cycle. Stable and inertial cavitation can occur in the same situation following each other, they are not separate phenomena. Another mechanical effect is acoustic streaming which is a direct result of the US wave propagation through some medium. In acoustic streaming, particles move in the direction of the flow, resulting in micro-streaming, bulk-streaming or both. The latter is considered a powerful mechanism that facilitates the delivery of drugs.

One of important acoustic parameters is the mechanical index (MI), which is the probability of collapse cavitation to happen. In triggered drug delivery, the aim is to find the optimum ultrasound parameters that permit enhanced drug delivery without harming healthy cells. This could be better achieved if we understood the mechanism by which enhanced triggered delivery works. Several mechanisms could be the cause of the triggered drug delivery: disruption of the drug nanocarriers; enhancement of drug distribution in tumor tissue; enhanced intracellular drug uptake by endocytosis; and/or increase in cellular uptake of the nanocarriers by enhancing the cell permeability.

The first possible mechanism could be that shear stress resulting from both wave pressures and cavitation can lead to disruption of the nanocarriers membrane. Ruptures resulting from cavitation are particularly important for site triggered drug delivery, to avoid drug release near healthy cells. In the second mechanism, microstreaming may enhance the distribution of the encapsulated drug by diffusion through the tumor tissue. Moreover, cavitation has an enhancement effect on the motion of the fluid near the tumor cells, in which drug dispersion occurs. Gas bubbles of the cavitation phenomena can pull denser materials (nanocarriers for example) towards them, resulting in their rupture. In the third mechanism, the uptake of micelles into tumor cells was reported in several studies, suggesting nonspecific endocytosis. Additionally, cell membrane permeability may be a direct result of events resulting from cavitation. Shock waves, sonic jets, and micro-streaming may induce pore formation on cells membranes and thus facilitating the drug uptake into cells.

Modeling the Release Kinetics

The concept of controlled release lies within the fact that an initial dose of the drug is needed and then a further slow release, to maintain the drug therapeutic level as long as possible. Control release for a drug delivery system is needed since some drugs release too fast from carriers, before getting to the tumor, and others too slow that the therapeutic effect can't take place.

Controlled release aims to reduce the frequency of the treatment and increase patients comfort level. For this purpose, modeling of the release kinetics is needed in the optimizing stage, where the patterns of the release can be predicted without the need for unnecessary studies or experiments. It may also provide some insight into the mechanisms by which the drug is released and some other physical aspects as well. Several release mechanisms are common, they include but not limited to, release by drug diffusion through the polymer membrane, by the degradation of the polymer, or by chemical disassociation of the drug.

For example, the kinetics of drug release of liposomes in Phosphate-buffered saline can give an idea about the release behavior in vivo, thus reducing studies done in vivo. Models describing drug dissolution differ based on their assumptions, but they can be categories as follows: slow zero order, first order, and ones that start rapidly and then reduce to either of the previously mentioned types. Kinetics can be influenced by the type of drug, particle size, solubility, and the amount used. Nine models will be used in this thesis to discuss the release kinetics of the model drug calcein under low frequency ultrasound.

Breast Cancer and Immunoliposomes Targeted Towards HER2

In some embodiments, doxorubicin ("Dox")-loaded immunoliposomes (ILs) may be provided. Sterically stabilized liposomes (70-100 nm in diameter) may be conjugated to anti-HER2 mAb fragments. Delivery of these immunoliposomes into HER2 overexpressing cells may result in intracellular uptake of 600 times higher than nontargeted stealth liposomes, but they may exhibit similar uptake in non HER2 overexpressing cells, which may demonstrate the effectiveness of targeting moiety. Also, ILs may exhibit 700 times more accumulation in targeted tissue than in negative cells. In vivo studies conducted on xenograft that overexpresses HER2, reported that ILs loaded with doxorubicin yielded improved anti-tumor activity in contrast to all other treatment options used which included: free Dox, free mAb (trastuzumab), liposomal Dox, free Dox conjugated to the mAb, and liposomal Dox linked to trastuzumab.

However, tumor tissue levels of ILs and liposomes may be the same, but ILs may exhibit intracellular uptake opposite to non-targeted liposomes that accumulated in the tumor stroma, which may result in 10-30 times higher cytotoxicity. Also, administration of ILs may not increase clearance, hence showing that anti-HER2 mAb fragments may not affect the stabilization or the non-immunogenicity of sterically stabilized liposomes.

In one instance, immunoliposomes (140 nm in diameter) may be conjugated with trastuzumab mAb to deliver both Paclitaxel (PTX) and rapamycin (RAP) therapeutic drugs into 4T1 cells that are triple negative breast cancer cells and SKBR3 cells which are HER2 positive breast cancer cells.

The encapsulation efficiency can be about 56% and 70% for PTX and RAP respectively, and the conjugation of Trastuzumab can be above 70% using a thioether bond. In embodiments, cytotoxicity of SKBR3 cells for the ILs can be increased compared to the control liposomes (non-targeted liposomes). This can be a result of the enhanced uptake mediated by the mAb bond to the HER2 on the cells. The in vivo study investigated the immunoliposomes co-loaded with both drugs, control liposomes, and solution of PTX/RAP against human xenograft HER2 overexpressing tumors, and immunoliposomes showed better anti-tumor growth activity. RAP can increase PTX induced apoptosis, hence produce synergetic effects in the presence of trastuzumab.

Stability of actively targeted liposomes may not be affected much in circulating conditions. It has been reported that liposomes in circulating conditions leaked 20% of their contents after 5 hours and 42% after 8 hours, while liposomes in cell culture conditions leaked 5% after 5 hours and 9% after 8 hours. Thus liposomes may be considered stable in circulating conditions in times up to 8 hours.

Antibody Conjugation Methods

Attachment methods of targeting ligands to liposomes may include covalent and/or noncovalent bonds. The attachment done to the distal ends of the PEG-PE anchor may be more efficient than linking directly to the surface of the liposome. The approach of conjugating the ligand to liposomes after their synthesis may be better than linking them to lipids prior to liposomes synthesis.

In certain embodiments, types of linkages used in the conjugation methods may include, for example, thioether bonds, disulfide bond, amide bonds, Hydrazide bonds, and crosslinking primary amines. It has been reported that ILs-PEG-mAb linkage displayed increased binding, but reduced internalization compared to ILs-mAb linkage (but still contains PEG on their surface parallel to the mAbs). It has been also reported that attaching the mAbs to distal ends (ILs-PEG-mAb) showed that binding was independent of the PEG density. Additionally, increasing mAb density on immunoliposomes has been reported to enhance binding and internalization. A conjugation efficiency of 70-90% has been reported for using a thioether covalent bond in conjugation.

Also, stealth immunoliposomes may be prepared with trastuzumab Fab conjugated to the surface for one approach and conjugated to the distal ends of PEG chain for another approach, both in which they use thioether bonds. Increasing PEG density was reported to decrease the binding with the first approach but did not affect the second approach. Also, it was reported that binding and internalization was much higher in HER2 positive cells than in negative ones for both approaches.

In some embodiments, a thioether bond in which the liposomes where thiolated instead of the antibodies, may be used. When the attachment was done directly to the stealth liposomes surface, the PEG polymer may affect the attachment efficiency by hindering the antibodies away from the surface. So the attachment may be made on the distal ends of the polymer, and to get high conjugation efficiencies. A summary is presented in Table 2 that shows an embodiment of conjugation efficiencies of thioether bonding strategies with and without PEG polymer on 100 nm liposomes.

TABLE 2

| | Antibodies conjugation efficiency using two different strategies of applying the thioether bond, with changing the binding site and mPEG polymer % on liposomes surface | |
| --- | --- | --- |
| Setup/strategy | Conventional method where Antibodies are thiolated and liposomes maleimided | Andibodies are maleimided and liposomes or PEG polymers are thiolated |
| At the surface with 5% mPEG | 63% | 10% |
| At the surface with 0% mPEG | 72% | 69% |
| At the end of the PEG with 4% mPEG on the surface | — | 61% |
| At the end of the PEG with 0% mPEG on the surface | — | 60% |

Thioether bonds may require pre-derivatization of both liposomes and antibodies, which is considerably complicated and not feasible when the antibody is especially expensive. A "Bendas protocol" may be used, where a cyanuric chloride acts as a linkage between the PEG distal end and the antibody to prepare immunoliposomes. This method required no prior derivatization to the antibody and no extra chemicals as well. Binding efficiency for the immunoliposomes was also established which means no harm was done to the binding site. Immunoliposomes stability was also confirmed. Usage of cyanuric linkage to form immunoliposomes in a continuous process has been also reported.

Calcein for Ultrasound Triggered Drug Delivery

Ultrasound release may be studied under the effect of frequency and power density when the liposomes nature is not changing. The liposomes parameters affecting ultrasound include, for example, lipid ratio, surface charge, and PEG polymer density.

Calcein (a model drug) release from liposomes has been reported to be higher at LFUS than at HFUS, and the amount released was reported to increase with increasing exposure time and the mechanical index, possibly due to mechanical effects rather than thermal effects.

The dependency of the release on the liposome membrane structure was also reported in dox-loaded liposomes under LFUS effects; 30% higher release using DOPE based liposomes than DSPE based liposomes. Accordingly, DOPE-based liposomes may be sonosensitive lipids.

It was also reported that PEGylated liposomes showed 10 fold more permealization upon exposure to LFUS than the control non-PEGylated liposomes, due to the absorption of energy by the PEG groups which are considered sonosensitive.

It was reported that estrone-targeted calcein-loaded immunoliposomes upon exposure to LFUS may exhibited higher initial release rates than the non-targeted ones, but the same final release rate for both liposomes types.

Method for Synthesis of Immunoliposomes

Sterically stabilized liposomes with functional groups at their ends may be synthesized, using a mixture of lipids. In certain embodiments, the functional group may be related to the type of linkage wanted and it may be placed at the end of the PEG chain on the liposomal surface, hence the ligand will be attached to the distal end of the PEG chain after the formation of liposomes. Lipids may be first dissolved in an organic solvent, then dried until a lipid film forms. The drying condition can depend, for example, on the volume of the sample and the solvent used. After that, the lipid film may be hydrated with a suitable material (e.g., distilled water or the encapsulating material), and this may lead to the formation of multilamellar vesicles (MLVs) liposomes. In order to convert it to unilamellar vesicles (ULVs), several techniques for applying mechanical stresses may be used including sonication or extrusion. Subsequently, the liposomes may be purified to get rid of unreacted substances and formed micelles, for example, by gel chromatography, based on size (micelles and other molecules are very small compared to liposomes). This may yield the control liposomes. For the actively-targeted liposomes, one more step may be needed to attach the antibody to the functional groups at the distal ends by a suitable reaction depending on the type of bond, which can be done, for example, with Bendas protocol described herein.

For simple, fast, and clean ligand binding, cyanuric chloride-PEG-liposomes may be used (cyanuric chloride being the functional group). This is because the resulting bond would not damage the antigen binding site on the antibody, thus would not prevent their specific activity. The process may involve non-toxic materials and may not require the pre-modification of the monoclonal antibody.

In certain embodiments, attaching the antibodies to the liposomes directly can prevent their activity and also increase the clearance of liposomes by the reticuloendothelial system (RES), but conjugating antibodies to the distal ends of PEG chains may yield long-circulating, fully functioning immunoliposomes. In some instances, it can also enhance the binding efficiency of the ligand to the liposome.

Materials for the Synthesis of Immunoliposomes

In some instances, dipalmitoylphosphatidyl choline (DPPC) and/or 1,2-distearoyl-sn-glycero-3-phosphoethanolamine-N-[amino(polyethylene glycol)-2000] (DSPE-PEG(2000)-NH2) may be used as phospholipids for the immunoliposomes, in order to prevent chemical degradation by oxidation which could lead to increasing the permeability of the bilayers. Oxidation can also be minimized using high-quality lipids and avoiding high temperatures. The choice of the buffer used, the pH, the temperature, and the charge of the liposome may affect the hydrolysis of the phospholipids.

In some instances, the phospholipids may be selected to have suitable cholesterol molar ratio, which affects the stability of the liposomes. The addition of cholesterol to saturated lipids increases their fluidity (in contrast to unsaturated lipids), and thus gaps that are formed in the lipid bilayers due to the trigger will reclose too soon. But the addition of cholesterol may reduce the phase transition temperature of the lipid mixture.

The ratio of PEGyhlated lipid to non-PEGylated lipid may affect aggregation or accumulation of immunoliposomes, and in some instances, the ratio of PETyhlated lipid to non-PEGylated lipid may be below 6%. In some instances, the ratio of PETyhlated lipid to non-PEGylated lipid may be below about 10%, 5%, or 1%. The length of PEG chain for the PEGyhlated lipid may be selected such that the binding of immunoliposomes to the target may not be prevented or obstructed. The protein density of the liposome may affect affinity of the liposome to its target. In some instances, the protein density may approximately be 7.5-30 molecules per liposome vesicle to yield a strong affinity towards its target.

In certain embodiments, the gel-liquid crystalline phase transition temperature $(T_m)$ of DPPC bilayer is 41° C., while it is 74° C. for DSPE, so the operating temperature for the preparation of liposomes may be between 41° C. and 74° C. In some instances, the operating temperature may be between 45° C. and 70° C., between 50° C. and 70° C. In some instances, the operating temperature may be around 60° C. This is reasonable because the resulting lipid transition temperature ranges from 41 C.° for pure DPPC to 43 C.° for 15% DSPE-PEG (2000) lipid mixture, and the cholesterol helps to lower the transition temperature as well.

In some embodiments, a fluorescence marker may be used as a model drug, instead of doxorubicin, for calcein release experiment, because the latter is highly toxic and significantly more expensive. Also, calcein may be generally used to model hydrophilic drugs, and it is easily dissolved in the lipid solution after adjusting the buffer pH. Some of the materials used in this work and their properties are listed in Table 3.

TABLE 3

| Properties of the reagents used in the synthesis | | |
|---|---|---|
| Material/ properties | Molecular weight (g/mole) | Transition temperature (° C.) |
| DPPC | 734.039 | 41 |
| DSPE | 748.08 | 74 |
| DSPE-PEG (2000)-NH2 | 2790.486 | — |
| cholesterol | 386.65 | — |
| Trastuzumab | 145531.5 | — |

Preparation of DSPE-PEG-NH$_2$ Control Liposomes

In some embodiments, control liposomes may be prepared using cholesterol, DPPC, and DSPE-PEG(2000)-NH$_2$ at molar ratios of 30:65:5, respectively. The dipalmitoylphosphatidyl choline (DPPC) and 1,2-distearoyl-sn-glycero-3-phosphoethanolamine-N-[amino(polyethylene glycol)-2000] (DSPE-PEG(2000)-NH$_2$) may be obtained from Avanti Polar Lipids Inc. (Alabaster, AL, USA). Cholesterol may be obtained from AlfaAcsar (Ward Hill, MA, USA). The reagents may be dissolved in 4 ml chloroform to a final concentration of around 5-20 mg lipid/ml solvent in a round-bottom flask at 60° C. Chloroform may be obtained from Panreac Quimica S.A. (Spain). In some instances, the final concentration may be 10 mg/ml. Then chloroform may be dried in a rotary evaporator under vacuum for 15 minutes, until a thin film was observed on the walls. After that, the lipid film may be hydrated using 2 ml of 30 mM calcein solution and the pH may be adjusted to 7.4. Calcein disodium salt, and the bicinchoninic acid (BCA) kit may be obtained from Sigma-Aldrich Chemie GmbH (Munich, Germany). Then the solution may be sonicated at 40-kHz using 100% power for 15 minutes in a sonicator bath (Elma D-78224, Melrose Park, IL, USA).

The liposomal solution may be then extruded three times using 200-nm polycarbonate filters (Avanti Polar Lipids, Inc., Alabaster, AL, USA). Lastly, for the removal of free calcein and spontaneously formed micelles, purification using size exclusion chromatography on a Sephadex G-100 column was performed, after equilibrating it with borate buffer pH 8.5. Sephadex G-100 may be obtained from Sigma-Aldrich (Sweden). All of the previous steps may be performed at 60° C., and/or above the transition temperature of the lipid. Finally, dense liposome fractions may be collected and either used to prepare immunoliposomes, or stored at 4° C. after changing their buffer to PBS pH 7.4.

Preparation of Sterically Stabilized Immunoliposomes with Antibody-PEG Linkage

Preparation of sterically stabilized immunoliposomes with antibody-PEG may be done in two steps, first modifying the liposomes with cyanuric chloride (C.C.), and then adding the antibody at a pH 8.5 to be linked to the cyanuric chloride. Liposomes prepared as described above made be used here for the modification with cyanuric chloride. All the steps may be conducted in an iced bath. First, cyanuric chloride may be dissolved in acetone to make a 10 (mg/ml) solution. Then, 9.23 μl of that solution may be diluted in 0.5 ml di-ionized water, because alcohol may be destructive to liposomes. The diluted solution may be added to 1 ml liposomes solution, to achieve 1:1 molar ratio of cyanuric chloride to DSPE-PEG-NH2 respectively. The reagents may be stirred at pH 8.5 and 0° C. for 3 hours to allow for the nucleophilic substitution of chloride particle on the cyanuric chloride with the proton on the NH2 group on liposomes. Then after that, trastuzumab may be added in excess amounts (e.g. 1 mg) after being dissolved in 0.5 ml borate buffer (pH 8.5). This reagents with trastuzumab may be kept stirring overnight to allow to reach completion, where the N-terminus on amino acids of the trastuzumab may be linked to cyanuric chloride. Subsequently, the liposomes may be purified to remove excess trastuzumab and any free calcein in a Sephacryl S-200 HR column equilibrated with PBS (7.4 pH) and eluted with PBS (pH 7.4). The liposomes may be collected and stored at 4° C. until use.

Determination of Size of Liposomes

Size distribution of immunoliposomes may be determined in several ways, including, but not necessarily limited to, dynamic light scattering (DLS), electron microscopy, or right-angle light scattering and turbidity. For example, the mean size of liposomes may be determined at room temperature by DLS using DynaPro® NanoStar™ model from Wyatt Technology Corp. (Santa Barbara, CA, USA). Viscosity and concentration of liposomes may be measured as parameters, considering a medium viscosity of 1.020 and medium refractive index of 1.333.

First, the liposome samples may be diluted with PBS pH 7.4 and filtered using 450-nm PVDF disk filters, then placed inside the machine for analysis, where a laser is directed toward the sample. The machine may detect fluctuations in the intensity of the light scattered, due to movement of particles. This intensity may differ for large particles compared to smaller ones, and based on a previous calibration process, measurements of size distribution can be obtained. Acceptable readings may correspond to <20% poly dispersion (PD) and the relatively low sum of squares (SOS), which may be all shown on the software used. Data obtained from the software may be analyzed using two fits: cumulant and regularization. Cumulant fit analysis assumes the presence of one model, i.e. a uniform size distribution, however, this may be unlikely, since possible existence of micelles or other impurities. Therefore, the regularization fit may be used, and the particles may be assumed to behave as multimodal particles distribution.

Zeta Potential Determination

Zeta potential determination measures the magnitude of the charge on the particle surface. The measurement may be done using electrophorectic mobility of dispersion using a Zetasizer 3000 HSa equipment. Zeta potential with values between 25 mV and −25 mV indicate the tendency for particle aggregation due to Van Der Waal inter-particle attractions. Values outside this range indicate the stability of the nanoparticle. The zeta potential may indicate the successful modification of the nanoparticles surface. Control liposomes may indicate negative values due to the presence of the hydrophilic PEG polymers, but actively targeted liposomes may counteract the charge of the PEG polymer resulting in an increase in the zeta potential (towards the positive direction) if the binding process was successful.

Liposome Concentration Quantification

Liposome Concentration may be determined using a Stewart assay. In Stewart assay, the detection of phospholipids may be based on complex formation between ammonium ferrothiocyanate and phospholipids, which may be detectable in spectra at 485 nm. The complex is insoluble in chloroform, whereas the phospholipids are. Mixing ammonium ferrothiocyanate and phospholipids, and separating the phases may result in a lower layer of chloroform in which the complex formed is dissolved in, and an upper layer of the remaining. Detecting the spectra absorption of the lower layer after separation may indicate the phospholipids concentration in the sample. The assay may be sensitive to small amounts down to 0.01 mg lipids in 2 ml chloroform (0.005-0.05 mg/ml). Diluted samples can be used if needed and then the results can be adjusted with the dilution factor.

A calibration curve for the DPPC may be prepared with increasing concentrations from 0.0025 (mg/ml) to 0.025 (mg/ml). The liposomes samples may be dried in vacuum and then dissolved in chloroform, with a dilution factor of 20. Then the solution may be sonicated to properly dissolve and break the liposomes to its constituent lipids. Six replicates may be made by adding specific amounts of lipid samples to 2 ml ammonium ferrothiocyanate. Then the mixtures may be vortexed for 20 seconds for proper mixing. And after that, the mixtures may be centrifuged to separate the chloroform layer. Subsequently, the light absorption at 485 nm may be read using a spectrofluorometer and results may be used to calculate the DPPC concentration in each sample. An average of the six measurements may be taken. Liposomes may be formed mainly by DPPC so the amount of the NH2-PEG-DSPE lipids may be safely neglected.

Antibody Conjugation Confirmation Using BCA Assay

Protein conjugation efficiency may be determined in several ways, including, but not necessarily limited to the BCA assay (Smith assay), Lowry protein assay, Bradford protein assay (spectroscopic analytical procedure) or biuret test. BCA compared to Lawry assay may be simpler and allow for more flexibilities. And BCA may be more objective than Bradford assay since at higher temperature peptide bonds begin to take part in the reactions. The BCA assay is based on two-step reactions. The first is the reduction of copper $Cu^{2+}$ to $Cu^{1+}$ upon interacting with amino acids and peptide bonds. The second is a change in color from green to purple upon interacting with BCA reagent. This purple colored complex may highly absorb light at 562 nm. The amount of reduced copper may be proportional to the amount of protein in the sample.

In certain embodiments, using the micro BCA assay, to determine total protein concentration in a solution, working reagents A, B, and C may be added together at molar ratios of 25:25:1, respectively. One milliliter of the resulting solution may be added to one milliliter of the buffer (e.g. PBS) and 100 μL of the sample (liposomes solution). Then, they may be mixed for 30 seconds using the vortex machine, and subsequently incubated at 60° C. for 1 hour. A calibration curve to compare the absorption spectra with protein solutions of known concentrations can give direct concentration measurements.

Conjugation efficiency can be determined as the ratio of the amount of protein in immunoliposomes after purification to the ones before purification. Sometimes purification may not be 100% efficient, such that some free antibodies that were not attached can be detected in the assay. To overcome that, control liposomes may be prepared by simply mixing them with the antibody without performing the reaction, and then they can be purified. The difference in the protein amount between the two samples (control liposomes and immunoliposomes) may indicate the number of attached antibodies, not the free ones. Six replicates per liposome batch may be used to confirm the amount attached. The procedure may be repeated for three batches of liposomes to confirm the attachment and the consistency of the results.

Evaluation of Formulation Morphology by Transmission Electron Microscopy (TEM)

First, the sample may be placed onto a copper grid coated with a carbon membrane. Then excess liquid may be removed after two minutes to allow for adsorption. Then the sample may be dried at room temperature. For negative staining, a drop of 1% (w/v) aqueous solution of uranyl acetate may be added. The surface morphology may be analyzed in a JEOL 2010 TEM with 100 kv accelerating voltage.

Cytotoxicity

In determination of cytotoxicity of nanocarrier carried drugs, trypan blue may be used to distinguish between viable and dead cells. Viable cells membranes are very selective and do not allow the penetration of the Trypan blue dye inside the cells, in contrast to dead cells that do. To quantify cells uptake and determine the binding of immunoliposomes to cells, flow cytometry will be used. First, two types of cell lines (normal breast cells and HER2 overexpressing breast cancer cells) may be cultured in 6-well plates. Then, they may be incubated with the liposomal solution at 37° C. for 1 hr. The wells will be trypsinized and centrifuged and finally washed with PBS to remove floating unbounded liposomes, and analyzed in a flow cytometry.

Determination of the Number of Trastuzumab Molecules Attached to Each Liposome

The number of antibody molecules attached to each liposome may be determined assuming an average radius of liposomes of about 100 nm, which indicates that each liposome vesicle have around 80,000 phospholipid molecules. With the knowledge of the molecular weight of trastuzumab and DPPC, the number of trastuzumab molecules per vesicle can be calculated after quantifying the protein and lipids amounts using BCA assay and Stewart assay.

Release Experiments

Calcein release rate may be dependent on multiple factors, including but not limited to liposomes composition, fluidity, permeability, and bending elasticity. Upon US triggered drug release, the release can be affected by multiple factors, including but not limited to the mode of operation, the power intensity, the duration of the pulse, and liposomes composition, gas encapsulated, and concentration in the sample. Thus, various power densities may be tested to achieve optimal drug release. As described elsewhere in the specification, it has been reported that the release at LFUS obtained better results than HFUS. For example, release at 20 kHz may be superior to 1 MHz and 3 MHz.

Continuous Release Experiments Using Phosphorescence/Fluorescence Spectrofluorometer To trigger the release of the calcein, a model for hydrophilic drugs, from liposomes, 20-KHz LFUS may be used. The amount released can be quantified by fluorescence changes using QuantaMaster QM 30 Phosphorescence Spectrofluorometer (Photon Technology International, Edison NJ, USA). Calcein is a fluorescence molecule and has an excitation and emission wavelengths of about 495 and 515 nm, respectively. It may be used as an indicator for the liposomal leakage and drug release as follows: when it is encapsulated in a fluorescent quenching concentrations (≥30 mM), no fluorescent can be detected, but upon releasing to the aqueous surrounding solution due to acoustically trigger release, it is diluted and the release can be measured by monitoring the increase in fluorescent. Calcein fluorescence is dependent on pH at acidic conditions (pH<4.5), but independent at pH values ranging between 6.5 and 10. Release experiments may be conducted at a pH of 7.4.

The synthesized liposomes may be diluted using a solution of PBS at a pH of 7.4 in a fluorescence cuvette and placed inside the spectrofluorometer. For ultrasound exposure, 20-kHz ultrasonic probe (model VC130PB, Sonics & Materials Inc., Newtown, CT), may be inserted 2 mm in the cuvette, such that it does not cross the path of the emitted light through a special opening in the spectrofluorometer. Then, for data normalization, the initial fluorescence concentration ($F_o$) may be measured for 60 seconds before sonication. Then, ultrasound may be applied in a pulse mode, with 20 seconds "on" and 10 seconds "off" periods, until fluorescence concentration plateaus.

To normalize release, 2% (w/v) Triton X-100 may be added to achieve a final concentration of 0.48 mM. The surfactant may be used to lyse the liposomes and fluorescence concentration ($F_1$) to achieve 100% release may be monitored. These steps may be repeated for three different power settings (20%, 25% and 30%), corresponding to three different power densities 7.46, 9.85, and 17.31 (mW/cm$^2$). To calculate the dimensionless fluorescence concentration at a given time, the following equation may be used:

$$\text{Cumulative fraction of drug released } (CFR) = \frac{F_t - F_0}{F_1 - F_0} \quad \text{Eq. (1)}$$

The data for three batches of liposomes, with three replicates may be collected for each run.

Statistical Analysis

Means and standard deviations of release may be calculated for both control liposomes and the targeted ones. Pairwise comparisons may be performed using ANOVA tests. Based on the assumption that both populations having similar variances, two values may be considered significantly different if $p<0.05$ and if $F<F_{critical}$ (unless otherwise stated).

Particle Size Measurements by DLS

Liposome size (e.g., the size of control and/or targeted immunoliposomes) may be determined by DLS as described herein, to ensure the formation of liposomes and to ensure that they are almost uniform. A polydispersity (Pd) upper limit of 20% is generally acceptable in the measurements. Table 3 summarizes the averages of the three batches with their standard deviation for both types of liposomes. As shown in Table 4, radii of both liposomes (i.e. NH2 liposomes without antibody; and immonoliposomes) fall within the range of SLVs and they are within the optimal range for the EPR effects to take place, as previously discussed.

A slight increase in radius after the attachment of trastuzumab is noticed with the radius going from 89.54 nm to 101.10 nm for NH$_2$ liposomes and immunoliposomes, respectively. This may be due to the size of trastuzumab molecules and their attachment to the distal end of the liposomes. Accordingly, this increase in radius may confirm the attachment of trastuzumab. In some instances, the immunoliposomes may have mean radius between 50-150 nm, 80-120 nm, or 90-110 nm.

TABLE 4

Summary of DLS Results

| Liposomes | Radius (nm) | Pd % |
|---|---|---|
| NH2 liposomes | 89.5417 ± 0.4964 | 11.2750 ± 1.1144 |
| immunoliposomes | 101.1032 ± 1.1345 | 17.2190 ± 2.3390 |

A single ANOVA analysis has been conducted between the radiuses of the NH2 liposomes and the immunoliposomes. Results in Table 5 show an extremely high value of F compared to F critical and a value for p-value lower than the standard alpha value (0.05), indicating that the two types have different radiuses.

TABLE 5

Single-factor ANOVA analysis of radius measurements.

| Source of Variation | SS | df | MS | F | P-value | F crit |
|---|---|---|---|---|---|---|
| Between Groups | 725.0768 | 1 | 725.0768 | 66.73175 | 8.43E−08 | 4.351244 |
| Within Groups | 217.3109 | 20 | 10.86555 | | | |
| Total | 942.3877 | 21 | | | | |

Trastuzumab Attachment Confirmations

In order to confirm the attachment of the mAb Trastuzumab to liposomes, the BCA assay and Stewart assay may be used as described herein. The BCA assay may be used to determine the concentration of protein in the sample (µg/ml), while the Stewart assay may be used to determine DPPC concentration in the sample (mg/ml). Combining the two methods, a w/w ratio of protein to lipids in (µg/mg) may be obtained, thereby excluding the effect of different concentrations alterations. The results for three batches of liposomes may be averaged to confirm attachment consistency and standard deviation.

Also, the number of liposomes attached per each liposomes vesicle may be calculated. As described herein, the control liposomes are NH2 liposomes that are mixed with the antibody but without performing the attachment reaction. The control liposomes may be purified using the same purification column of that of immunoliposomes, to confirm that any increase in the protein level is only due to attached trastuzumab. Any difference in protein level can be considered due to the presence of attached Trastuzumab.

Figure 4:
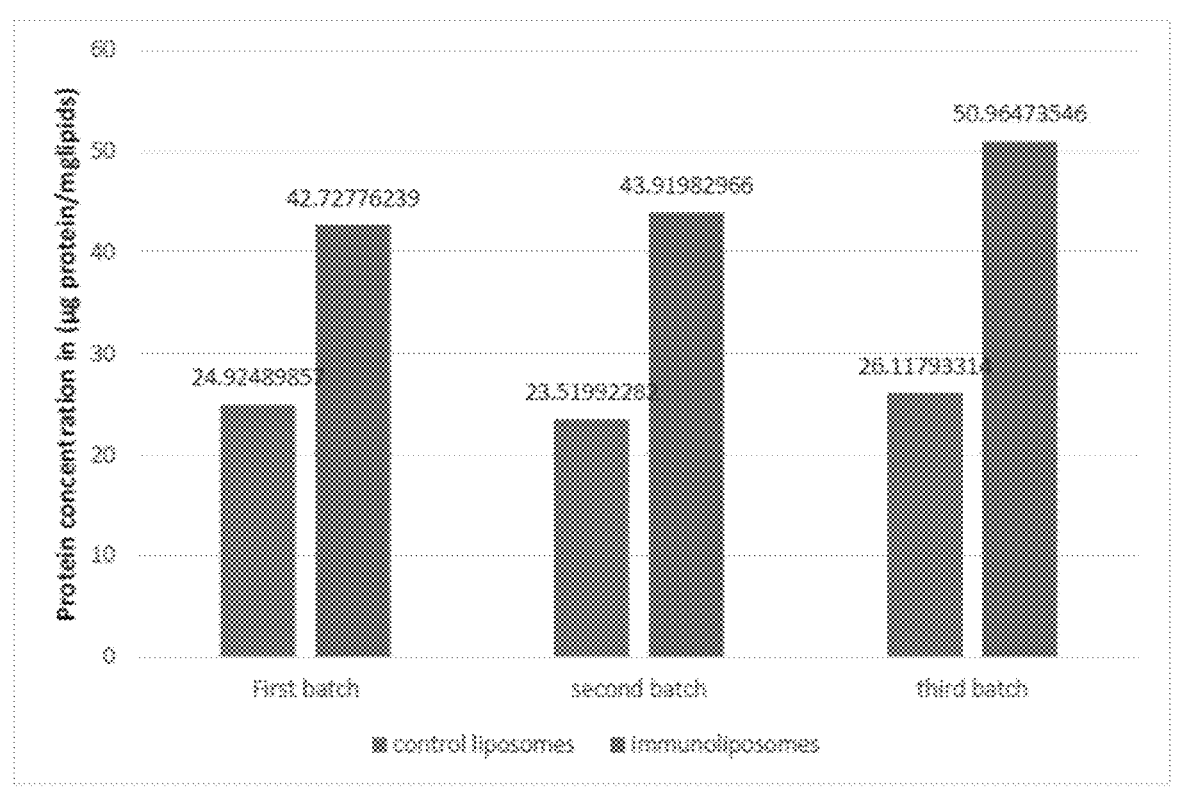
FIG. 4 illustrates an embodiment of protein levels for control liposomes and immunoliposomes.

The summary of the results of the Stewart assay, the BCA assay and the calculated protein level for each batch of liposomes produced according to some embodiments as described herein are shown in Tables 6-8, respectively. Additionally, FIG. 4 illustrates protein concentrations per mg lipids for control and immunliposomes in each of the three batches. In FIG. 4, the increase in the protein level for immunoliposomes is shown, confirming the antibody attachment to immunoliposomes. The consistency of results can also be observed from batch to batch, with w/w protein to lipids ratio is about 1:48 in immunoliposomes.

Also, as shown in Tables 5-7, both the control liposomes and immunoliposomes may have approximately the same lipids concentration, which is expected because they were both made following the same procedure except instead of adding cyanuric chloride with acetone.

Additionally, the protein level increase was found to be a critical function of the cyanuric chloride added, in which can be shown for the last batch where a slight increase of about 2 µl resulted in slightly higher protein amount. However, cyanuric chloride addition may be controlled to prevent the homopolymerization of mAb-mAb or the possibility of the liposome-liposome attachment.

TABLE 6

Trastuzumab attachment results summary for batch 1

| | µg protein/ml | mg lipids/ml | µg protein/ mg lipids |
|---|---|---|---|
| control liposomes | 69.6179 | 2.7931 | 24.9249 |
| immunoliposomes | 121.4786 | 2.8431 | 42.7278 |
| Trastuzumab | | | 17.8029 |

TABLE 7

Trastuzumab attachment results summary for batch 2

| | µg protein/ml | mg lipids/ml | µg protein/ mg lipids |
|---|---|---|---|
| control liposomes | 76.8071 | 3.2656 | 23.5199 |
| immunoliposomes | 147.4385 | 3.3570 | 43.9198 |
| Trastuzumab | | | 20.3999 |

TABLE 8

Trastuzumab attachment results summary for batch 3

| | µg protein/ml | mg lipids/ml | µg protein/ mg lipids |
|---|---|---|---|
| control liposomes | 78.5010 | 3.0056 | 26.1179 |
| immunoliposomes | 172.7090 | 3.3888 | 50.9647 |
| Trastuzumab | | | 24.8468 |

For the Stewart assay for measurements of lipids concentrations, lipids solutions absorb light at 485 nm as described herein, and a calibration curve of known concentrations of DPPC in mg/ml versus absorbed spectra was constructed. Samples were compared against that curve, and each spectra value was converted to a concentration. Six replicates per batch were used for both types of liposomes. This calibration curve was linear which allowed for more accuracy and flexibility in calculations.

Similar procedure was adopted when running the BCA assay, where a calibration curve was first constructed for known trastuzumab solution concentrations. Then each sample spectra was compared against that curve to a yield the protein concentration in µg/ml. The protein sources in the samples were the amino acids in the antibody and the peptide ponds in the liposomes themselves. To account for that difference, protein concentrations for the control liposomes were measured as well. Therefore, the difference in protein amounts could be attributed only to the amino acids in the attached trastuzumab. This is feasible because of the linearity of the calibration curve, where the protein concentration can be additive and subtractive. Additionally, the nature of the control liposomes accounted for the calculation of attached mAb only. Some of the subtracted protein was due to the presence of free trastuzumab in that sample, leaving only the effect of protein coming from attached trastuzumab.

Assuming a liposome size of 100 nm in radius and an average area for a single phospholipid molecule of about 75 A°, the average number of lipid molecules constructing a single liposomes vesicle may be 80,000. Knowing the concentrations of the lipids and trastuzumab and their molecular weights, it was found that almost 9 trastuzumab molecules were conjugated per liposome vesicle. This is considered to fall within the optimal range that may induce sufficient cell cytotoxicity. In some embodiments, each immunoliposome may have about 1, 2, 4, 6, 7, 8, 10, 11, 12, 14, 18, 24, 30, 50, or more than 50 trastuzumab molecules conjugated to the liposome vesicle.

Mechanical Index Calculations

Mechanical index is a measurement of likelihood of cavitation and damage to cells and tissues, as described herein. At different mechanical indexes, different effects may start to happen. For example, for collapse cavitation to start, the mechanical index has to reach 0.3, and for biological effects, it has to reach 0.6. Tissue damage begins at a mechanical index of 1, where the limits set by the Food and Drug Administration (FDA) is MI=1.9. The following formula is used to calculate the MI.

$$MI = \frac{p^-\,[\text{Mpa}]}{\sqrt{f\,[\text{MHz}]}} \qquad \text{Eq. (2a)}$$

Where $P^-$ is the negative pressure in [Mpa], and f is frequency in [MHz].

The negative pressure can be calculated using the acoustic impedance of water which is 1.48 (MPa·s/m) and the intensity. This is shown in equation below.

$$P = \sqrt{2Iz}\,[\text{Pa}] \qquad \text{Eq. (2b)}$$

Where 1 is power density in power density in W/m² and z is acoustic impedance of water in [Pa·s/m].

It is well noticed that the power densities and frequencies calculated correspond to mechanical indexes of 0.11, 0.12, and 0.16 for power densities of 7.46, 9.85, and 17.31 (mW/cm₂) respectively. In certain embodiments, the power density may be at least about: 2, 4, 6, 10, 14, 18, 20, 24 30, 40, 50, or more than 50 (mW/cm2). These values are well below the safe limits of any biological effects. It can be concluded that higher power densities, up to 60 mW/cm² which corresponds to a mechanical index of 0.3, can be safely implemented when using a frequency of 20 kHz ultrasound.

Low-Frequency Ultrasound (LFUS) Release Studies

As described herein, the ultrasound release experiments may be conducted at 20 kHz, and at three power densities, 7.46, 9.85, and 17.31 mW/cm². Pulsed ultrasound at 20 seconds on and 10 seconds off may be used for a total duration of 6.3 minutes, corresponding to an actual duration of 4.2 minutes. In some embodiments, the ultrasound may be pulsed for a total duration of at least about 2 minutes, 4 minutes, 6 minutes, 10 minutes, 14 minutes, 18 minutes, 20 minutes, or more than 24 minutes. As calcein is released, an increase in fluorescence level should be observed. The baseline at before sonication may be measured for 60 seconds before pulsed sonication was initiated. Then sonication may be applied until a plateau was reached. After that, a sharp increase in the fluorescence level may be noticed when liposomes were lysed to spill all their contents. Finally, the data may be normalized using equation (1). For both types of liposomes (the control and immunoliposomes), three batches may be used, with three replicates measurements for each batch.

The control liposomes used in the LFUS studies may be the $NH_2$ liposomes but the buffer may be lowered from pH 8.5 to pH 7.4. Buffer changing may be done, for example using the purification column. Immunoliposomes may go through the conjugation process before changing the buffer to pH 7.4.

Low-Frequency Ultrasound Release Studies for $NH_2$ Liposomes

Figure 5:
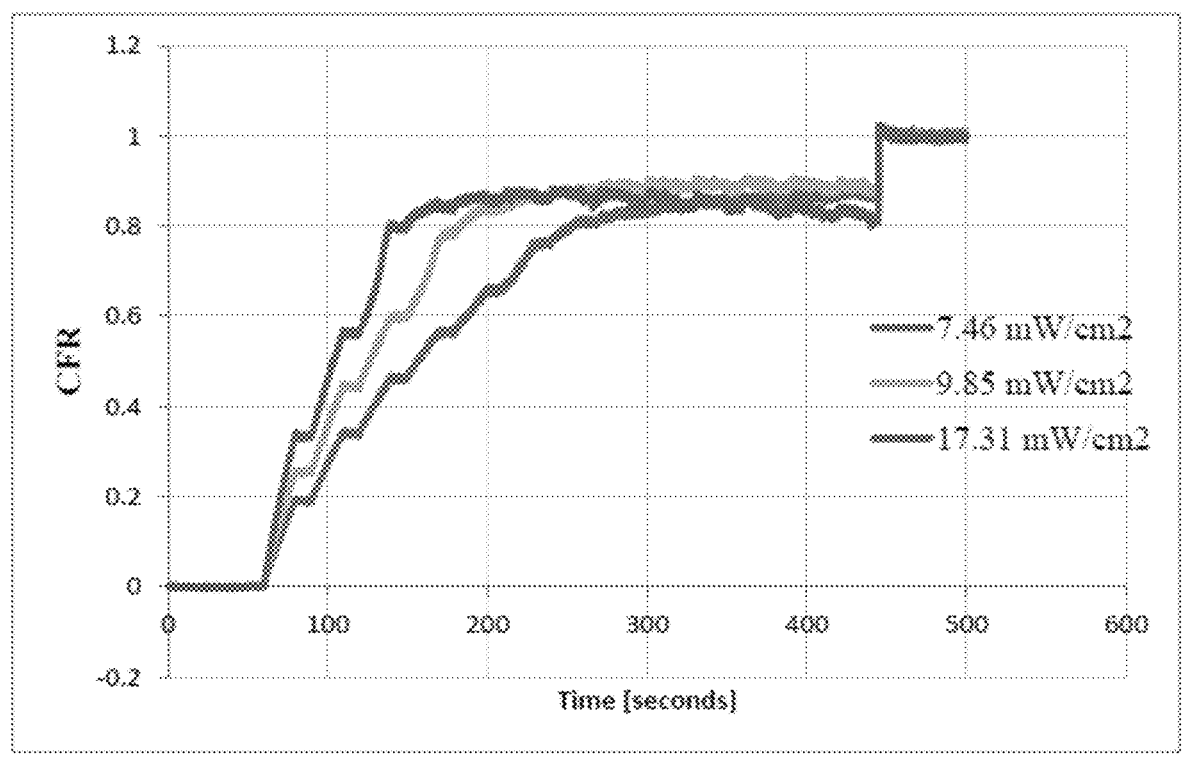
FIG. 5 illustrates an embodiment of release profiles for $NH_2$ liposomes triggered by ultrasound.

FIG. 5 illustrates the average cumulative fraction release data (CFR) for the three batches, for each power density. $NH_2$ liposomes calcein release at LFUS and relatively low intensities may be established, as shown in FIG. 5. This may be beneficial, as LFUS can be used to penetrate further into the human body than HFUS. Also, high-intensity ultrasound can cause unwanted effects such as hyperthermia.

As shown in FIG. 5, the release rate may become steeper as the power density increases; this is expected due to the increase in cavitation events as the power density increases. Also, $NH_2$ liposomes may release most of all their contents (86.35%) within 3 minutes, which demonstrate their sonosensitivity. In conclusion, the release rate may be dependent on both the power density and exposure time.

Also, as shown in FIG. 5, as sonication stops, the release may also cease with no or substantially no delay, and any events occurring upon sonication may disappear immediately. This may support the occurrence of stable cavitation (mechanical effects), rather than thermal effects at LFUS, since low-intensity ultrasound was used and no increase in temperatures was measured. The possible mechanism can be that LFUS causes pore-like defects in the liposomes membrane upon exposure, which then heals immediately in off periods.

As shown in FIG. 5, the release may be accumulative, such that the drug can be released continuously, or pulsed, resulting in the same CFR (after the same exposure time). This may be important for the control of the hyperthermia effects upon the continuous exposure to ultrasound.

As summarized in Table 9, in one embodiment, $NH_2$ liposomes released almost 86.35% of their content after 140 seconds (7 pulses) of actual sonication at 7.46 ($mW/cm_2$), 100 seconds (5 pulses) at 9.85 ($mW/cm_2$), and 60 seconds (3 pulses) at 17.31 ($mW/cm_2$). It has been reported that liposomes with no sonication may release about 3% of their contents in 3 minutes. Higher release rates may be attributed to more cavitation events. Table 9 also shows the range of ultrasound parameters that can be selected to achieve a specific release rate.

TABLE 9

| Release data summary of NH2 liposomes showing total release CFR at the plateau | | | |
| --- | --- | --- | --- |
| Power density (mW/cm2) | CFR at Plateau | Pulses to reach plateau | Time to reach plateau (seconds) |
| 7.46 | 0.8530 | 7 | 140 |
| 9.85 | 0.8820 | 5 | 100 |
| 17.31 | 0.8554 | 3 | 60 |
| average | 0.8635 | | |

Figure 6:
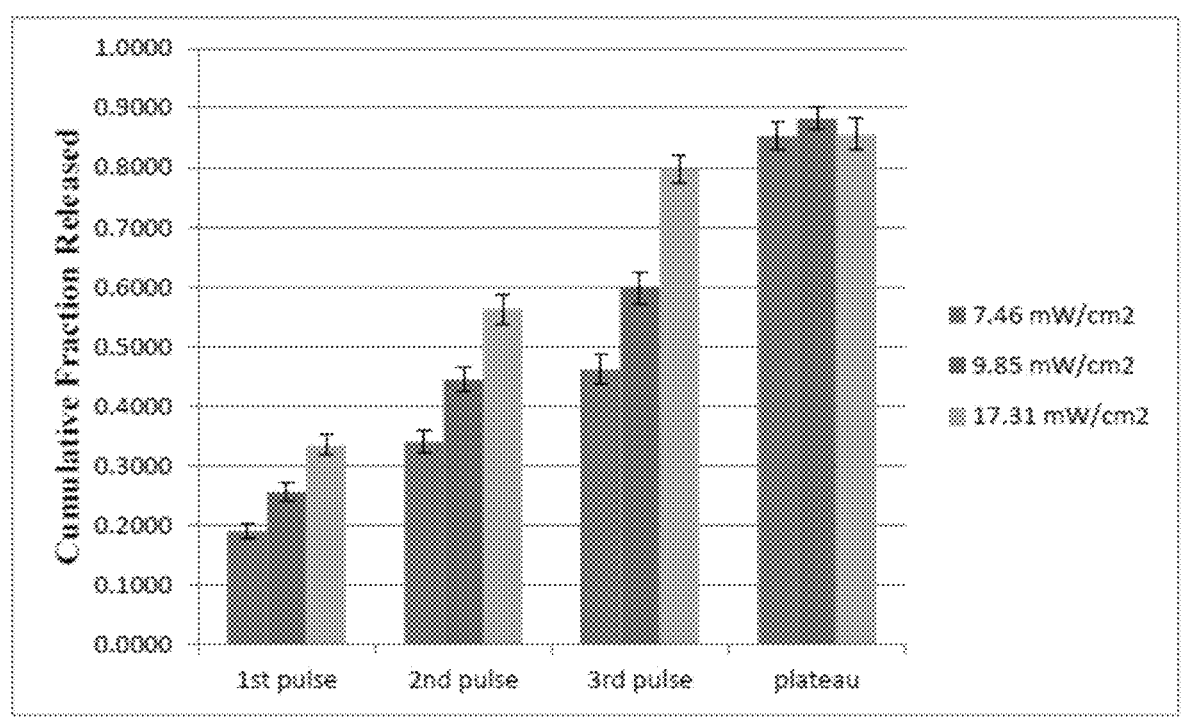
FIG. 6 illustrates an embodiment of the cumulative fraction released measured at different pulses and the final plateau for $NH_2$ liposomes.

FIG. 6 illustrates CFR measured at different pulses, and the final plateau for $NH_2$ liposomes. As illustrated in FIG. 6, the CFR values may increase as power density increases. Also, the amount released after the third pulse for the low power density (7.46 mW/cm²) may be almost 46% of the total drug encapsulated within liposomes, which can occur after 1 minute of actual sonication. In some embodiments, more than 30%, 40% or 50% of the total drug encapsulated may be released after the third pulse for the low power density (7.46 mW/cm²).

Figure 7:
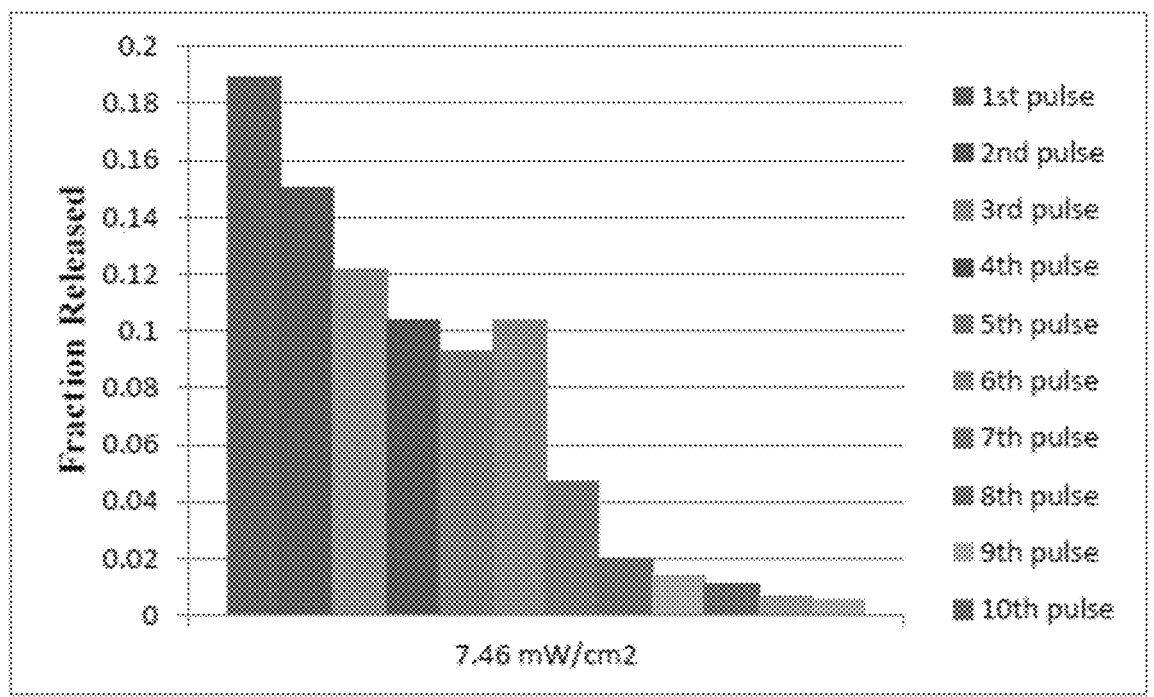
FIG. 7 illustrates an embodiment of fractional release measured at different pulses for $NH_2$ liposomes.

FIG. 7 illustrates the fraction released for each pulse separately (not accumulated) at 7.46 mW/cm². As illustrated, the most fraction released of the drug may be in the first pulse. This may be important in which high initial levels of the drug are needed for biological effectiveness, and then a consequent less amounts to follow to retain that level. In some embodiments, more than 10%, 15%, 20%, 25%, 30%, 40%, or more than 50% of the total drug encapsulated by the liposome may be released after the first pulse. As illustrated in FIG. 7, the plateau may happen after the 7th pulse at which afterwards the release has very low rates. In some embodiments, the plateau may be reached after about 2, 3, 4, 5, 6, 8, or more pulses.

Low-Frequency Ultrasound Release Studies for Immunoliposomes

Figure 8:
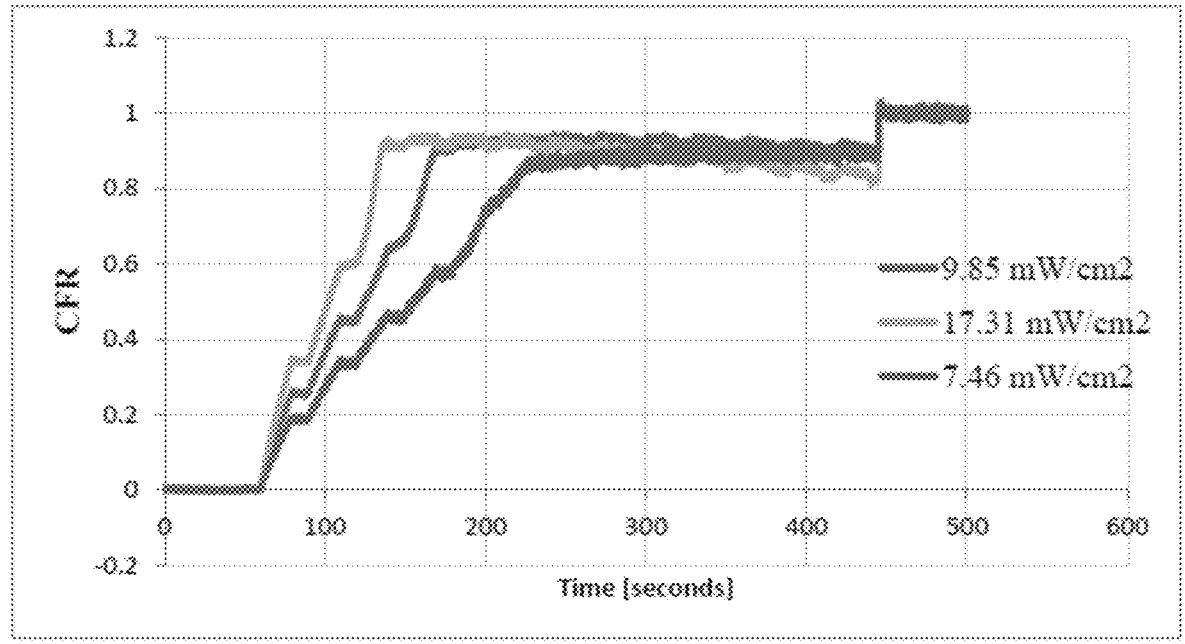
FIG. 8 illustrates an embodiment of a release profile for immunoliposomes triggered by ultrasound.

FIG. 8 illustrates the online release rate of calcein from immunoliposomes at the three power densities, averaged for the three batches of liposomes tested according to one embodiment. As shown in FIG. 8, the almost complete release of the liposomes content (92%) may happened after 6 pulses (120 s), 4 pulses (80 s), and 3 pulses (60 s), for 7.46, 9.85, and 17.31 mW/cm², respectively. The release data is also shown in Table 10. Release upon exposure to ultrasound may be established similarly as described herein in relation to the control $NH_2$ liposomes. As shown in FIG. 8, the release rate in immunoliposomes may increase as power densities increase. Also, release may substantially happen only at exposure to ultrasound, and it may be accumulative. Release may continue for a few seconds in the off period at the highest power density, possibly due to the fact that thermal effects started to occur. At a power density of 17.31 mW/cm², the drug may start to get internalized into the liposomes again after the plateau. The reason could be hyperthermia effects allowing the drug to diffuse back, where liposomes membrane become fragile. Normally, ultrasound exposure may stop before reaching that stage.

TABLE 10

| Release data summary of immunoliposomes showing total release CFR at the plateau | | | |
|---|---|---|---|
| Power density (mW/cm2) | CFR at Plateau | Pulses to reach plateau | Time to reach plateau (seconds) |
| 7.46 | 0.9109 | 6 | 120 |
| 9.85 | 0.9257 | 4 | 80 |
| 17.31 | 0.9246 | 3 | 60 |
| average | 0.9204 | | |

Figure 9:
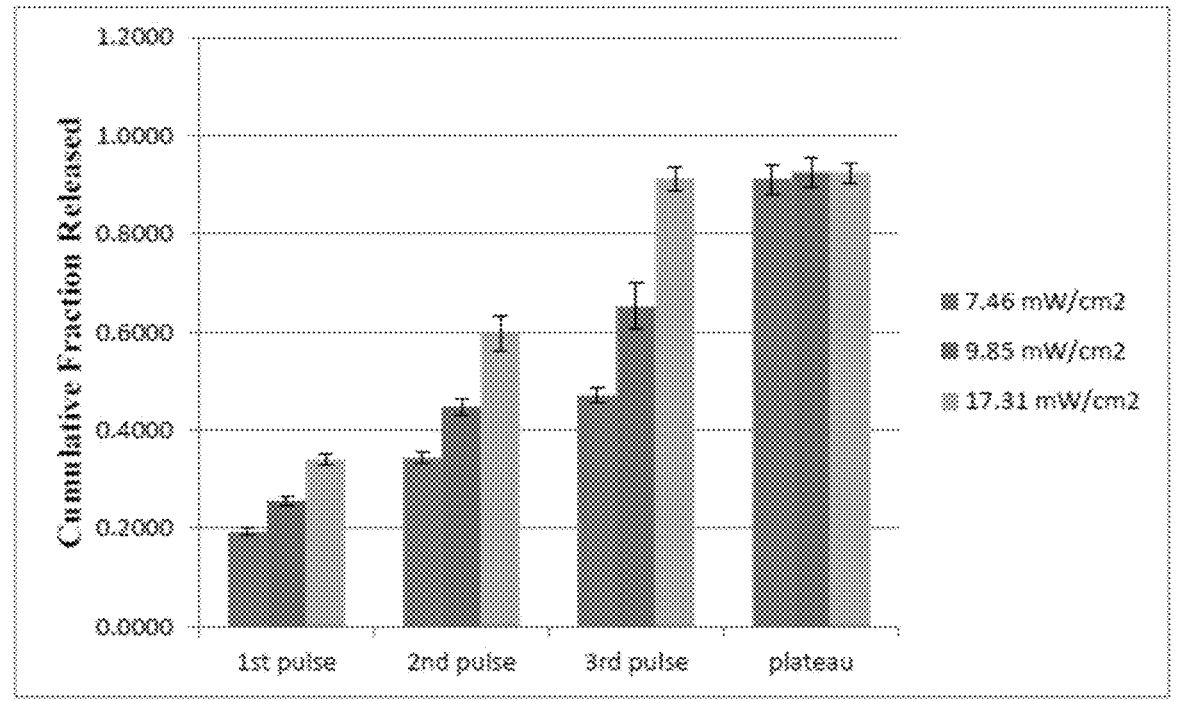
FIG. 9 illustrates an embodiment of cumulative fractions released measured at different pulses and the final plateau for immunoliposomes.

FIG. 9 illustrates CFR measured at different pulses, and the final plateau for immunoliposomes according to one embodiment. As shown in FIG. 9, CFR clearly increase with increasing intensities. After 1 minute, the amount released from immunoliposomes may be 47% at a power density of 7.46 mW/cm$^2$, whereas complete release may be achieved at that same duration for the 17.31 mW/cm$^2$ power density. In some embodiments, more than 30%, 40% or 50% of the total drug encapsulated may be released after the third pulse for the low power density (7.46 mW/cm$^2$).

Figure 10:
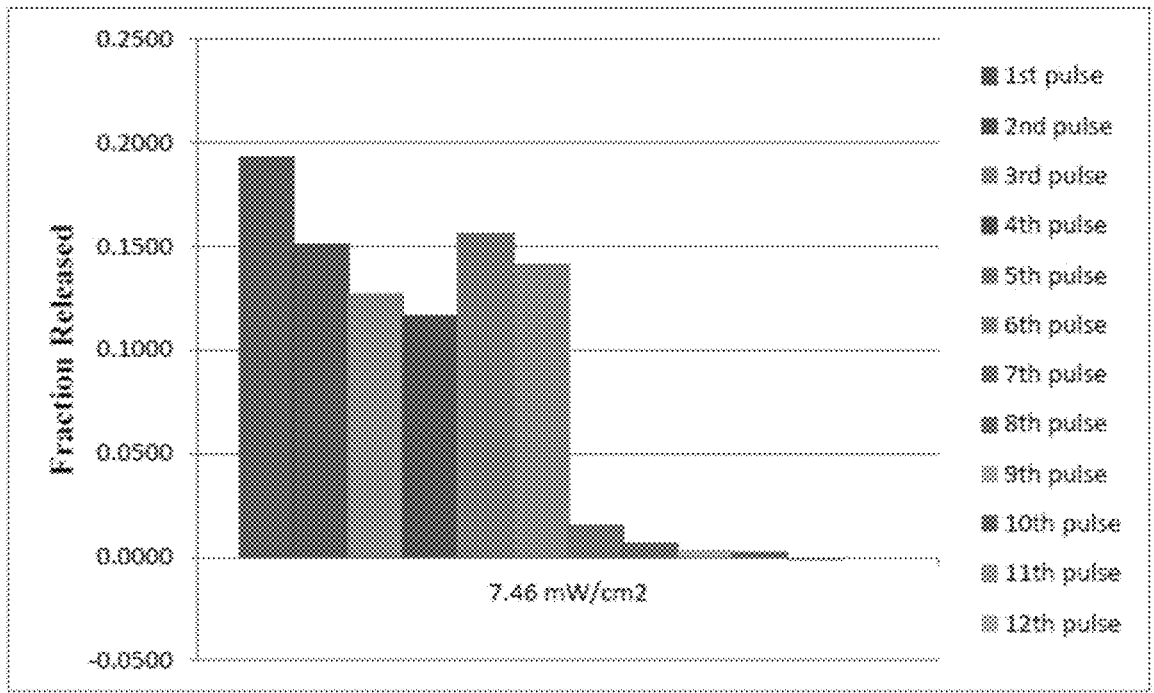
FIG. 10 illustrates an embodiment of cumulative fractions released measured at different pulses and the final plateau for immunoliposomes.
Figure 11:
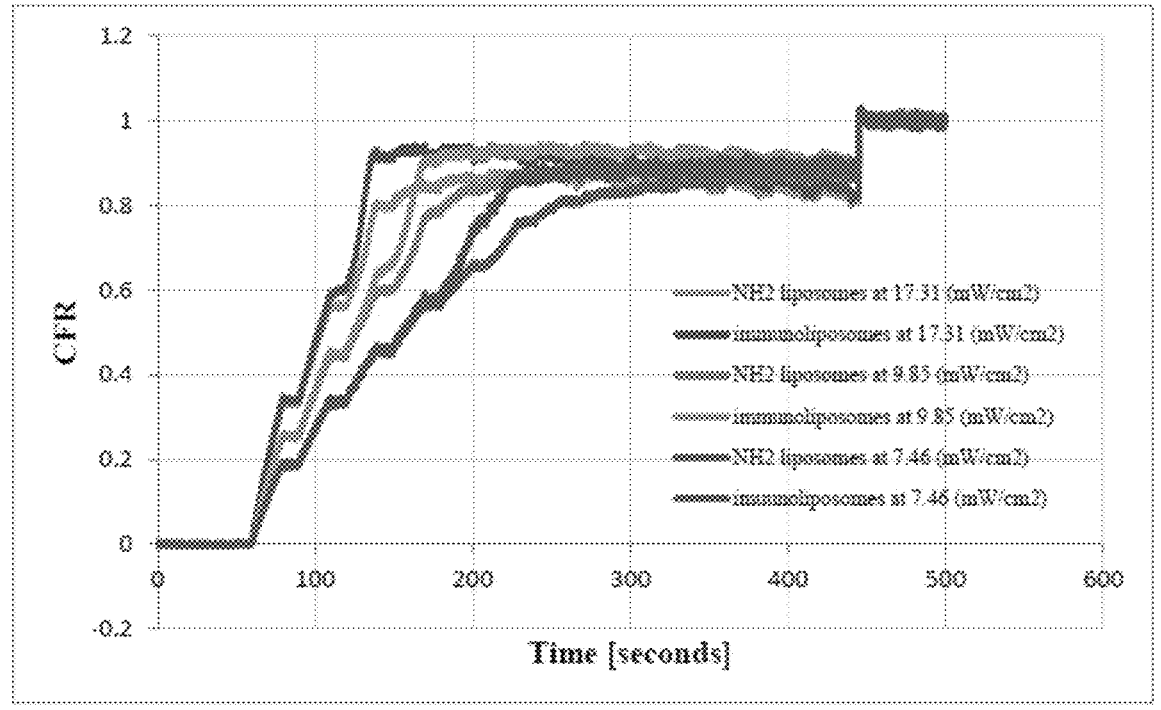
FIG. 11 illustrates an embodiment of a release profile for $NH_2$ liposomes and immunoliposomes at different power densities.

FIG. 10 shows the non-accumulative fraction of drug released at each pulse for 7.46 mW/cm$^2$ for immunoliposomes. As illustrated, the most fraction released of the drug may be in the first pulse. This may be important in which high initial levels of the drug are needed for biological effectiveness, and then a consequent less amounts to follow to retain that level. In some embodiments, more than 10%, 15%, 20%, or 25% of the total drug encapsulated by the liposome may be released after the first pulse. The plateau is shown to happen clearly after the 6th pulse, and incremental release is very low after that. In some embodiments, the plateau may be reached after 3, 4, 5, 7, 8, or more pulses. Comparison Between the NH$_2$ Liposomes and Immunoliposomes Release Rates FIG. 11 illustrates release profiles for NH$_2$ liposomes and immunoliposomes at different power densities according to one embodiment. As shown in FIG. 11, immunoliposomes may have a steeper release profile than the control NH$_2$ liposomes, indicating its sono-sensitivity, which may be beneficial in ultrasound triggered release. This could be used to reach therapeutic levels in shorter exposure times.

Figure 12:
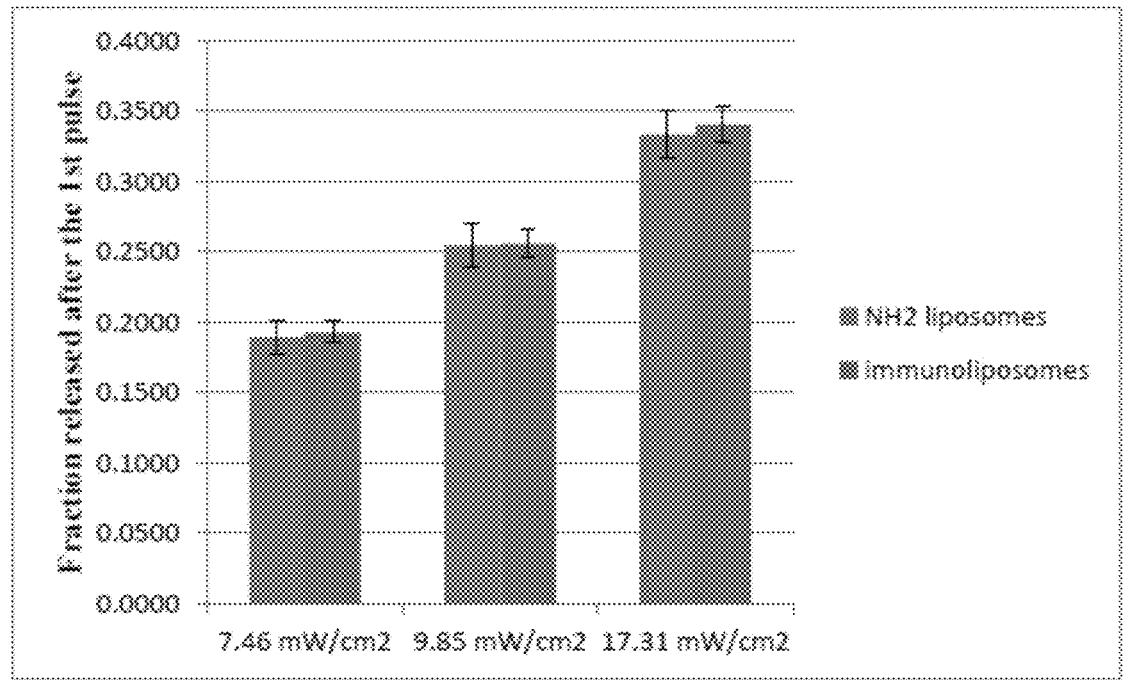
FIG. 12 illustrates an embodiment of fractional release after the first pulse measured for $NH_2$ liposomes and immunoliposomes at each power density.
Figure 13:
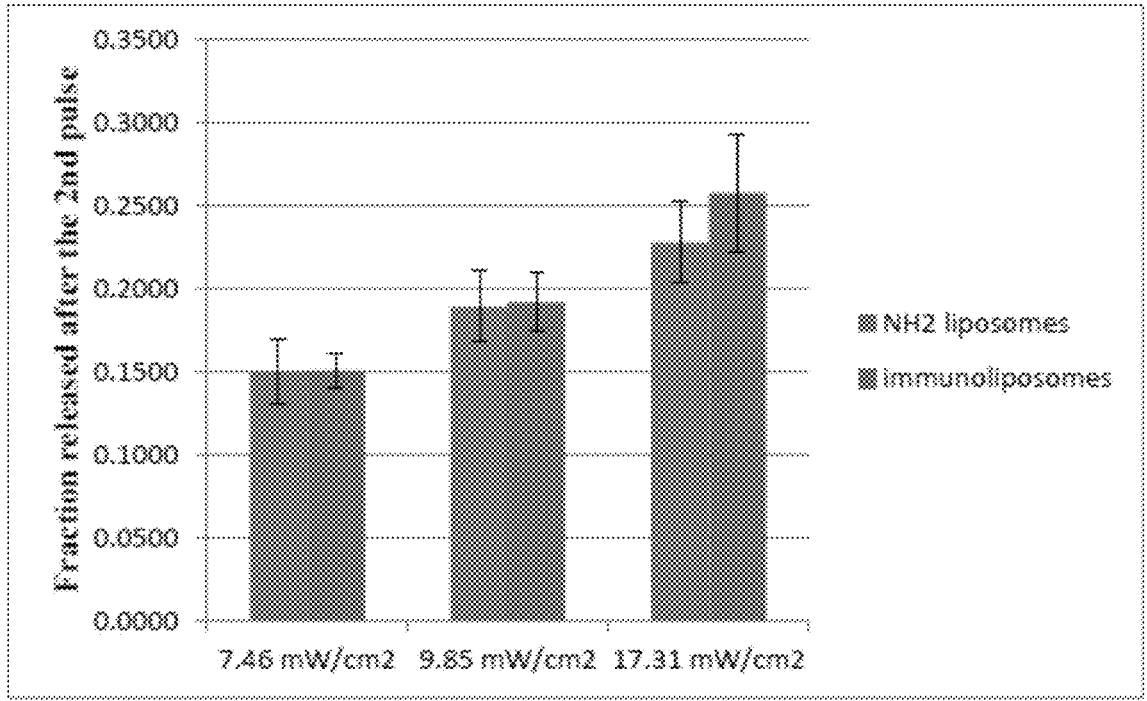
FIG. 13 illustrates an embodiment of fractional release after the second pulse measured for $NH_2$ liposomes and immunoliposomes at each power density.
Figure 14:
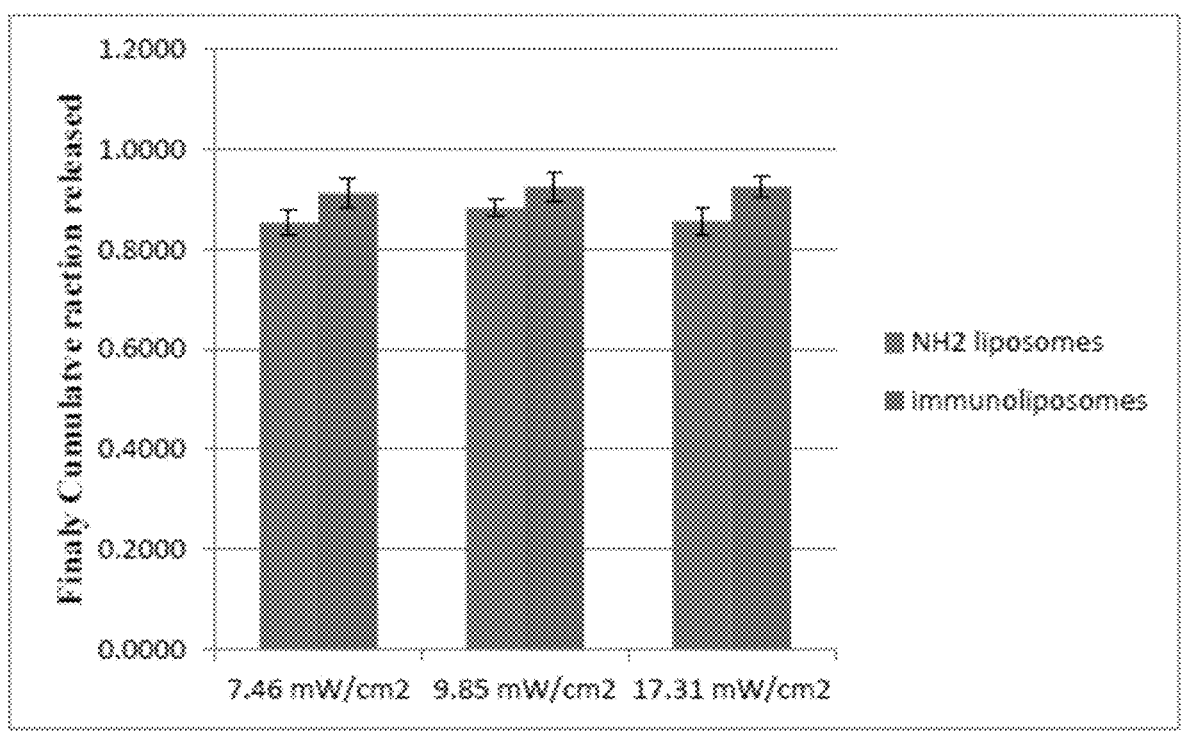
FIG. 14 illustrates an embodiment of the final cumulative fraction released for NH₂ liposomes and immunoliposomes at each power density.

FIGS. 12-13 illustrate fraction released after the first and the second pulse for NH$_2$ liposomes and immunoliposomes at each power density, respectively. FIG. 14 illustrates final cumulative release fraction from NH$_2$ liposomes and immunoliposomes at each power density. As illustrated in FIGS. 12-14, immunoliposomes may have higher drug release amounts after the first pulse, and higher final cumulative amount of drug that liposomes were able to release. For example, immunoliposomes may keep less than 8% encapsulated drug within immunoliposomes, compared to 13% for NH$_2$ liposomes at the end of the sonication period. Release Kinetics Models Modeling the release kinetics may help in predicting release at different conditions including lipid and the agents' composition, power density and frequency. In addition, it may help for the design of equipment to optimize release. The data presented above can be used to find the best fitting model that can successfully represent the calcein release from targeted and non-targeted liposomes. Following models may be used to find the best fitting model.

The zero-order model is derived from a basic understanding of the physical process of tablets, and capsules where the drug is released very slowly at a constant rate. Assuming that the area is constant and no equilibrium conditions are obtained, equation (3) represent the model:

$$Q_t - Q_0 = K_0 t \qquad \text{Eq. (3)}$$

where $Q_t$ represents the amount of drug dissolved in time t; $Q_0$ represents the initial amount of drug in the solution; and $K_0$ represents a zero-order release constant. Rearranging the equation to fit our normalized data, is presented in equation (4):

$$CFR = k_0 t \qquad \text{Eq. (4)}$$

where CFR represents cumulative fraction released; t represents time in seconds; and $k_0$ represents zero-order release constant in percentage per second. A plot of CFR against time will deliver the release constant as the slope.

A first-order model is based on assumption that dissolution includes a surface action. It can be used accurately to model the release of water-soluble drugs in porous matrices. It is mathematically represented by equation (5):

$$\frac{dc}{dt} = -k_1 C \qquad \text{Eq. (5)}$$

where C represents drug concentration at time t; and $k_1$ represents first-order rate constant in seconds$^{-1}$. After integrating and rearranging to make it compatible with the data taken, it yields equation (6):

$$\log CFR = k_1 t + \text{constant} \qquad \text{Eq. (6)}$$

Accordingly, a plot of log(CFR) versus time will yield the slope $k_1$.

Higuchi model describes release as a diffusion based process. Applications of the model include transdermal systems and matrix tablets carrying water-soluble drugs. The model assumes the following: 1) Diffusion is in one dimension only; 2) The concentration of the drug inside the matrix is higher than its solubility; 3) The drug molecules are much smaller than the matrix thickness; 4) Constant drug diffusivity; 5) The matrix change in dimensions is negligible; 6) Perfect sink conditions in the release environment.

The simplified equation for the Higuchi model can be seen in equation (7):

$$Q = k_H \sqrt{t} \qquad \text{Eq. (7)}$$

where $k_H$ represents Higuchi release constant and Q represents amount of drug released in time t. Rearranging to convert Q to CFR yields equation (8), that can be used to obtain Higuchi release constant upon plotting CFR versus square root of time.

$$CFR = k_H \sqrt{t} \qquad \text{Eq. (8)}$$

Korsmeyer-Peppas model is a simple model describing the release from porous hydrophilic polymers. Korsmeyer-Peppas or the power-law as it's sometimes called is a more general model than Higuchi. It takes into account the effects of swelling and dissolution, and it does not assume a diffusion-based release. At small t, the model can be simply shown as in equation (9):

$$\frac{M_t}{M_\infty} = k_{kp} t^n \qquad \text{Eq. (9)}$$

where $$\frac{M_t}{M_\infty}$$

represents the fraction of drug released at time t; $k_{kp}$ represents the Korsmeyer-Peppas release rate constant; and n represents the release exponent. The rate constant changes with different shapes and structures. The exponent value indicates the mechanism of the release. For the case of cylindrical shapes, if $n \leq 0.45$, then the release follows Fick's law (diffusion-dependent), if $0.45 < n < 0.89$ then the release is non-Fickian, if $n = 0.89$ the release follows relaxation transport, and if $n > 0.89$ then the release is considered super case transport. This is why this model is used to study the release when the mechanisms are not known.

After adjusting the model to our type of data and linearizing, equation (10) is realized, and a plot of the log(CFR) versus log(t) can yield $\log(k_{KP})$ as the intersect and the n-value as a slope.

$$\log(CFR) = \log(k_{kp}) + n \log(t) \qquad \text{Eq. (10)}$$

Hixson-Crowell model is based on the proportionality of the sphere regular area to the square root of its volume. The relation can be seen in equation (11).

$$W_0^{1/3} - W_t^{1/3} = k_{HC} t \qquad \text{Eq. (11)}$$

where $W_0$ represents the amount of drug initially inside the liposome; $W_t$ represents the remaining amount of drug in the liposomes; and $k_{HC}$ represents the proportionality constant.

Rearranging the resultant equation to get CFR in one side, yields equation (12).

$$(1 - CFR)^{\frac{1}{3}} = 1 - k_{HC} t \qquad \text{Eq. (12)}$$

This model assumes that release is controlled by the dissolution of the drug particles and not their diffusion through the pores of the matrix. It also takes into account the reduction in the particle size as it dissolved in the solution. Plotting $1 - (1 - CFR)^{1/3}$ versus time should yield a straight line with $-k_{HC}$ as the slope after setting the intercept at 1.

In embodiments, the Baker-Lonsdale model describes the release from spherical matrices by developing the Higuchi model, and the expression is shown in equation (13). The resultant equation when converting the release in terms of CFR is described in equation (14).

$$\frac{3}{2}\left[1 - \left(1 - \frac{M_t}{M_\infty}\right)^{\frac{2}{3}}\right] - \frac{M_t}{M_\infty} = k_{BL} t \qquad \text{Eq. (13)}$$

where $M_t$ represents the drug release amount at time t; $M_\infty$ represents the total amount released at infinite time (initial amount inside the liposomes); and $k_{BL}$ represents the release constant.

$$\frac{3}{2}\left[1 - (1 - CFR)^{\frac{2}{3}}\right] - CFR = k_{BL} t \qquad \text{Eq. (14)}$$

Plotting the left hand equation (14) versus time will result in a straight line with $k_{BL}$ as the slope.

The Weibull model is a general empirical relation that describes different dissolution rates of matrix type systems. The relation is shown in equation (15) and the altered form to incorporate our data is shown in equation (16), whereas the linearized form can be seen in equation (17).

$$m = 1 - e^{\left[\frac{-(t-T)^b}{a}\right]} \qquad \text{Eq. (15)}$$

Where m represents accumulated fraction of the drug; a represents a scale parameter that describes time dependence; b describes shape of dissolution curve; and T accounts for the time lag in dissolution process (taken=0).

$$1 - CFR = e^{\left[\frac{-(t)^b}{a}\right]} \qquad \text{Eq. (16)}$$

$$\log(-\ln(1 - CFR)) = b \log(t) + \log k_w \qquad \text{Eq. (17)}$$

Where $k_w$ is $$\frac{1}{a},$$

and represents Weilbull rate constant. Plotting the expression of equation (17) versus log(t) will yield b as the slope and $\log(k_w)$ as the intersection.

Hopfenberg model assumes that the surface remains constant during eroding. It also assumes that a zero-order mechanism will take place throughout the eroding process, whether the drug was loaded chemically (attached), or physically (dissolved, dispersed). The model considers the diffusion process to be so rapid that it cannot be rate determining. The cumulative fraction released at time t is described by the model in equation (18).

$$\frac{M_t}{M_\infty} = 1 - \left[1 - \frac{k_0 t}{C_L a}\right]^n \qquad \text{Eq. (18)}$$

Where $$\frac{M_t}{M_\infty}$$

represents cumulative fraction released; $k_0$ represents the zero order rate constant describing the eroding; $C_L$ represents the initial drug loading; a represents the system's half thickness (radius for a sphere); and n represents 1, 2, or 3, for a slap, cylinder, and a sphere respectively. Rearranging yields equation (19) in terms of CFR, which is similar to the Hixson-Crowell equation after rearranging. This is not surprising since some relations can reduce to others in special cases. Plotting the left-hand against time will result in a straight line of a lope $k_{HF}$.

$$1 - (1 - CFR)^{\frac{1}{3}} = k_{Hf}t \qquad \text{Eq. (19)}$$

Where $$k_{Hf} = \frac{k_0}{C_L a}$$

Gompertz model is for drugs with good solubility and intermediate release. The relation is exponential, and is shown in equation (20). The model has a sharp increase, which then converges gradually to a plateau.

$$\frac{X_t}{X_{max}} = e^{-\alpha e^{\beta \log t}} \qquad \text{Eq. (20)}$$

Where $X_t$ represents fraction dissolved at time t; $X_{max}$ represents maximum dissolution; a represents scale parameter describing non-dissolved portion at time t=1; and β represents dissolution rate per unit time. Rearranging assuming $X_{max}$=1 is shown in equation (20).

$$\ln(-\ln CFR) = k_G \log t + \ln \alpha \qquad \text{Eq. (21)}$$

Where $k_G$=β

According to equation (21), plotting the left-hand versus log(t) will result in a straight line with $k_G$ as the slop and lnα as the intersection.

Kinetics Models Accuracy for $NH_2$ Liposomes

Figure 15:
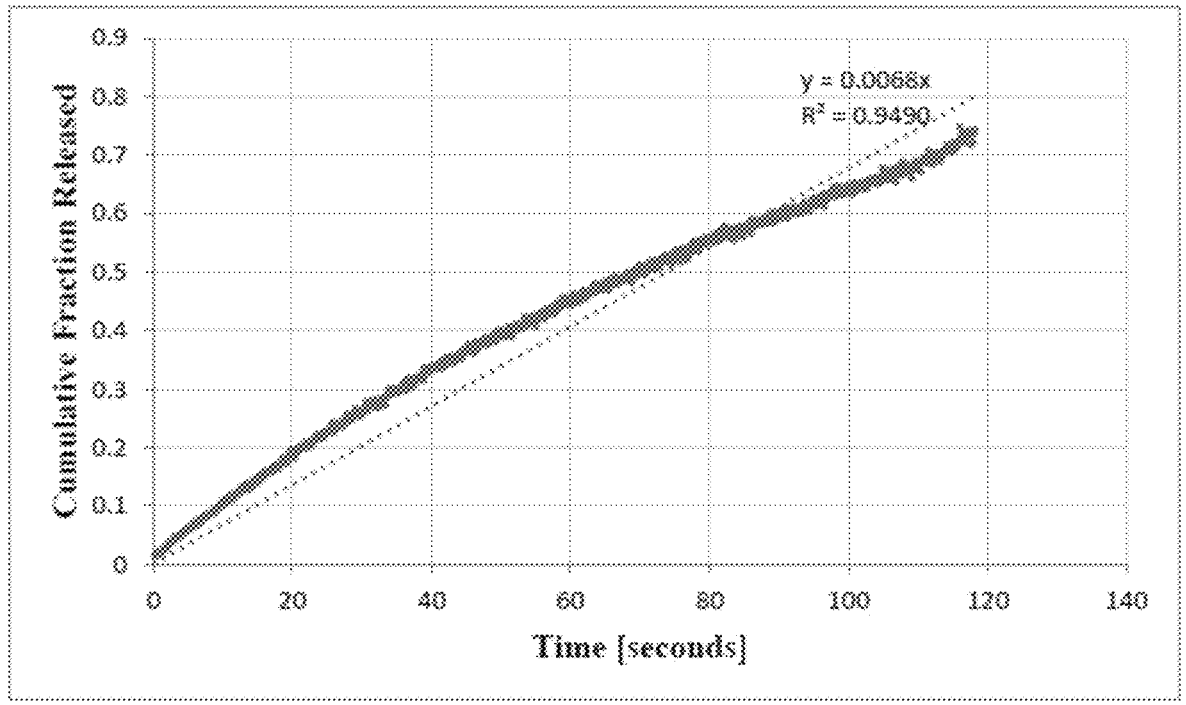
FIGS. 15-23 illustrates an embodiment of comparison between release profile of NH₂ Liposomes and different kinetic models.
Figure 16:
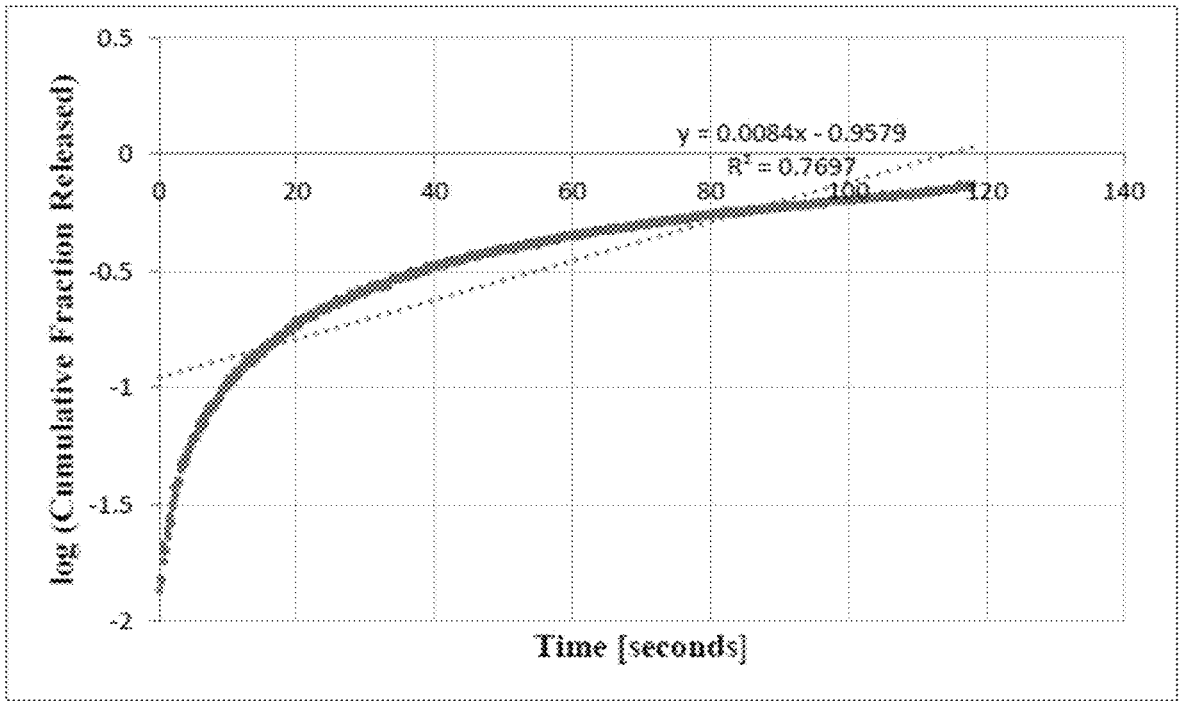
Figure 17:
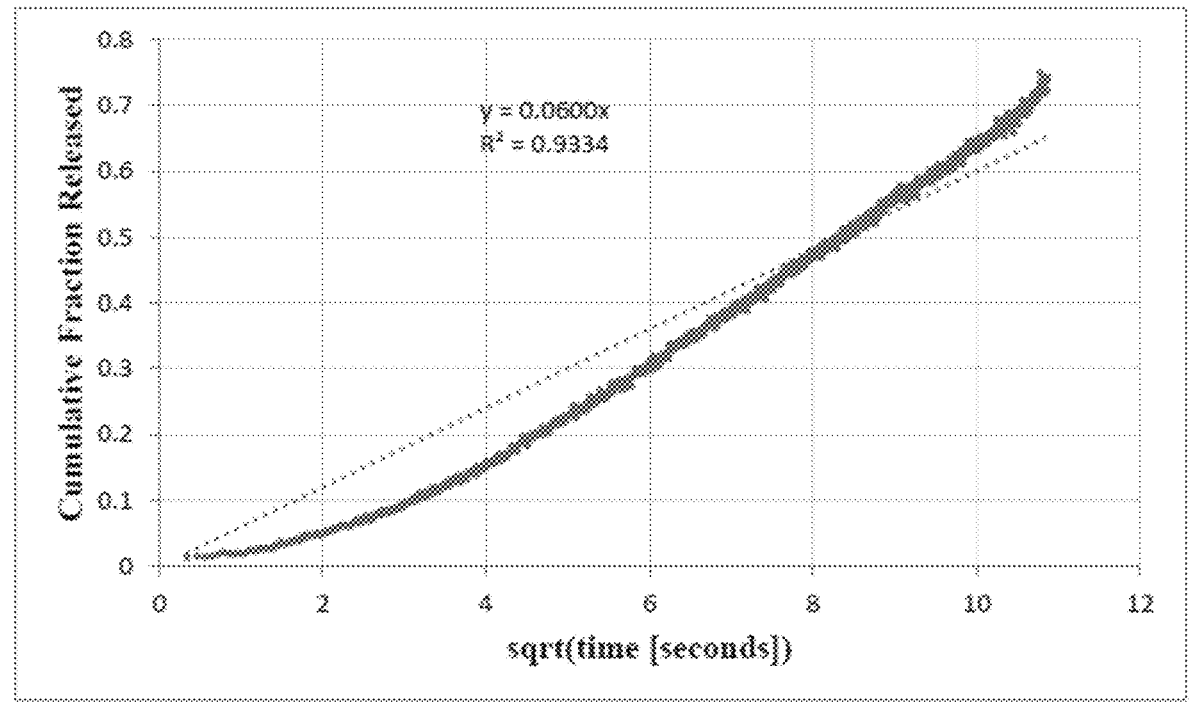
Figure 18:
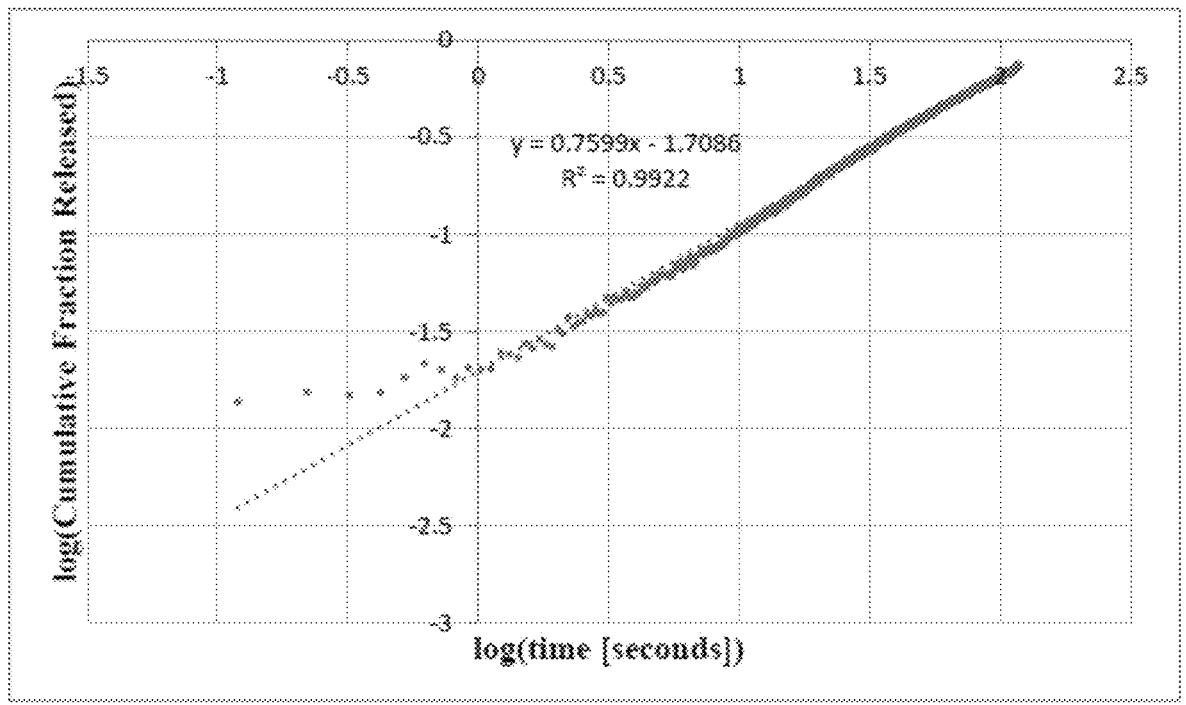
Figure 19:
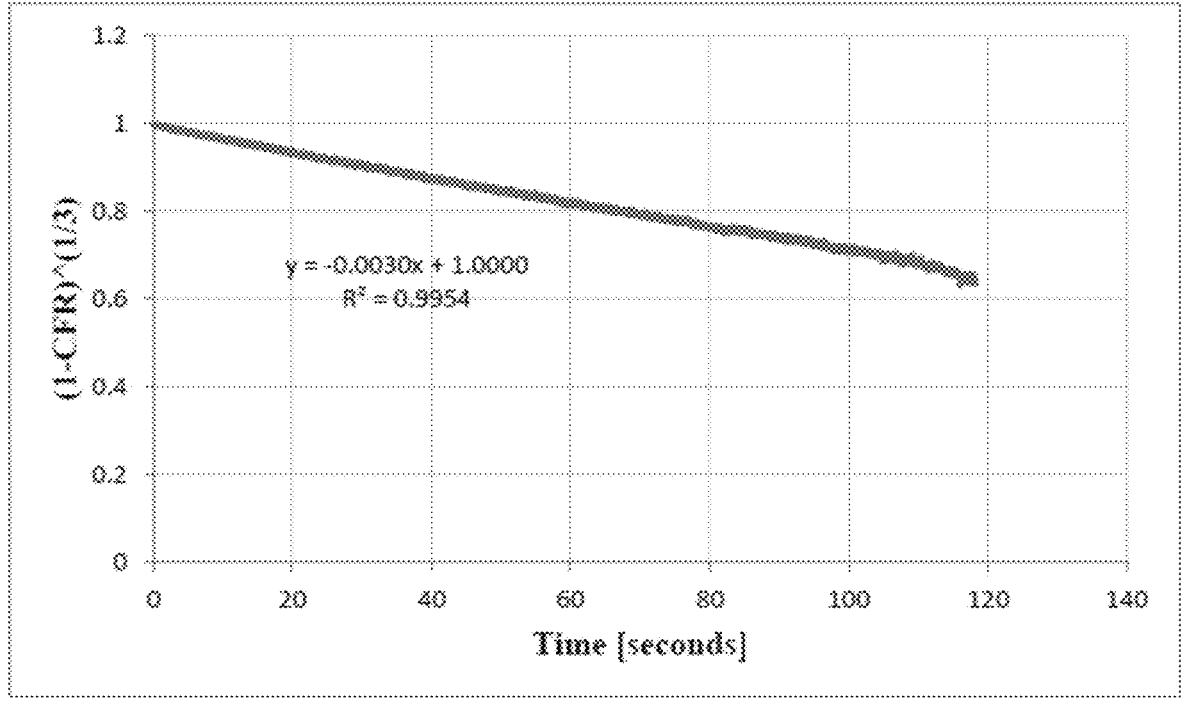
Figure 20:
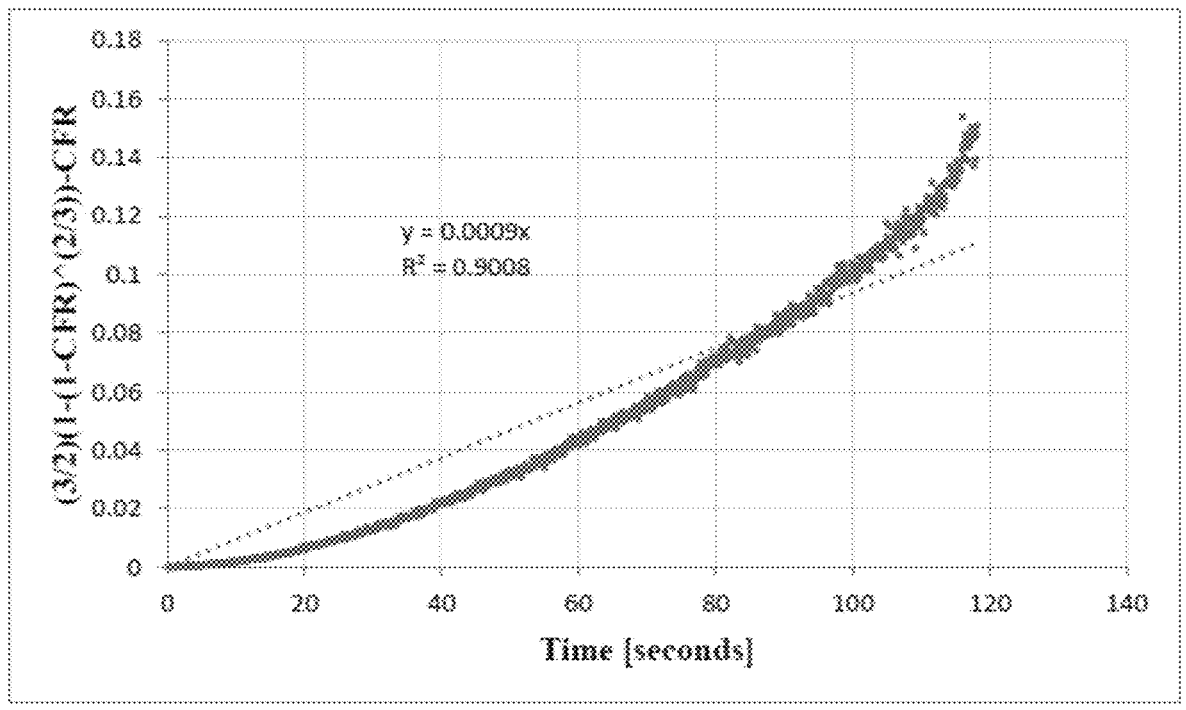
Figure 21:
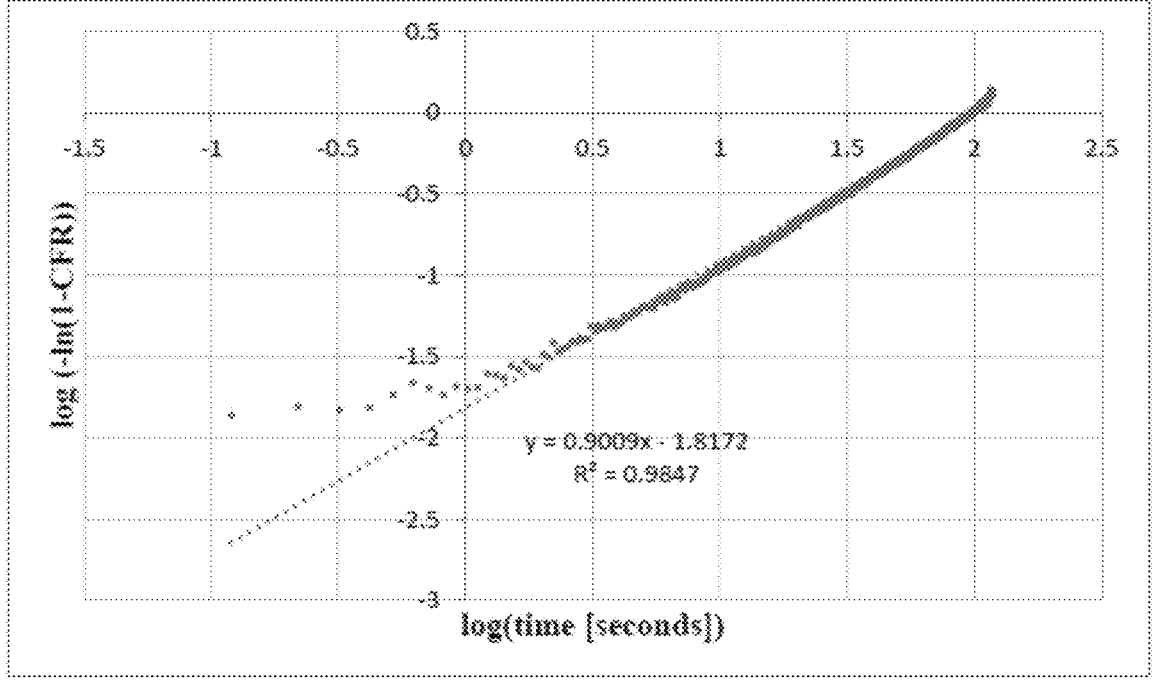
Figure 22:
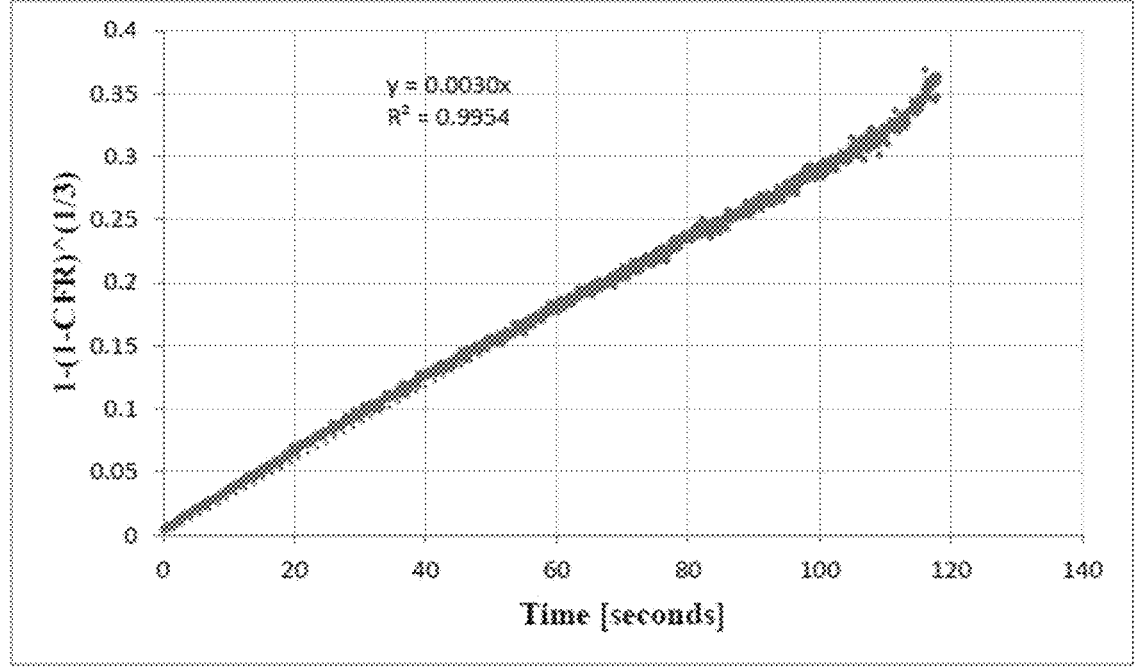
Figure 23:
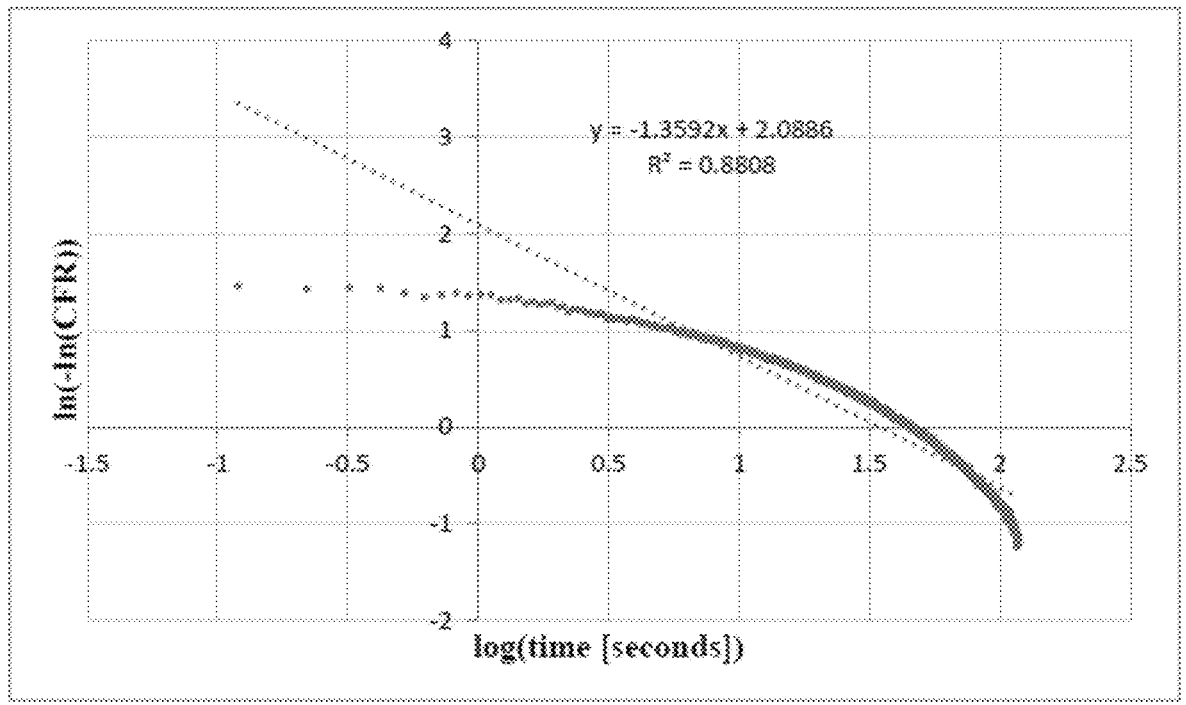

Cumulative fraction release of each batch of $NH_2$ liposomes described herein may be used in equations (4), (6), (8), (10), (12), (14), (17), (19), and (21) to construct the following graphs. To test models representation of the drug release kinetics, a straight line should appear in the graph, if the model was accurate. The suitability of each model may be determined upon creating a straight trendline of the plot. Then to test how close the data points are to this straight line, $R^2$ may be calculated. Generally, $R^2$ is an indication of the model capability to accurately represent the release data. Additionally, Parity plots were also used to demonstrate the best fitting model. FIGS. 15-23 were illustrated using the data from batch 1 of $NH_2$ liposomes at a power density of 7.46 (mW/cm$_2$), where each $R^2$ is shown on each of FIGS. 15-23. FIG. 15 illustrates zero-order plot for NH2 liposomes, batch #1. FIG. 16 illustrates first-order plot for NH2 liposomes, batch #1. FIG. 17 illustrates Higuchi model for NH2 liposomes, batch #1. FIG. 18 illustrates Korsmeyer-Peppas model for NH2 liposomes, batch #1. FIG. 19 illustrates Hixson-Crowell model for NH2 liposomes, batch #1. FIG. 20 illustrates Baker-Lonsdale model for NH2 liposomes, batch #1. FIG. 21 illustrates Weibull model for $NH_2$ liposomes, batch #1. FIG. 22 illustrates Hopfenberg model for NH2 liposomes, batch #1. FIG. 23 illustrates Gompertz model for NH2 liposomes, batch #1.

Figure 24:
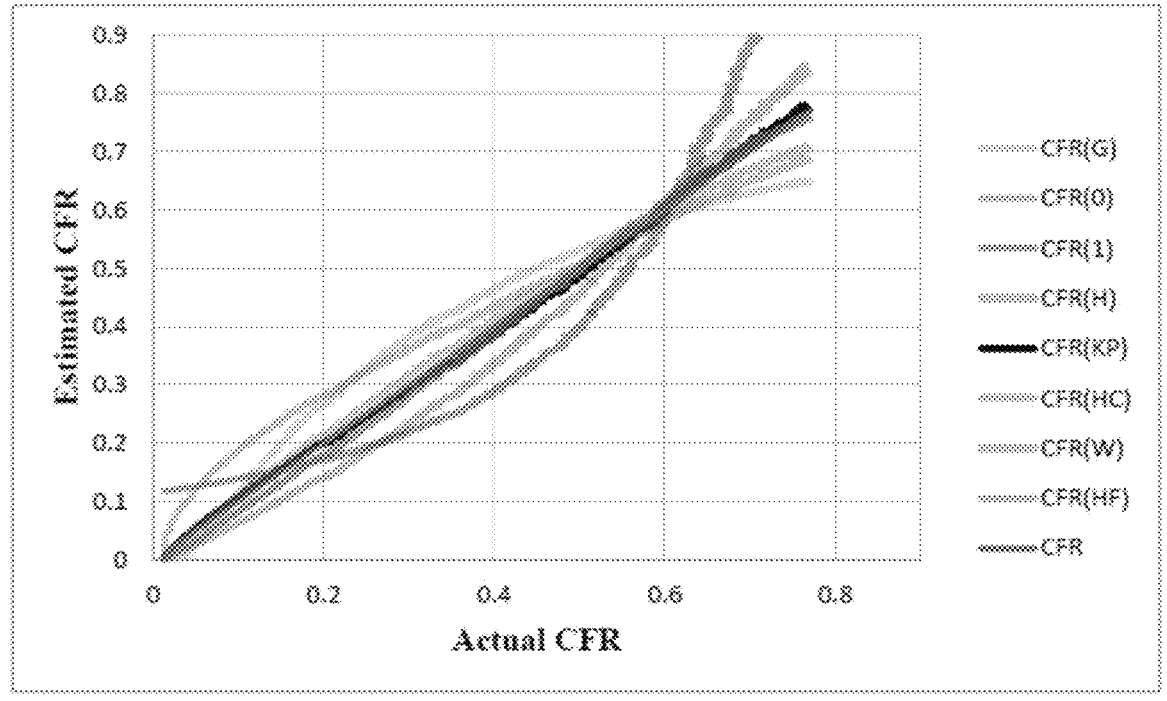
FIGS. 24-26 illustrates an embodiment of parity plots for the average of the three batches of NH₂ liposomes at each power density, using parameters estimated for different model fits.
Figure 25:
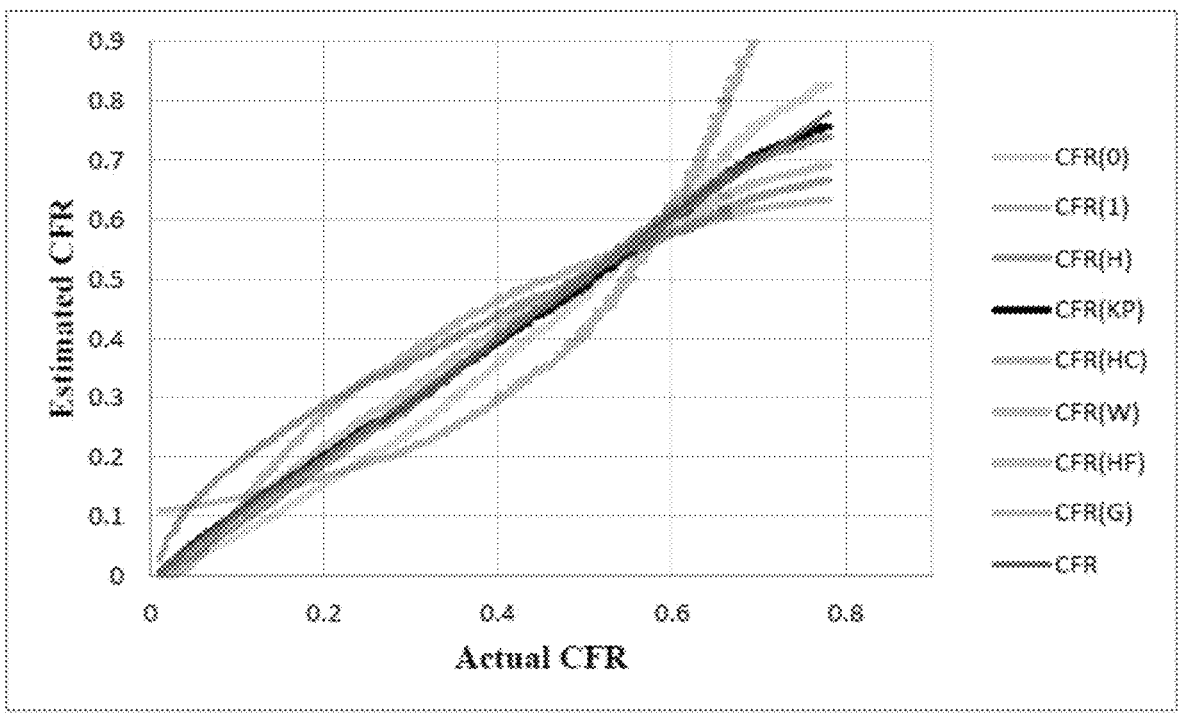
Figure 26:
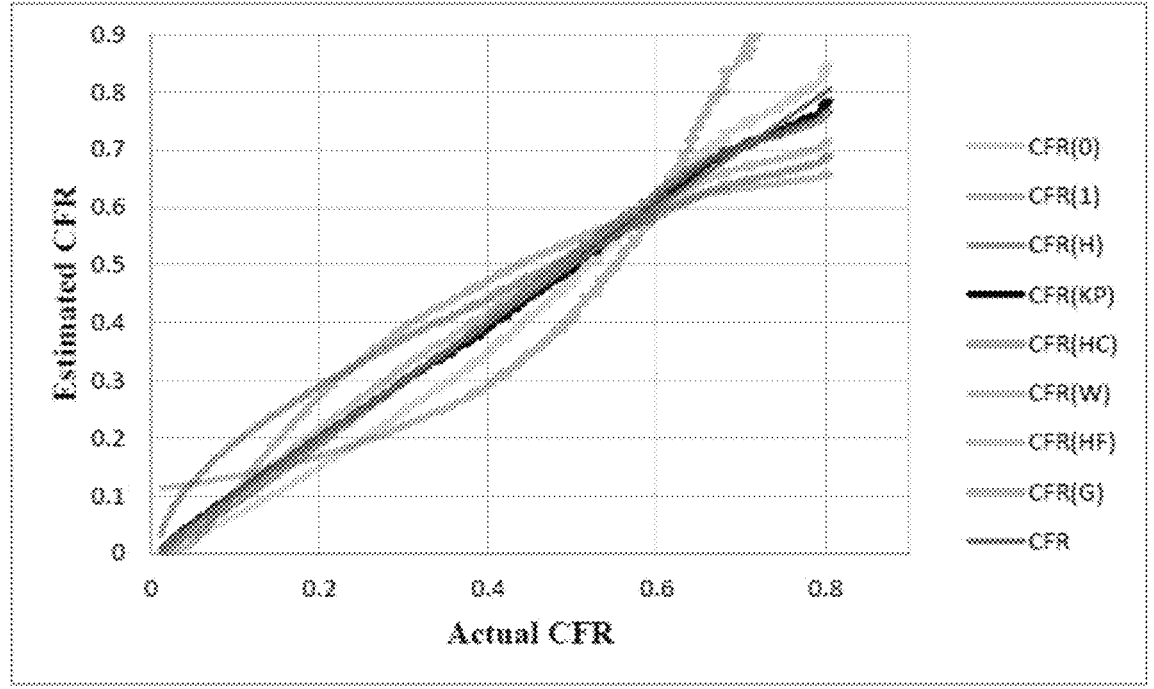

The $R^2$ values of the models for all the $NH_2$ liposomes batches at each power density according to one embodiment are summarized in Tables 11 and 12, in which averages of each model fitting parameter ($R^2$) is shown at the bottom of the table. It can be seen that Korsmeyer-Peppas shows the highest $R^2$ averaged values for $NH_2$ liposomes (0.9952), meaning that it is the best model to fit the release data. This can also be visualized in the parity plots in FIGS. 24-26 plotted for the average of the three batches of $NH_2$ liposomes at each power density, using parameters estimated for each model fit. As illustrated in FIGS. 24-26, Hixson-Crowell and Hopfenberg (colored overlapping as grey) are the second closest models after Korsmeyer-Peppas (colored in black) to the actual model (colored in red). Fourth closest was the Weibull model, while the rest of the models failed to accurately represent the release data.

TABLE 11

| $R^2$ values | NH2 liposomes batch | Zero order | First order | Higuchi | Korsmeyer-Peppas |
|---|---|---|---|---|---|
| | | | | | |
| | $R^2$ values of different models for NH2 liposomes at each power density | | | | |
| 7.46 | 1 | 0.9490 | 0.7697 | 0.9334 | 0.9922 |
| (mW/cm2) | 2 | 0.9319 | 0.7451 | 0.9434 | 0.9951 |
| | 3 | 0.9509 | 0.7697 | 0.9325 | 0.9944 |
| 9.85 | 1 | 0.9688 | 0.7811 | 0.9163 | 0.9961 |
| (mW/cm2) | 2 | 0.9558 | 0.7658 | 0.9280 | 0.9953 |
| | 3 | 0.9618 | 0.7821 | 0.9224 | 0.9952 |
| 17.31 | 1 | 0.9718 | 0.7928 | 0.9094 | 0.9950 |
| (mW/cm2) | 2 | 0.9567 | 0.7642 | 0.9282 | 0.9973 |
| | 3 | 0.9724 | 0.7823 | 0.9089 | 0.9965 |
| Average | | 0.9577 | 0.7725 | 0.9247 | 0.9952 |

TABLE 12

$R^2$ values of different models for NH2 liposomes at each power density

| $R^2$ values | NH2 liposomes batch | Hixson-Crowell | Baker-Lonsdale | Weibull | Hopfenberg | Gompertz |
|---|---|---|---|---|---|---|
| 7.46 | 1 | 0.9954 | 0.9008 | 0.9847 | 0.9954 | 0.8808 |
| (mW/cm2) | 2 | 0.9954 | 0.9117 | 0.9899 | 0.9952 | 0.879 |
| | 3 | 0.9934 | 0.8752 | 0.9832 | 0.9934 | 0.8566 |

TABLE 12-continued

R² values of different models for NH2 liposomes at each power density

| R² values | NH2 liposomes batch | Hixson-Crowell | Baker-Lonsdale | Weibull | Hopfenberg | Gompertz |
|---|---|---|---|---|---|---|
| 9.85 | 1 | 0.9957 | 0.8718 | 0.9868 | 0.9958 | 0.8744 |
| (mW/cm2) | 2 | 0.9967 | 0.8853 | 0.987 | 0.9967 | 0.8689 |
| | 3 | 0.992 | 0.8606 | 0.9831 | 0.9920 | 0.8571 |
| 17.31 | 1 | 0.9839 | 0.8251 | 0.9801 | 0.9839 | 0.8422 |
| (mW/cm2) | 2 | 0.9932 | 0.8662 | 0.9878 | 0.9932 | 0.8576 |
| | 3 | 0.9822 | 0.8212 | 0.9815 | 0.9822 | 0.8333 |
| Average | | 0.9920 | 0.8687 | 0.9849 | 0.9920 | 0.8611 |

Models Accuracy for Immunoliposomes

Figure 27:
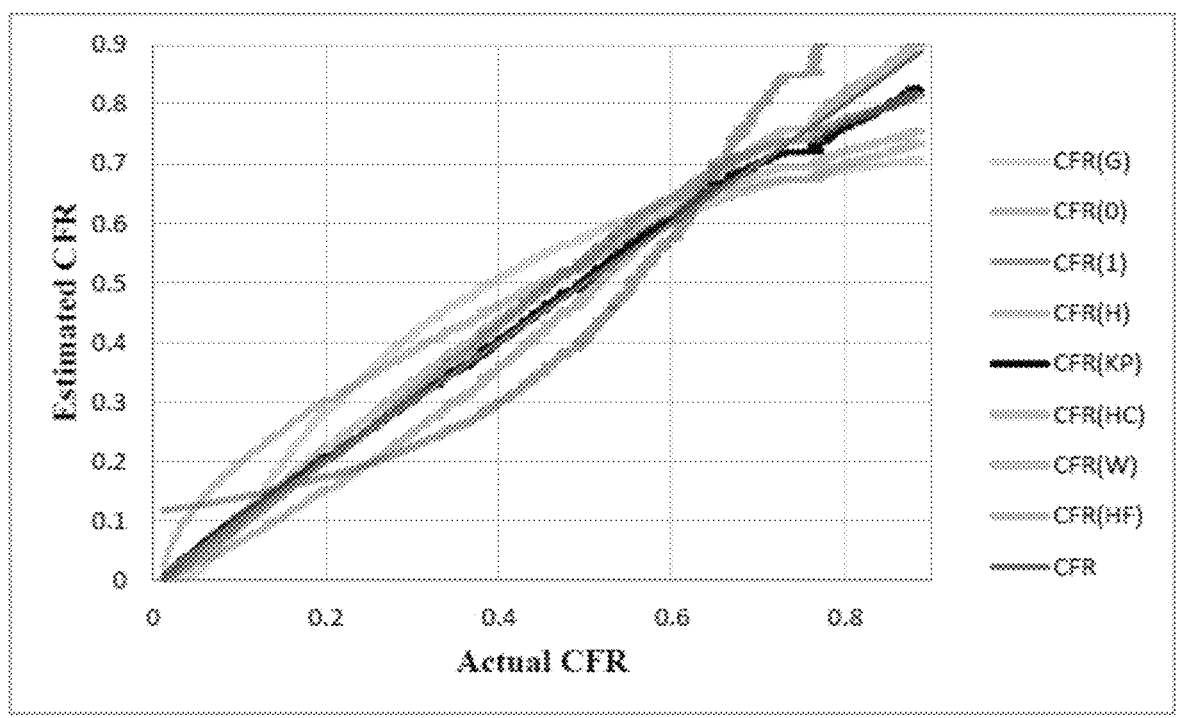
FIGS. 27-29 illustrates an embodiment of parity plots for the average of the three batches of immunoliposomes at each power density, using parameters estimated for different model fits.
Figure 28:
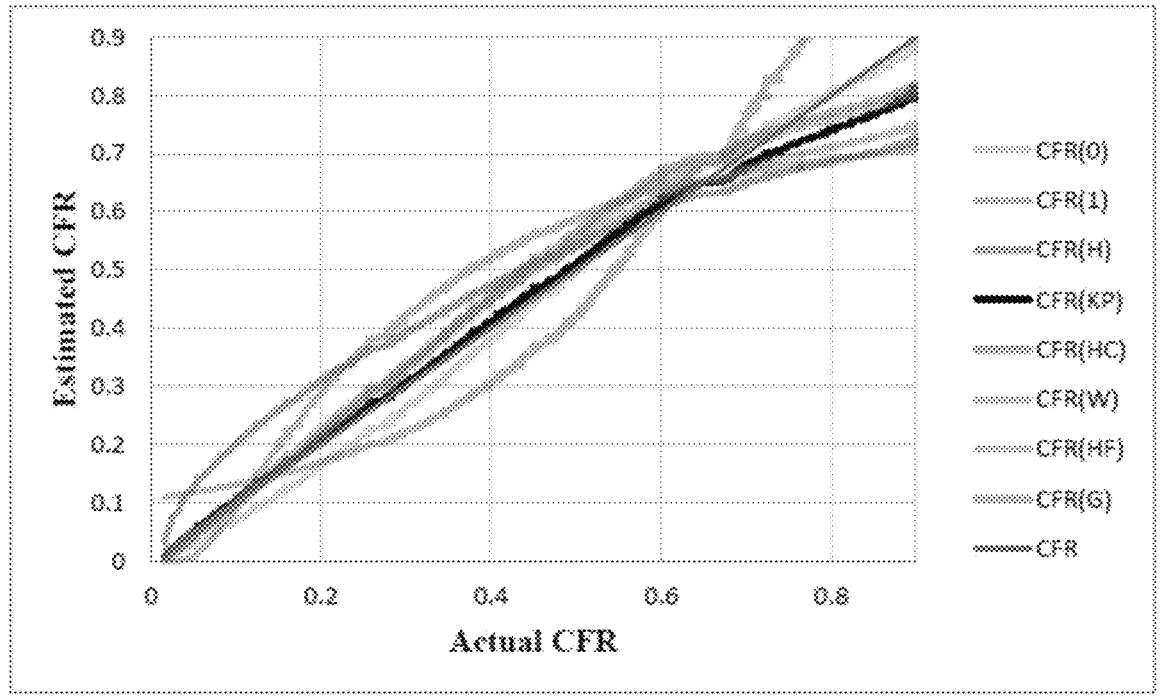
Figure 29:
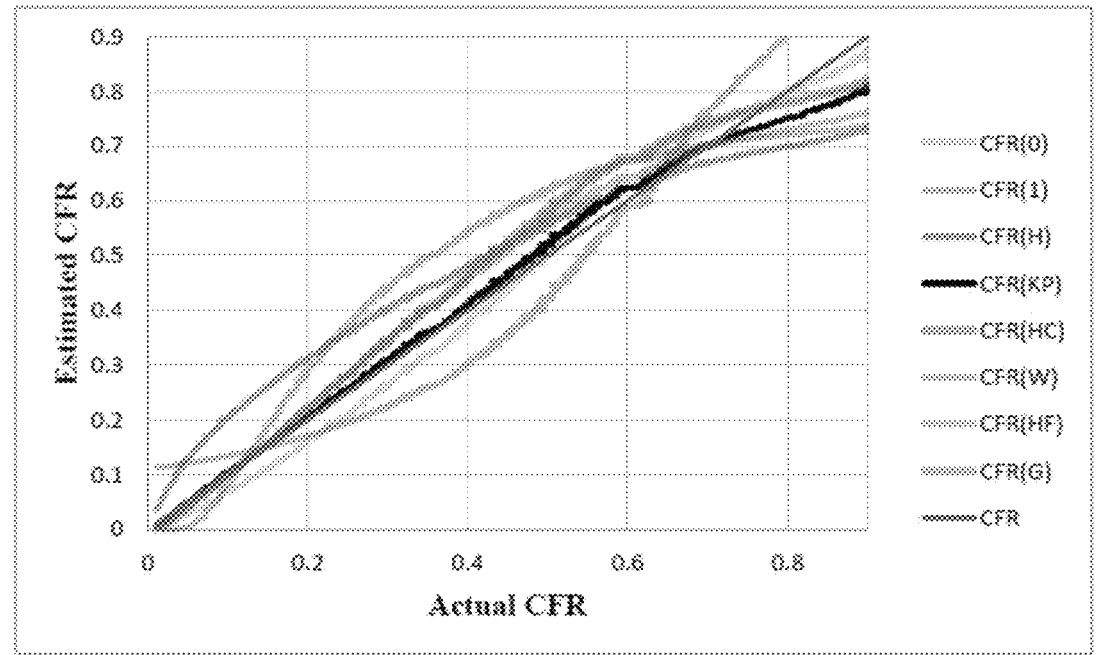

The same analysis implemented for $NH_2$ liposome may be conducted also for immunoliposomes. The summary for the $R^2$ values according to one embodiment are presented in Tables 13 and 14, in which Korsmeyer-Peppas demonstrated to have the highest $R^2$ averaged value followed by zero-order, and Weibull models. This can also be visualized in the parity plot illustrated in FIGS. 27-29, where black colored Korsmeyer-Peppas model was the closest to the red colored actual CFR values, followed by the green colored Weibull model, and then the blue colored zero-order model, and finally the Hixson-Crowell and Hopfenberg models overlapping as grey color.

TABLE 13

R² values of different models for immunoliposomes at each power density

| R² values | Immuno-liposomes batch | Zero order | First order | Higuchi | Korsmeyer-Peppas |
|---|---|---|---|---|---|
| 7.46 | 1 | 0.9729 | 0.7991 | 0.9027 | 0.9937 |
| (mW/cm2) | 2 | 0.9784 | 0.7924 | 0.9050 | 0.9936 |
| | 3 | 0.9838 | 0.8135 | 0.8856 | 0.9915 |
| 9.85 | 1 | 0.9812 | 0.8136 | 0.8782 | 0.9919 |
| (mW/cm2) | 2 | 0.9892 | 0.8221 | 0.8745 | 0.9906 |
| | 3 | 0.9892 | 0.8431 | 0.8528 | 0.9847 |
| 17.31 | 1 | 0.9820 | 0.8160 | 0.8560 | 0.9936 |
| (mW/cm2) | 2 | 0.9905 | 0.8066 | 0.8642 | 0.9957 |
| | 3 | 0.9886 | 0.8399 | 0.8640 | 0.9887 |
| Average | | 0.9840 | 0.8163 | 0.8759 | 0.9916 |

TABLE 14

R² values of different models for immunoliposomes at each power density

| R² values | Immunoliposomes batch | Hixson-Crowell | Baker-Lonsdale | Weibull | Hopfenberg | Gompertz |
|---|---|---|---|---|---|---|
| 7.46 | 1 | 0.9509 | 0.7587 | 0.9616 | 0.9509 | 0.7554 |
| (mW/cm2) | 2 | 0.9784 | 0.8116 | 0.9712 | 0.9784 | 0.7991 |
| | 3 | 0.956 | 0.7667 | 0.9582 | 0.956 | 0.7599 |
| 9.85 | 1 | 0.9379 | 0.7209 | 0.9612 | 0.9379 | 0.7611 |
| (mW/cm2) | 2 | 0.9433 | 0.7386 | 0.9557 | 0.9433 | 0.7472 |
| | 3 | 0.9066 | 0.7044 | 0.9276 | 0.9066 | 0.6735 |
| 17.31 | 1 | 0.8851 | 0.6641 | 0.9409 | 0.8851 | 0.6675 |
| (mW/cm2) | 2 | 0.9208 | 0.7231 | 0.9517 | 0.9208 | 0.702 |
| | 3 | 0.9186 | 0.7121 | 0.9379 | 0.9186 | 0.6963 |
| Average | | 0.9331 | 0.7334 | 0.9518 | 0.9331 | 0.7291 |

As described herein, both types of liposomes (i.e. the control $NH_2$ liposomes and immunoliposomes) may have similar behavior and consequently similar mechanisms. The Korsmeyer-Peppas model revealed the apparent diffusion release mechanism by calculating the n value in the model. The n values were found to be 0.7742 and 0.7896 for $NH_2$ liposomes and immunoliposomes respectively. This could be averaged for both as 0.7819. This value falls in the non-Fickian transport upper limit, and close to the super transport region. The adherence of the data to Korsmeyer-Peppas, Hopfenberg, and Hixson-Crowell, assume diffusion-driven and dissolution-driven mechanism. This could be understood considering that ultrasound make pore-like deformations during sonication allowing the drug to diffuse easily and rapidly to the outer environment.

Calculations of $k_{KP}$ Values

According to the Korsmeyer-Peppas model, a log-inverse of the intersect value yields the kip rate constant. Table 15 illustrates rate constant of Korsmeyer-Peppas model for both types of liposomes at each power density.

TABLE 15

Rate constant of Korsmeyer-Peppas model for both types of liposomes at each power density

| NH2 liposomes | 7.46 (mW/cm²) | 9.85 (mW/cm²) | 17.31 (mW/cm²) |
|---|---|---|---|
| | Kkp values (n = 0.7742) | | |
| Batch #1 | 1.9561E-02 | 2.3243E-02 | 3.1710E-02 |
| Batch #2 | 2.1592E-02 | 2.6303E-02 | 3.4135E-02 |
| Batch #3 | 2.1404E-02 | 2.6934E-02 | 3.1261E-02 |
| Average | 2.0853E-02 | 2.5493E-02 | 3.2369E-02 |
| Std. dev | 1.12E-03 | 1.97E-03 | 1.55E-03 |

TABLE 15-continued

| Rate constant of Korsmeyer-Peppas model for both types of liposomes at each power density | | | |
|---|---|---|---|
| NH2 liposomes | 7.46 (mW/cm$^2$) | 9.85 (mW/cm$^2$) | 17.31 (mW/cm$^2$) |
| Immunoliposomes (n = 0.7896) | | | |
| Batch #1 | 2.2594E−02 | 2.5627E−02 | 3.2352E−02 |
| Batch #2 | 1.9770E−02 | 2.5322E−02 | 3.0409E−02 |
| Batch #3 | 2.0455E−02 | 2.7277E−02 | 3.5067E−02 |
| Average | 2.0940E−02 | 2.6075E−02 | 3.2609E−02 |
| Std. dev | 1.47E−03 | 1.05E−03 | 2.34E−03 |

In Table 16, a two-factor ANOVA analysis is shown. As shown in Table 15, the F-value is lower than the F-critical value, and hence no significant difference exists between kip values for both types of liposomes. This indicates that the release rate constant may not be affected by the type of liposomes (NH$_2$ liposomes or immunoliposomes). This means that immunoliposomes follow the same release pattern as the control ones. The second F-value is shown to be higher that the F-critical, which indicates that k$_{KP}$, are significantly affected by the power density. This indicates that a higher release rate may be obtained with increased power density.

TABLE 16

| Two-factor ANOVA analysis of KKP values | | | | | |
|---|---|---|---|---|---|
| Source of Variation | SS | df | MS | F | p-value | F crit |
| Sample | 4.14E−07 | 1 | 4.1383E−07 | 0.1524 | 0.7031 | 4.7472 |
| Columns | 0.000406 | 2 | 0.00020324 | 74.822 | 2E−07 | 3.8853 |
| Interaction | 1.93E−07 | 2 | 9.6343E−08 | 0.0355 | 0.9653 | 3.8853 |
| Within | 3.26E−05 | 12 | 2.7163E−06 | | | |
| Total | 0.00044 | 17 | | | | |

OTHER EMBODIMENTS

The foregoing description and examples has been set forth merely to illustrate the disclosure and are not intended to being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular"

or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems and methods for and of making liposomes, including control and targeted liposomes, have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems and methods for and of making liposomes, including control and targeted liposomes. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

In summary, various embodiments and examples of systems and methods for and of making liposomes, including control and targeted liposomes, have been disclosed. Although the systems and methods for and of making liposomes, including control and targeted liposomes, have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Thus, the scope of this disclosure should not be limited by the particular disclosed embodiments described herein, but should be determined only by a fair reading of the claims that follow.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. A method of breast cancer treatment, comprising:
   delivering an actively targeted liposome, the actively targeted liposome comprising:
      a lipid bilayer forming a spherical shell, the spherical shell comprising an interior liposomal cavity, the lipid bilayer comprising cholesterol and polyethylene glycol, a plurality of cetuximab molecules linked to a surface of the actively targeted liposome, and a chemotherapeutic drug, the chemotherapeutic drug comprising at least one of a hydrophilic chemotherapeutic drug contained within the interior liposomal cavity and a hydrophobic chemotherapeutic drug contained within the lipid bilayer of the actively targeted liposome; and allowing the actively targeted liposome to circulate throughout a circulatory system for a time sufficient to allow aggregation of a therapeutic quantity of actively targeted liposomes at a treatment area comprising a cancer;

applying ultrasound to the treatment area such that the actively targeted liposome is critically disrupted thereby releasing the chemotherapeutic drug in the treatment area;

wherein the ultrasound applied to the treatment area comprises a low frequency ultrasound with a power density between about 0.002 W/cm$^2$ and 0.060 W/cm$^2$.

2. The method of claim 1, wherein the ultrasound applied to the treatment area comprises a low frequency ultrasound.

3. The method of claim 2, wherein the low frequency ultrasound comprises a frequency of about 20 kHz.

4. The method of claim 2, wherein the low frequency ultrasound applied to the treatment area is applied for less than about 6 minutes.

5. The method of claim 1, wherein the ultrasound applied to the treatment area comprises high frequency ultrasound.

6. The method of claim 1, wherein pulsed ultrasound is applied to the treatment area.

7. The method of claim 1, wherein the lipid bilayer of the actively targeted liposome comprises one or more PEGylated lipids.

8. The method of claim 7, wherein the plurality of cetuximab molecules are linked to a distal end of the PEG chain.

9. The method of claim 1, wherein the actively targeted liposome comprises a protein density of 7.5-30 molecules per liposome.

10. The method of claim 1, wherein the actively targeted liposome comprises a mean radius between 50-150 nm.

11. The method of claim 1, wherein the actively targeted liposome comprises 6 to 12 cetuximab molecules.

12. The method of claim 6, wherein the ultrasound is pulsed two times.

13. The method of claim 6, wherein the ultrasound is pulsed three times.

14. The method of claim 1, wherein the chemotherapeutic drug comprises calcein.

15. The method of claim 1, wherein the chemotherapeutic drug is selected from the group of doxorubicin, annamycin, daunorubicin, vincristine, cisplatin derivatives, paclitaxel 5-fluorouracil derivatives, camptothecin derivatives, and retinoids.

16. The method of claim 1, wherein the actively targeted liposome comprises a plurality of vesicles, the plurality of vesicles linked to about 9 cetuximab molecules.

17. The method of claim 1, wherein the plurality of cetuximab molecules are linked to the surface of the actively targeted liposome using cyanuric chloride.

18. The method of claim 2, wherein the low frequency ultrasound comprises a power density of one of 0.00746 W/cm$^2$, 0.00985 W/cm$^2$, and 0.01731 W/cm$^2$.

19. The method of claim 7, wherein the ratio of PEGylated lipids to non-PEGylated lipids is below 10%.

20. The method of claim 15, wherein the chemotherapeutic drug is doxorubicin.

\* \* \* \* \*